(12) United States Patent
Slim

(10) Patent No.: US 7,960,111 B2
(45) Date of Patent: Jun. 14, 2011

(54) NALP7-BASED DIAGNOSIS OF FEMALE REPRODUCTIVE CONDITIONS

(75) Inventor: Rima Slim, Montreal (CA)

(73) Assignee: The Royal Institution for the Advancement of Learning/McGill University, Montreal (CA)

( * ) Notice: Subject to any disclaimer, the term of this patent is extended or adjusted under 35 U.S.C. 154(b) by 584 days.

(21) Appl. No.: 11/997,678

(22) PCT Filed: Aug. 3, 2006

(86) PCT No.: PCT/CA2006/001256
§ 371 (c)(1),
(2), (4) Date: Feb. 1, 2008

(87) PCT Pub. No.: WO2007/014463
PCT Pub. Date: Feb. 8, 2007

(65) Prior Publication Data
US 2008/0213779 A1 Sep. 4, 2008

Related U.S. Application Data

(60) Provisional application No. 60/704,896, filed on Aug. 3, 2005.

(51) Int. Cl.
*C12Q 1/68* (2006.01)
*C12P 19/34* (2006.01)
*G01N 33/53* (2006.01)
*G01N 33/86* (2006.01)

(52) U.S. Cl. ............... 435/6; 435/91.2; 435/7.1; 436/89

(58) Field of Classification Search .................. None
See application file for complete search history.

(56) References Cited

U.S. PATENT DOCUMENTS
2003/0092019 A1* 5/2003 Meyer et al. .................... 435/6

FOREIGN PATENT DOCUMENTS
WO      WO 2007/014463 A1     2/2007

OTHER PUBLICATIONS

NCBI Submitted SNP(ss) details: ss899497; printed from http://www.ncbi.nlm.nih.gov/SNP/snp_ss.cgi?subsnp_id=899497 on May 19, 2010 12:45:52 PM, three pages.*
Hacker et al (1997) Gut. 40:623-627.*
Lucentini (2004) The Scientist. Dec. 20, 2004, p. 20.*
Ioannidis (Nature Genetics, vol. 29, pp. 306-309, Nov. 2001).*
Mummidi et al. The Journal of Biological Chemistry, vol. 275, No. 25, Issue of Jun. 23, pp. 18946-18961, 2000.*
Juppner Bone vol. 17, No. 2, Supplement Aug. 1995:39S-42S.*
Glodsby et al., Immunology. WH Freeman and Company. 2003, p. 141.*
Helwani, M. et al. A familial case of recurrent hydatidform molar pregnancies with biparental genomic contribution. Hum Genet, 1999, 105:112-115.
Hodges, M.D. et al. Genetic refinement and physical mapping of a biparental complete hydatidiform mole locus on . . . J Med Genet, 2003, 40:95-doi:10.1136/jmg.40.8.e95.
Kinoshita, T. et al. PYPAF3, a PYRIN-containing APAF-1-like protein, is a feedback regulator of caspase-1-dependent interleukin-1B . . . J Biol Chem, 2005, 280 (23): 21720-21725.
Kircheisen, R., and Ried, T. Hydatidiform moles. Hum Reprod, 1994, 9(9):1783-1785.
Moglabey, Y.B. et al. Genetic mapping of a material locus responsible for familial hydatidiform moles. Hum Mol Genet, 1999, 8(4):667-671.
Mazhar, S.B. and Janjua, S. Recurrent familial hydatiform mole. J Pakistan Inst Med Sci, 1995, 6(1,2):383-6.
Murdoch, S. et al. Mutation in NALP7 cause recurrent hydatidiform moles and reproductive wastage in humans. Nat Genet, 2006, 38(3): 300-302 and suppl. 4 pages.
Okada, K. et al. Oncogenic role of NALP7 in testicular seminomas. Cancer Sci, 2004, 95(12):949-954.
Qian, J. et al. Women heterozygous for NALP7/NLRP7 mutations are at risk for reproductive wastage: report of two novel mutations. Hum Mutation, 2007, DOI:10.1002/humu.9498.
Sensi, A. et al. Mole maker phenotype: possible narrowing of the candidate region. Eur J Hum Genet, 2000, 8:641-644.
Seoud, M. et al. Recurrent molar pregnancies in a family with extensive intermarriage: report of a family and review of the literature. Obstet & Gynecol, 1995, 86:692-695.
Silver, R.M. et al. Lipopolysaccharide-induces fetal death: the role of tumor-necrosis factor alpha. Biol Reprod, 1994, 50:1108-1112.

* cited by examiner

*Primary Examiner* — Juliet C Switzer
(74) *Attorney, Agent, or Firm* — Goudreau Gage Dubuc; S. Serge Shahinian; Alain Dumont

(57) ABSTRACT

Methods, reagents and kits are described for the diagnosis of a female reproductive condition, based on the detection of an alteration in a NALP7-encoding nucleic acid or a NALP7 polypeptide, relative to a corresponding wild-type NALP7-encoding nucleic acid or NALP7 polypeptide.

10 Claims, 16 Drawing Sheets

NALP7 genomic DNA sequence from human chromosome 19 genomic contig.
(SEQ ID NO: 1; GenBank accession No. NT_011109)

```
   1 ttcttcagcc ttaacctaag gtctcatact cggagcacta tgacatcgcc ccagctagag
  61 tggactctgc agacccttct ggagcagctg aacgaggatg aattaaagag tttcaaatcc
 121 cttttatggg cttttcccct cgaagacgtg ctacagaaga ccccatggtc tgaggtggaa
 181 gaggctgatg gcaagaaact ggcagaaatt ctggtcaaca cctcctcaga aaattggata
 241 aggaatgcga ctgtgaacat cttggaagag atgaatctca cggaattgtg taagatggca
 301 aaggctgaga tgatgggtaa gtagaacctg gggtgtcctg gtcatttttt tttttttttt
 361 ttttttttg agatggagtc tcgttctgtc gcccaggctg gagtgtaagg ctggagtgca
 421 gtggcgagat ctgggctcac tgcaacctcc gcctctgggt tcaagtgatt ctcctatctc
 481 agcctccgga gtagctggga ttacaggcgt gtttcaccac acctggctaa tttttttttt
 541 tttgtatttt tagtagagat ggggttttgc catgttggcc aggctggtct tgatctcctg
 601 accttgtgat ccgcccacct cagccttcca aagtgctgtg attacaggca tgagccacca
 661 tgcctggctg acactttatg tacaataatg tctgatttac gaagtgtaaa ttactgtgtc
 721 aggcttacat ctaagtattt tacagaggac ggacaggtgc aagaaataga taatcctgag
 781 ctgggagatg cagaagaaga ctcggagtta gcaaagccag gtgggtaaat acggtcctat
 841 ggtcatgagt ttggtgtttg agagcatgca aggtgcatca cttcttcctg gttttattca
 901 tttctggtag tttttttttt ttttgagacg gaatcttgct ctgtagccca ggctggagtg
 961 tagtggctcc gtctctgctc attgcaacct ctgcctcccg ggttcaagca attctctgcc
1021 tcagcctcct gagtagccgg gattacaggc ggccgccact accccagct aatgttttgt
1081 attttagta gagatggggt ttcactatct tggccaggct ggtcttgaac tcctgacctc
1141 aagtgatcca cccaccttgg cctcccaaag tgccgggatt acaagcatga gacaccgtgc
1201 ctggccctca tttctggtac ttgacaaaat aattcagaaa atcatcatca tcaacctcaa
1261 ctgtcctatg ggctgtcact gcaggtgaaa aggaaggatg gagaaattca atggagaaac
1321 agtctttggt ctggaagaac acctttggc aaggagacat tgacaatttc catgacgacg
1381 tcactctgag aaaccaacgg ttcattccat tcttgaatcc cagaacaccc aggaagctaa
1441 caccttacac ggtggtgctg cacggccccg caggcgtggg gaaaaccacg ctggccaaaa
1501 agtgtatgct ggactggaca gactgcaacc tcagcccgac gctcagatac gcgttctacc
1561 tcagctgcaa ggagctcagc cgcatgggcc cctgcagttt tgcagagctg atctccaaag
1621 actggcctga attgcaggat gacattccaa gcatcctagc ccaagcacag agaatcctgt
1681 tcgtggtcga tggccttgat gagctgaaag tcccacctgg ggcgctgatc caggacatct
1741 gcggggactg ggagaagaag aagccggtgc ccgtcctcct ggggagtttg ctgaagagga
1801 agatgttacc cagggcagcc ttgctggtca ccacgcgcc cagggcactg agggacctcc
1861 agctcctggc gcagcagccg atctacgtaa gggtggaggg cttcctggag gaggacagga
1921 gggcctattt cctgagacac tttggagacg aggaccaagc catgcgtgcc tttgagctaa
1981 tgaggagcaa cgcggccctg ttccagctgg gctcggcccc cgcggtgtgc tggattgtgt
2041 gcacgactct gaagctgcag atggagaagg gggaggaccc ggtccccacc tgcctcaccc
2101 gcacggggct gttcctgcgt ttcctctgca gccggttccc gcagggcgca cagctgcggg
2161 gcgcgctgcg gacgctgagc ctcctggccg cgcagggcct gtgggcgcag atgtccgtgt
2221 tccaccgaga ggacctggaa aggctcgggg tgcaggagtc cgacctccgt ctgttcctgg
2281 acggagacat cctccgccag gacagagtct ccaaaggctg ctactccttc atccaccctca
2341 gcttccagca gtttctcact gccctgttct acgccctgga gaaggaggag gggaggaca
2401 gggacggcca cgcctgggac atcggggacg tacagaagct gctttccgga gaagaaagac
2461 tcaagaaccc cgacctgatt caagtaggac acttcttatt cggcctcgct aacgagaaga
2521 gagccaagga gttggaggcc acttttggct gccggatgtc accggacatc aaacaggaat
2581 tgctgcaatg caaagcacat cttcatgcaa ataagccctt atccgtgacc gacctgaagg
2641 aggtcttggg ctgcctgtat gagtctcagg aggaggagct ggcgaaggtg gtggtggccc
2701 cgttcaagga aatttctatt cacctgacaa atacttctga agtgatgcat tgttccttca
2761 gcctgaagca ttgtcaagac ttgcagaaac tctcactgca ggtagcaaag ggggtgttcc
2821 tggagaatta catggatttt gaactggaca ttgaattga aggtaagaa ctgttttccc
2881 atcccacgct ccactaggaa gaggccagcg tctccttgc cctgtcgctt actgtcagaa
2941 tttccctctg gctggacttc tttccagctt catgttcaac gtggagacac gacttggcaa
3001 ttaggaattg gggctttta tttttggagac ggagtctcgc tctgtccccc aggctggagt
3061 gcagtggcgc gatcttggct cactgcaacc tccgcctccc gggttcaagt gattctcctg
3121 cctcagcctc ccgagtagct gggactatgg gcgtgcacca ccttgcccgg ttaattattt
3181 tatttttttg tagagatggg gtctcagtt tctagcccaa gttggtctta aactcctggg
3241 ctcaagtgat cttcccactt tggcctagca aagtgttggg attacaggca tgagccacct
3301 cactcagcct tatctattat tttatttttt ttgtaaaact taagatctat actggtagca
3361 aagcatgtga tgcaatattg tttactatag acactgtttt aggttggtgc aaaagtaatt
3421 gtggtttttg ccattgaaat gtggtttgca gatgcccatc tcaccatgca ggtactagtc
```

Figure 6

```
3481 ctaagagatg aacgtgtgtt ctcctgcagg tgcacttacc taaccattcc gaactgggct
3541 cggcaggatc ttcgctctct tcgcctctgg acagatttct gctctctctt cagctcaaac
3601 agcaacctca agtttctgga agtgaaacaa agcttcctga gtgactcttc tgtgcggatt
3661 ctttgtgacc acgtaacccg tagcacctgt catctgcaga aagtggagta agtagaagct
3721 catcttgcaa ggaagaccct gaacgatgac taagcttctt gtactttgt tttttaaatt
3781 tggaaatgtg ctgtttcatc tccatgtatt tggggatttt ccagctgtct tttttttttt
3841 tttttttttt ggtgagacgg agatttactc ttgttgccca ggctggagtg caatggcgcg
3901 atctcagctc actgcatcct ccacctccca ggttcaagca attctcctgc ctcagcctcc
3961 cgagtagctg ggattacagg catgtgccac cttgcccggc taattttgta cttttagcac
4021 agacaggttt tcaccgtgtt gcccaggctg atctcgagct cctgacctca ggtgatttgc
4081 ctgcctcggc cttccaaagt gctgggatta taggcatgag ccgctgcacc tggccccttt
4141 tttattttt attttttctg agacagagtt tcactctgtc acctaggcgc tggagtgcaa
4201 tgacttaatc ttgtgttttt agtagaggtg gaattttctc catcttggcc aggcttgtct
4261 cgaactcctg acctaaggtg atgcgcctgc ctcggtcttc gaaagtgctg ggattacagg
4321 catgagccac catgcctggc ccagctatc tttttttttgg tttgttttgt taccaaaaca
4381 aaccaaaaag taggtacaag tacaggttag ttacacaggt aaccgtgtgt cataggagtt
4441 tgttgtacag attattttgt cacccaagta ttaagcctag tacccccttag ttgttttttcc
4501 tgatcctctg cttcttgact tttttttttt tttttgagac agtctcgcta tgttccccag
4561 gctggagtgc agtgcagcaa tctcggctca ctgcaagccc tgcctcccgg gttcatgcca
4621 ttctcctgcc tcagcctccc gagtagctgg gactacaggc gcccgccacc acgcccggct
4681 agttttttgt aattttagta aagacgggt ttcaccgtgt tagccaggat ggtcttgatc
4741 tcctgacctc gtgatccacc cgcctcggcc tcggcctccc aaagtgctgg gattacaggc
4801 gtgagccacc acaccggcg aatttttttt tcttttgaga tggagtcttg ctctgttgcc
4861 caggctggag tgcagtggtg cggtctcggc tcactgcaac ctctgcctcc tggattcaag
4921 tgattctcct acctcagcct cccgaatacc tgggactaca agcatgcccc tccatgtgca
4981 gctaatttt gtattttag tagagacggg gcttccccat gttggccagg ctggtctcga
5041 actcctgacc tcaggcgatc tgcctgcctc ggccccagct aatttatttt ttgtagagat
5101 ggagtttcac catgtgccc aggttggtct cagactcctg acctcaggtt atcctcctgc
5161 ctcagcctcc caaagtgctg gggttacaga cacgagccac tgcacccggc caagaacttc
5221 taataatttc taaatgtgaa acagcttttt gtttatacat gcctccacac aatgtgagta
5281 ttaatcactc caagtggaat ctcttctgct tttccctagg attaaaaacg tcacccctga
5341 caccgcgtac cgggacttct gtcttgcttt cattgggaag aagaccctca cgcacctgac
5401 cctggcaggg cacatcgagt gggaacgcac gatgatgctg atgctgtgtg acctgctcag
5461 aaatcataaa tgcaacctgc agtacctgag gtgggtctca cggtcacggc tctccccagc
5521 acctggagtc cactgcaccg tgttgctggg ggatctagga aaaagggtaa ccactccaga
5581 tgccgtccca gacagggaat gtattcctca acaggcctg tgtggggag tcggcctctc
5641 ctctttcccc caccagcttg tcttctgtgt tgcataacca gctatccatg caaagaaaca
5701 ccccgaattc tgtgctgggt tccagcttta gggacatgct attcctgact gcaccttgcc
5761 taattgttgg gattgagagc agtggccccc agcttttct gcaccgcggg ccggttttgc
5821 acaagacagt ttttccaca gacgggtttg gggtagttt tgggatgaaa ctgttcgatc
5881 tcagatcagg cacaggagct aatcgttggt gcctgatcct atggagtgca tgatcctcgc
5941 actttgggag cctgaggaga atggatcatc aatctcagat catcaggagt taggtattca
6001 taaggagcat gcaaccttct ctgcactcaa tgagaatctt tttttttttt tttttctttt
6061 gagacagttt tattcttgtc acccaggctg gagcgcagtg gcgcgatctc gttcactgca
6121 acctccgcct cctgggttca agcagttctg cctcagcttc ccgagtagct ggggttacag
6181 gcgtgcacca ccacgcctgg caaatgtttg tatttttaat agagacaggg tttcaccatg
6241 ttggccaggc tggtctcgaa ctcctgacct caagtgatcc gcctgtctcg gcctcccaaa
6301 gtgctaggat tacaggcatg aaccactgcg cctggccagg ataaaatttt tatttgagt
6361 attaagcatc aatttgcccc ttctagtccc agctacagtg gatgctgagg tgggaggatc
6421 atttgagccc aggagacagg ttgtggtgac ctgtgatcat gccactgcac tccagcctgg
6481 gcaacagagc gagatcctgt ctcaaaaaaa aatttttttt ttcccccctg caaaatcatc
6541 cacacaggcc gttttggtga acattgcac agaattgtat tacaatctct tggagaagtg
6601 gctggatgtt accctaatgg ccatggggat acttgaagaa gcagaggcaa cattagatct
6661 ctccagtaat tcaggccagg gttggaggca tgagtagaat gagataaacc aaagacataa
6721 tgtcttggga agtgaagcag aagaagctga tctgggccag gcgcggtggc tcacacctgt
6781 aatcccagta cttcggtagg ccaagtgggg tggatcacct gaggtcagga gttcaagacc
6841 agtgtggcca acatggtgaa atcccgtctc tactaaaaat acaaaaattg gcgaatgcct
6901 gtaatcccag ctacttcgga ggctgaggca ggagaatagc ttgaacccgg gaggcggagg
6961 ctgcagtgag gtgagatcac gcctttgcat tccagactgg gcaacagagt gaaactctgt
7021 ctcaaaaaaa aaaagctgat agggtatact ctgtcctccc agaagaatga cttttcccac
7081 tcttttcaca ggttgggagg tcactgtgcc accccggagc agtgggctga attcttctat
```

Figure 6 continued

```
7141 gtcctcaaag ccaaccagtc cctgaagcac ctgcgtctct cagccaatgt gctcctggat
7201 gagggtgcca tgttgctgta caagaccatg acacgcccaa aacacttcct gcagatgttg
7261 tcgtaagtct cctcttccca tgggcagctc tggtttagtt ctggggctat agaagagaaa
7321 gggtaacacc tgacttactg cgccacccac gtggcgcctc ttgctgaaat aaacacctgc
7381 ttcaggcccg gcacggtggc tcctgcctgt aatctcagca gagaggtggg cggatcatct
7441 gagttcagga gttcgagacc aacctggcca acatggtgaa accctgtttc tattaaaaat
7501 accaaaaaca ggccgggtgc ggtggctcat gcctgtaatc ccagcacgtt gggaggccaa
7561 ggcggggaga tcacgaggtc aagagatcga gaccatcctg gctaacatgg tgaaaccccg
7621 tctctactaa aaatacaaa aaattatcca ggtgtggtgg gcgcctgtag tcccagctac
7681 tcaggaggct gagtcagcag aatggtgtaa acctggagg cggcgattgg cagtgaaccg
7741 agatcgcgcc actgcactcc agcctgggcg acagagcgag actccgtctc aaaaacaaca
7801 cctgtgtcct gtgatggctc caggtggacc gctgcatctt ggccttctcg ccttcctgct
7861 cttttgtggc catgatgact cccacaggag agaggcagg ggatgaacag gaagggctga
7921 agctgagtac cctagcatgt ggacatcact gagcaggttg gagttgtgga aatgttctca
7981 tccttctacc atttgtttca tattttttgca ggttggaaaa ctgtcgtctt acagaagcca
8041 gttgcaagga ccttgctgct gtcttggttg tcagcaagaa gctgacacac ctgtgcttgg
8101 ccaagaaccc cattgggat acaggggtga agtttctgtg tgagggcttg agttaccctg
8161 attgtaaact gcagaccttg gtgtaagtcc ctgctgggtg tgtgtgtgtg tgcacatgaa
8221 ttcaagcagg agagacatga aagtacttgt taattcattt caaatgtaac ttttaaaaac
8281 ctggtaagaa ttaaagaaca ggcagaggcc aggcgtggtg gctcatgcct gtaatcccag
8341 cactttggga ggccgaggcg ggtggatcat gaggtcagga tggagacc atcctggtta
8401 acatggtgaa accctgtctg tactaaaaat accaaaaatt agccaggtgt ggtggcggat
8461 gcctgtagtc ccagctactt gggaggatga gacaggagaa tggcgtgaac ctggaaggcg
8521 gaggttgcag tgagccgaga tcgcaccact gcactccagc ctgggcgaca gaacaagact
8581 ccttctcaaa aaaacaaaga aacaaaaaaa accaggcaga tacaggtaga aacatgttaa
8641 tatttgcatg tcagcagagc ctcttcctgc tatgaaggaa gatttgagat gagtagttgg
8701 ttctcggatc tgatgctttg tgtgtgttct ttcaaattcc tatgacatag tactgcctgc
8761 tattggaggt agattgagtt atgtggtagg gccagtggca ccttttttta aacttttatt
8821 tccataggtt attggggaac aggtggtgaa tggtgggcag atcacctaag gttcgagacc
8881 agcctggcca acatggtgaa aacccatcgc tactaaaaaa tacaaaaatt aaccaggctt
8941 ggtggtgcgt gcctatagta ccagctactc agaaggctga ggtaggagaa tcgcttgaat
9001 ctgggaggca gaggctgcag tgagctgaga tggcgccact gcactccagc ccgggcgaca
9061 gagtgagact ccgtctcaag aaaaaaacaa aaaaaaactc aacaaaaatc cttatttgta
9121 aaagacatag gtggcaggtt ggaattgacc cacgaactat agttggctga atcttgttat
9181 atggaaagaa gcccagccgtg agctaccgt tcacattaaa attatggtta gaaaaatatt
9241 caagagattg catagggttg aagacctgtt cctgttcaga aattctagct agtggtcatt
9301 tctgagattc attttttttt ttttggatga agtctcactc tgtcgcccag actggaatgc
9361 agtggtgtaa tcttggctga ctgcaacttc tgcctcccag gttcaagcga ttctcctgcc
9421 tcagcctccc aagtagctgg gattacaggt gccctccacc atgcctggct aattttttgca
9481 ctttttagtgg agatgaggtt tcaccatgtt ggccaggctg gtcttgaact cctggcctta
9541 agtgatctgc ctgcctcggc ctcccaaagt gctggcgttc aggcatgag ccactgtgcc
9601 tggcttagaa taactattgt taaacaaaca gtcacctacc tgatcgttat acgaagtgta
9661 cctgcaccaa acatcacac tataccccta tatgtaga atgtgtcagt taaagacaaa
9721 acttaaacat gaaataaaat gacaggaaa gtgaaatttc cataatctaa ccacgcagaa
9781 aataagtgac ccaggctca gatcctgtcc tgggtcggtc tgaacccaga gcctaagctg
9841 ttgtcccagg cagagctgga aatgatgga atcagaaggc catttcgatg ttttttttttt
9901 tttttttaaca gtctctctct gtcaccaggc tggagtgcag tggtgcgatc ttggctcact
9961 gcaacctccg cttcctgggt tcaagtaatt ctcctacctc agcctcctga gtagctagga
10021 ttacaggcat gggccgccac acctggctaa ttttttttttt ttttgagat ggagtttcgc
10081 tcttgccag gctggagtgc aatggtgcaa tctctgctca ccacaacctc cgtctcccca
10141 gttcaagaga ttctcctgcc tcagcctcct gagtagctgg gattacaggc atgtgccacc
10201 acacctggct aattttgtat tttagtaga cgggtttc tccatattgc tcaggctggt
10261 cttgaactcc cgacctcagg tgatctgtct gcctcagcct cccaaagtgc tgagattaca
10321 ggtgtgagcc atcgtgccca gctaattttt gtatttagta aagatggggt ttcaccactt
10381 tggccaggct ggtcttgaac tcctgatctt gtgattcacc caccttggtc tcccaaagtg
10441 ctgagattac aggtttgagc caccgcgccc ggcccgattt tgtatttttt tagtagagat
10501 ggggtttcac catgttggtc aggctggtct tgaactcctg acctcaaatg atctgcccgt
10561 cttggcctcc cactgctgtg attataggcg tgagccactg tgcccggccc atttgcatgc
10621 ttttatgtgc aagcccacct ggaagtatat agctccagtt catgggtcaa ttcctacctg
10681 ccacctatgt tttatataaa tactttttgt tgttgttgtt gttttcttga gacggagtct
10741 cgctctgtcg cccgggctgg agtgcagtgg cgcgatctca gctcactgca gcctctgcct
10801 cccggattca agcgattctc ctgcctcagt cttctgagta gctggcacta caggcgtgca
```

Figure 6 : continued

```
10861 ccaccaagtc tggttatata ggtggcgggc acctataatc ccagctactt gggaggctga
10921 ggcagaagaa tcgcttgaac ctgggaggca gaggttgcag tgagccaaga gtgcagcact
10981 gcattccagt atataagtgg aaggtatata gtgttggaaa taactgcttc acagggcgtt
11041 agccagaggg ataacaggct tctcttcctt tgattatcct gtaggttaca gcaatgcagc
11101 ataaccaagc ttggctgtag atatctctca gaggcgctcc aagaagcctg cagcctcaca
11161 aacctggact tgagtatcaa ccagatagct cgtggattgt ggattctctg tcaggcatta
11221 gagaatccaa actgtaacct aaaacaccta cggtaggcga ttttcttttt cttctttctt
11281 tcttttttg agacagggtc ttgctctgtc cccagcctg gagtgcagtg gggtgattac
11341 ggctcactgc ggcttcggtc ttccaggctt gatcggttct cccacctcag cctcctgagt
11401 agctggctct acaggcatgt attaccatgg ccaggtaact gttttctgta gagatgaggt
11461 cttgtcatct ttcccgggct ggttttgaat tctggtgctc aaggaatcct cccacctcgg
11521 cctcccaatg tgctaggatt acaggcatga gccatcatgc ctggcctcat ttttaaagtg
11581 tttggaaatc tggaaatcct taatttctat gttttctttt tttttttttt ttttgagac
11641 ggagcctcgt tctagttgcc caggctggag tgcagtggcg cgatctcggc ttactgcaac
11701 ctcttcctcc cgggttctcg ctattctcct gcctcagcct cctgagtagc tgggactaca
11761 gatgcccgcc accgtgcctg gctaattttt tttgtatttt tagtagagat gggtttcaca
11821 gtgttagcca ggatggtctc gatctcctga cctcatgatc tgcccgcctt ggccttccaa
11881 agtgctggga ttacaggcgt gagccaccac gcccggccaa tttctatgtt ttcaatatct
11941 cagactgtat cacttcggat ccagttttaa gatcaaaccc ctccagaaac tgaatatatg
12001 tgggtgggca cttctaaagt caggtagagg gcctggagaa gtgaaatata tataacaatg
12061 gcccccagtg acctggactt cagcagcatg ctgcttctgc tgggatccag taatcaggaa
12121 gcagtgagcc tgccccacct cataaaccca gggaaccata ggtgggatac caccccaga
12181 aaatgcaaag tctccacaaa tggaatggcg agctcttcat cacttctctc cccaaagttt
12241 gtcagttgca tctcttggat gcaacctatt ttccaactag aatctgcaat cctaatgcaa
12301 agagaatctg cacgtcatta ctacttagct ttgctgtaga gtaaagaaaa aaaacactag
12361 aacacagggt acttttttc tttttcaga cagagtctcg ctttgtcacc caggctggag
12421 tgcagtggtg cgatcttggc tcactgcaac ctcagcctcc aaggttcaag cgattctcct
12481 gattgagctg agtagttggg attacaggcg tgcaccacca tacccagcta attttgtat
12541 ttttagtaga gaccaggttt caccatgtta gccagactgg tctcaaactc ctgacctcaa
12601 gtgatccacc tgcctcaacc tcccaaagtg ctgggattac aggcatgagc caccattcct
12661 ggcctcctga gtttcttaa cccatccccc tgaggaatat ttcaagcctc aagccagacc
12721 gtgataccttt tatttccaaa gactcaaaag ctcaatgcaa acggtggat tacctggtgt
12781 cttgttcctg taatctcagc tactgactga atcctagatt ctcgggaggc tggggcagga
12841 gaatcgcttg aacccaggag gcggaggttg cagtgagccg agatcacgcc attgcactcc
12901 agccttggca acaagagtga aactctgcct taaaaaaaac aaaaccaaag gcttctacag
12961 tggcctacag ggccttatgg gggatcctcg tgtaagttat gagccataaa tcattctact
13021 ttctcactag ctcagtattt tatttacaag attccctccc ccagttagca tgctggttca
13081 tgatctacca tccttcagtt tctttcctca tatcactttc caaaagagga cttaaatgac
13141 cagcataagt ctagccaatc aatgcctctc tgtttgactt acctctaccc tgtttatttt
13201 aataccatca tccattgtct tcaatagaac atatcgagat gtctgctgtc actaaaaact
13261 ctgaggacaa ggatttcttc tgctcactcc cctctgcctt tcctcactac tggagcccca
13321 gcaaatatgc tgcttgtttt tttgtttgt tttgtttgag accaagtctc actctttcac
13381 ccaagctgga atgcagtggt gatatgttgg ctaactacaa cctctgcctc ctggttcagg
13441 cgattctcct gcctctcgag tagctagaat tataggtggt tccaccatac ctggctaatt
13501 tttgtatttt cattttatgt tatatatttg tgagatggag tctcattcta ttgcccaggc
13561 tggagtgcag tggcgcaatc tgggctcact gtaacctccg cctcccaggc tgaagcgatt
13621 cttgtgcctc agcctcccaa gtagctagca ttaaaggcac acaccaccat gcatggctaa
13681 tttttttgtag agatggggtt ttgccatgtt ggcctggctg gtctcgaact cctgacctca
13741 ggtgatctac cctcctcggc ctcccaaggt gctgggcta caggtgtctg tccccacgcc
13801 ctgcctaatc tttgtatttt tagtagagat ggggtttgac cgtgttggca aggctggtct
13861 cgaacacctg gcctcaagtg atccacccgc cttggcctcc gaagtgttgg gattacacg
13921 cttgagccac tacctgctca gtgaatgcgt ggattccat gttcttcctc aacagcctct
13981 ggagctgctc cctcatgcct ttctattgtc agcatcttgg atctgctctc ctcagcaatc
14041 agaagcttga aactctggac ctgggccaga atcatttgtg gaagagtggc ataattaagc
14101 tctttggggt tctaagacaa agaactggat ccttgaagat actcaggtat gggttttttg
14161 tttgttttg ttttgttttt tgtttttt ttttgagat ggagtcgtg tctgtcattc
14221 aggctggagt gcagtggcgc aatcttggct caccgcaacc tctgcctctc aggttcaagc
14281 aattctcctg cctcagcctc atgagtagct gggcctagag gcatgccaac atgtccagct
14341 aatttttttc tttttctttt tttttttttg agacggagtt ttgttcttgt agcccaggct
14401 ggagtgcagt ggtgcgatct ggctcactg caaccccac ctcctgggtt caagcgattc
14461 tcccaccttg gcctcccaag tagctggaat tacagatgcc tgccaccatg cctggctaat
14521 tttttagtag agaggggttt caccatgttg gccaggctag tcttgaactc ctgacctcag
```

Figure 6: continued

```
14581 gtgagccacc tgcctcggcc tcccaaagtg gtgggattac agaggtgagc cattgcaccc
14641 ggccttttg gtttttgctt tttgggatgg agtctcactg ttgcccaggc tggagtgcag
14701 tggcgcgatc ttgactcact gcagcctcct tctcacaggt tgaagcgatt ttcctgcctc
14761 aacctcctga gtagctggga ttacaggtac acaccaccac agctggctaa tttttttttt
14821 tttttttttt ttttaaagac agagtctctc tctgtccccc aggctggagt gcagtggcgc
14881 tatctcggct cagtgcaacc tctgcctcct gggttcaagt gattctcctg cctcagcctc
14941 ctgagtagct aggattacag tcgctcgcca ccacacccag ctaattttg tatttttagt
15001 agagatgggg ttttgccatg ttggccaggc tggtctcgag ctcctgacct caggtgatct
15061 tctcgccttg gcctcccaaa gtgctgggat tacaggcatg agccactgca cctggccaat
15121 ttttgtagtt tttagtagag atggggtttc accatgttgg tcaggttggt ctcaaactcc
15181 caacctcagg tgatccacct gcctcagcct ctcaaagtgc cgggattaca ggcgtgagcc
15241 actgtgctcg gccctgggat ggctgtttca catggtgaat ttcccatgca gagaagagtt
15301 tttttgggag tgtgtgtact cttgtgtagg atcaacttaa ggcatctttc tatagcacac
15361 tcctagctta ggagataatt taaaaattag atacttttct aaaatgctct gtgaattgaa
15421 tattgtccaa ctttccccca aaacacttag tcctaggcat actgagagtt taaatcatcc
15481 tggagtacag actggaagct tgtgtgtatg tgtgtgcatg agcacacaca cacacacaca
15541 cacaccccta atcattatat ccaaaaatag gtagttccca gagctgtcct gggtcttagc
15601 ttttcagaag atcgtcctac agatgctccc ttagttgtga cccgtgtata tcttttcaat
15661 gacttatttg tatttttat tttttttga gacggagtct ttttttgag acggagtctg
15721 tcttttttt tgaatctgtc tttttttga gacagagact ccagtctctg tcgcccaggc
15781 tggagtgaag cggtgcgatc tcggctcact gcaagctcca cctcccgggt tcacgccatt
15841 ctcctgcctc agcctcccga gcagctggga ctacaggcgc cgccaccac gcccggctaa
15901 ttttttgtat ttttagtaga gatggggttt cactatgttg gccaggctgg tctcgaattc
15961 ctgacctcag gtgatctgcc cacctcgcc tcccaaagtg ctgggattac aggcgtgagc
16021 caccgcgccc ggcctcagtg acttatttta acgtaatcta cctttagttt cttcttgcct
16081 ttgtcttttc ttttctgaga caacgttttg ctctgctgca ctgtgtggcc gtgttgccga
16141 ggttctcaaa ctcctggctt caaacgatcc tcctgtcttg gcctcacaaa gtacccggat
16201 tgcaggcgtg agccactgtg cacagcccac ttgtcttatt caagagttat tttagttgta
16261 gagatgatac gcatgtaaac tgcttcatga tgcccagtgt tgcattattg gaacgctaag
16321 catgtgggag ttatttatat cctgctcaag gtacgatttt tcacacgtct gcagttcaaa
16381 taattgtaac ctctggcata aatgggttaa ggttttaggg gtatatcatg aaacttgagc
16441 taaatagtgt catgcttctc ttgttggtgg gaccgaggtc tgtaatgcca ccaaggacta
16501 ttggtgacaa atctctagcc ccctgtggtc tcttatgtca tatgtttggg gcgtatttct
16561 tttctcattc ctcagttcct cctttgggag gccaagtgg gaggattgtt tgaggccagg
16621 agtttgagac cagcctgggc aacatagcaa gccagtgtct ccacaatcac caccccctcat
16681 gttcacatac acaggcttgc atgctgcagc cacgttagag ccaagtttgc tatcattaac
16741 cctggggttc actctggcat tctcttagtt ctactgaagg tttgatttgc cactattttt
16801 tatttattta tttggaggca gagtctcgct ctgtcacccg ggctgcagta cagtggtgcg
16861 gtattggctc actgcaacat ctgcctccca ggttcaaagc gattctcctg tctcagcctc
16921 ctgagtagct ggtattacag ttgtctgcca ccatgcccag ctaattttg tatttttagt
16981 agagacgggg tttcactatg ttggccaggc tggtctcgaa ttcctgacct caggtgatct
17041 gcccgcctcg gcctcccaaa gtgctggaat tataggcgtg agtcaccgtg caccagcctg
17101 attatctatt ttttaaattt atttttaaa ggcatgtttt actctgttac caggctggag
17161 tgcagtaggg caatctctag ctcgttgcaa cctccgcctc ctgggctcaa gtgatcctct
17221 tgcctccgcc tcccgagtag ctgggactat aggcgtgcac caccattcct ggctaacttt
17281 ttctattttt ggtagagaca gggtttcacc gtgttgccca ggctggtctt gaactgcgga
17341 gctcaagcaa tctgcctgcc ttggcctccc aaagtgctgg gactacaggt gcgagacacc
17401 gtgcctggcc ataatctttt ttttcttaga cttataagga tcccattgt gtgggtctaa
17461 atttcttttt agaaaacttt tctgactggg tgctgtggct cacatctgta atcccatggc
17521 tttgggaggc cgaggtggat ggatcacttg aggccagaag ttcgagacca gcctggctaa
17581 catgtcgaaa ccccatctct actgtaaata caaaacttag ccaagcgtgg tggtgcacac
17641 ctgtaatcac agttactcag gagcctgagg catgagaatt gcttgaactt gggagctgga
17701 ggttgcagag agccaagatg gcaccactgt accccagcct gggcaacaga gcaagaccct
17761 gtcccccaga aaatcccaaa aacgtttcct gctttgagtg tttgaaaaca gatattcagg
17821 catcctgggt agttgagaat gaatttctgg gaacatttgt gttctctgat ccctccaggt
17881 tgaagaccta tgaaactaat ttggaaatca agaagctgtt ggaggaagtg aaagaaaaga
17941 atcccaagct gactattgat tgcaatgctt ccgggcaac ggcacctccg tgctgtgact
18001 ttttttgctg agcagcctgg gatcgctcta cgaattcac aggaagcggg attcgggtct
18061 ctaagatgtc ttatgaatgc aggtcagagg gtcacatgtt aacactagag tctgtcgaga
18121 ggtaggattt gacactggtt ttctcactat ttttgggaga ttctgcacga gtcacgcacc
18181 ccccttcacat gacgctatgt actttctcac agggataata aagttagagc actctcgttg
18241 ca
```

Figure 6: continued

DNA Sequence of Human NALP7, 980 amino acid isoform (SEQ ID NO: 2; GenBank accession No. AY154462)

```
   1 caggctggaa gcaagacctg acctgaggga gttcttcagc cttaacctaa ggtctcatac
  61 tcggagcact atgacatcgc cccagctaga gtggactctg cagacccttc tggagcagct
 121 gaacgaggat gaattaaaga gtttcaaatc cctttatgg gcttttcccc tcgaagacgt
 181 gctacagaag accccatggt ctgaggtgga agaggctgat ggcaagaaac tggcagaaat
 241 tctggtcaac acctcctcag aaaattggat aaggaatgcg actgtgaaca tcttggaaga
 301 gatgaatctc acggaattgt gtaagatggc aaaggctgag atgatggagg acggacaggt
 361 gcaagaaata gataatcctg agctgggaga tgcagaagaa gactcggagt tagcaaagcc
 421 aggtgaaaag gaaggatgga gaaattcaat ggagaaacag tcttttggtct ggaagaacac
 481 cttttggcaa ggagacattg acaatttcca tgacgacgtc actctgagaa accaacggtt
 541 cattccattc ttgaatccca gaacacccag gaagctaaca ccttacacgg tggtgctgca
 601 cggccccgca ggcgtgggga aaaccacgct ggccaaaaag tgtatgctgg actggacaga
 661 ctgcaacctc agcccgacgc tcagatacgc gttctacctc agctgcaagg agctcagccg
 721 catgggcccc tgcagttttg cagagctgat ctccaaagac tggcctgaat tgcaggatga
 781 cattccaagc atcctagccc aagcacagag aatcctgttc gtggtcgatg gccttgatga
 841 gctgaaagtc ccacctgggg cgctgatcca ggacatctgc ggggactggg agaagaagaa
 901 gccggtgccc gtcctcctgg ggagtttgct gaagaggaag atgttaccca gggcagcctt
 961 gctggtcacc acgcggccca gggcactgag ggacctccag ctcctggcgc agcagccgat
1021 ctacgtaagg gtggagggct tcctggagga ggacaggagg gcctatttcc tgagacactt
1081 tggagacgag gaccaagcca tgcgtgcctt tgagctaatg aggagcaacg cggccctgtt
1141 ccagctgggc tcgcccccg cggtgtgctg gattgtgtgc acgactctga gctgcagat
1201 ggagaagggg gaggacccgg tccccaccct gcctcacccgc acggggctgt tcctgcgttt
1261 cctctgcagc cggttcccgc agggcgcaca gctgcgggc gcgctgcgga cgctgagcct
1321 cctggccgcg cagggcctgt ggcgcagat gtccgtgttc caccgagagg acctggaaag
1381 gctcggggtg caggagtccg acctccgtct gttcctggac ggagacatcc tccgccagga
1441 cagagtctcc aaaggctgct actccttcat ccacctcagc ttccagcagt ttctcactgc
1501 cctgttctac gccctggaga aggaggaggg ggaggacagg gacggccacg cctgggacat
1561 cggggacgta cagaagctgc tttccggaga agaaagactc aagaaccccg acctgattca
1621 agtaggacac ttcttattcg gcctcgctaa cgagaagaga gccaaggagt tggaggccac
1681 ttttggctgc cggatgtcac cggacatcaa acaggaattg ctgcaatgca aagcacatct
1741 tcatgcaaat aagcccttat ccgtgaccga cctgaaggag gtcttgggct gcctgtatga
1801 gtctcaggag gaggagctgg cgaaggtggt ggtggccccg ttcaaggaaa tttctattca
1861 cctgacaaat acttctgaag tgatgcattg ttccttcagc ctgaagcatt gtcaagactt
1921 gcagaaactc tcactgcagg tagcaaaggg ggtgttcctg gagaattaca tggattttga
1981 actggacatt gaatttgaaa ggtgcactta cctaaccatt ccgaactggg ctcggcagga
2041 tcttcgctct cttcgcctct ggacagattt ctgctctctc ttcagctcaa acagcaacct
2101 caagtttctg gaagtgaaac aaagcttcct gagtgactct tctgtgcgga ttctttgtga
2161 ccacgtaacc cgtagcacct gtcatctgca gaaagtggag attaaaaacg tcaccccctga
2221 caccgcgtac cggacttct gtcttgcttt cattgggaag aagaccctca cgcacctgac
2281 cctggcaggg cacatcgagt gggaacgcac gatgatgctg atgctgtgtg acctgctcag
2341 aaatcataaa tgcaacctgc agtacctgag gttgggaggt cactgtgcca ccccggagca
2401 gtgggctgaa ttcttctatg tcctcaaagc caaccagtcc ctgaagcacc tgcgtctctc
2461 agccaatgtg ctcctggatg agggtgccat tgtgctgtac aagaccatga cacgcccaaa
2521 acacttcctg cagatgttgt cgttggaaaa ctgtcgtctt acagaagcca gttgcaagga
2581 ccttgctgct gtcttggttg tcagcaagaa gctgacacac ctgtgcttgg ccaagaaccc
2641 cattggggat acaggggtga agtttctgtg tgagggcttg agttaccctg attgtaaact
2701 gcagaccttg gtgttacagc aatgcagcat aaccaagctt ggctgtagat acctctcaga
2761 ggcgctccaa gaagcctgca gcctcacaaa cctggacttg agtatcaacc agatagctcg
2821 tggattgtgg attctctgtc aggcgttaga gaatccaaac tgtaacctaa acacctacg
2881 gttgaagacc tatgaaacta atttggaaat caagaagctg ttggaggaag tgaaagaaaa
2941 gaatcccaag ctgactattg attgcaatgc ttccggggca acggcacctc cgtgctgtga
3001 ctttttttgc tgagcagcct gggatcgctc tacgaattac acaggaagcg ggattcgggt
3061 ctctaagatg tcttatgaat gcaggtcaga gggtcacatg ttaacactag agtctgtcga
3121 gaggtaggat ttgacactgg ttttctcact atttttggga gattctgcac gagtcacgca
3181 cccccttcac atgacgctat gtactttctc acagggataa taagttaga gcactctcgt
3241 tgcaa
```

Figure 7

Polypeptide sequence of Human NALP7, 980 amino acid isoform (SEQ ID
NO: 3; GenBank accession No. AY154462; Swiss-Prot accession No.
Q8WX94)

```
  1 mtspqlewtl qtlleqlned elksfksllw afpledvlqk tpwseveead gkklaeilvn
 61 tssenwirna tvnileemnl telckmakae mmedgqvqei dnpelgdaee dselakpgek
121 egwrnsmekq slvwkntfwq gdidnfhddv tlrnqrfipf lnprtprklt pytvvlhgpa
181 gvgkttlakk cmldwtdcnl sptlryafyl sckelsrmgp csfaeliskd wpelqddips
241 ilaqaqrilf vvdgldelkv ppgaliqdic gdwekkkpvp vllgsllkrk mlpraallvt
301 trpralrdlq llaqqpiyvr vegfleedrr ayflrhfgde dqamrafelm rsnaalfqlg
361 sapavcwivc ttlklqmekg edpvptcltr tglflrflcs rfpqgaqlrg alrtlsllaa
421 qglwaqmsvf hredlerlgv qesdlrlfld gdilrqdrvs kgcysfihls fqqfltalfy
481 alekeegedr dghawdigdv qkllsgeerl knpdliqvgh flfglanekr akeleatfgc
541 rmspdikqel lqckahlhan kplsvtdlke vlgclyesqe eelakvvvap fkeisihltn
601 tsevmhcsfs lkhcqdlqkl slqvakgvfl enymdfeldi eferctylti pnwarqdlrs
661 lrlwtdfcsl fssnsnlkfl evkqsflsds svrilcdhvt rstchlqkve iknvtpdtay
721 rdfclafigk ktlthltlag hiewertmml mlcdllrnhk cnlqylrlgg hcatpeqwae
781 ffyvlkanqs lkhlrlsanv lldegamlly ktmtrpkhfl qmlslencrl teasckdlaa
841 vlvvskklth lclaknpigd tgvkflcegl sypdcklqtl vlqqcsitkl gcrylsealq
901 eacsltnldl sinqiarglw ilcqalenpn cnlkhlrlkt yetnleikkl leevkeknpk
961 ltidcnasga tappccdffc
```

Figure 7 : continued

DNA Sequence of Human NALP7, 1009 amino acid isoform (SEQ ID NO: 4;
GenBank accession No. NM_139176)

```
   1 caggctggaa gcaagacctg acctgaggga gttcttcagc cttaacctaa ggtctcatac
  61 tcggagcact atgacatcgc cccagctaga gtggactctg cagaccttc tggagcagct
 121 gaacgaggat gaattaaaga gtttcaaatc ccttttatgg gcttttcccc tcgaagacgt
 181 gctacagaag accccatggt ctgaggtgga agaggctgat ggcaagaaac tggcagaaat
 241 tctggtcaac acctcctcag aaaattggat aaggaatgcg actgtgaaca tcttggaaga
 301 gatgaatctc acggaattgt gtaagatggc aaaggctgag atgatggagg acggacaggt
 361 gcaagaaata gataatcctg agctgggaga tgcagaagaa gactcggagt tagcaaagcc
 421 aggtgaaaag gaaggatgga gaaattcaat ggagaaacag tcttttggtct ggaagaacac
 481 cttttggcaa ggagacattg acaatttcca tgacgacgtc actctgagaa accaacggtt
 541 cattccattc ttgaatccca gaacacccag gaagctaaca ccttacacgg tggtgctgca
 601 cggccccgca ggcgtgggga aaaccacgct ggccaaaaag tgtatgctgg actggacaga
 661 ctgcaacctc agcccgacgc tcagatacgc gttctacctc agctgcaagg agctcagccg
 721 catgggcccc tgcagttttg cagagctgat ctccaaagac tggcctgaat gcaggatga
 781 cattccaagc atcctagccc aagcacagag aatcctgttc gtggtcgatg ccttgatga
 841 gctgaaagtc ccacctgggg cgctgatcca ggacatctgc ggggactggg agaagaagaa
 901 gccggtgccc gtcctcctgg ggagtttgct gaagaggaag atgttaccca gggcagcctt
 961 gctggtcacc acgcggccca gggcactgag ggacctccag ctcctggcgc agcagccgat
1021 ctacgtaagg gtggagggct tcctggagga ggacaggagg gcctatttcc tgagacactt
1081 tggagacgag gaccaagcca tgcgtgcctt tgagctaatg aggagcaacg cggccctgtt
1141 ccagctgggc tcggccccg cggtgtgctg gattgtgtgc acgactctga agctgcagat
1201 ggagaagggg gaggacccgg tccccacctg cctcacccgc acggggctgt tcctgcgttt
1261 cctctgcagc cggttcccgc agggcgcaca gctgcgggcg gcgctgcgga cgctgagcct
1321 cctggccgcg cagggcctgt gggcgcagat gtccgtgttc accgagagg acctggaaag
1381 gctcggggtg caggagtccg acctccgtct gttcctggac ggagacatcc tccgccagga
1441 cagagtctcc aaaggctgct actccttcat ccacctcagc ttccagcagt ttctcactgc
1501 cctgttctac gccctggaga aggaggaggg ggaggacagg gacggccacg cctgggacat
1561 cggggacgta cagaagctgc tttccggaga agaaagactc aagaaccccg acctgattca
1621 agtaggacac ttcttattcg gcctcgctaa cgagaagaga gccaaggagt tggaggccac
1681 ttttggctgc cggatgtcac cggacatcaa acaggaattg ctgcaatgca agcacatct
1741 tcatgcaaat aagcccttat ccgtgaccga cctgaaggag gtcttgggct gcctgtatga
1801 gtctcaggag gaggagctgg cgaaggtggt ggtggccccg ttcaaggaaa tttctattca
1861 cctgacaaat acttctgaag tgatgcattg ttccttcagc ctgaagcatt gtcaagactt
1921 gcagaaactc tcactgcagg tagcaaaggg ggtgttcctg gagaattaca tggattttga
1981 actggacatt gaatttgaaa gctcaaacag caacctcaag tttctggaag tgaaacaaag
2041 cttcctgagt gactcttctg tgcggattct ttgtgaccac gtaacccgta gcacctgtca
2101 tctgcagaaa gtggagatta aaaacgtcac ccctgacacc gcgtaccggg acttctgtct
2161 tgctttcatt gggaagaaga ccctcacgca cctgaccctg gcagggcaca tcgagtggga
2221 acgcacgatg atgctgatgc tgtgtgacct gctcagaaat cataaatgca acctgcagta
2281 cctgaggttg ggaggtcact gtgccacccc ggagcagtgg gctgaattct tctatgtcct
2341 caaagccaac cagtccctga agcacctgcg tctctcagcc aatgtgctcc tggatgaggg
2401 tgccatgttg ctgtacaaga ccatgacacg cccaaaacac ttcctgcaga tgttgtcgtt
2461 ggaaaactgt cgtcttacag aagccagttg caaggacctt gctgctgtct tggttgtcag
2521 caagaagctg acacacctgt gcttggccaa gaaccccatt ggggatacag gggtgaagtt
2581 tctgtgtgag ggctgagtt accctgattg taaactgcag accttggtgt tacagcaatg
2641 cagcataacc aagcttgact gtagatatct ctcagaggcg ctccaagaag cctgcagcct
2701 cacaaacctg gacttgagta tcaaccagat agctcgtgga ttgtggattc tctgtcaggc
2761 attagagaat ccaaactgta acctaaaaca cctacgcctc tggagctgct ccctcatgcc
2821 tttctattgt cagcatcttg gatctgctct cctcagcaat cagaagcttg aaactctgga
2881 cctgggccag aatcatttgt ggaagagtgg cataattaag ctctttgggg ttctaagaca
2941 aagaactgga tccttgaaga tactcaggtt gaagacctat gaaactaatt tggaaatcaa
3001 gaagctgttg gaggaagtga agaaaagaa tccaagctg actattgatt gcaatgcttc
3061 cggggcaacg gcacctccgt gctgtgactt ttttgctga gcagcctggg atcgctctac
3121 gaattacaca ggaagcggga ttcgggtctc taagatgtct tatgaatgca ggtcagaggg
3181 tcacatgtta acactagagt ctgtcgagag gtaggatttg acactggttt tctcactatt
3241 tttgggagat tctgcacgag tcacgcaccc ccttcacatg acgctatgta ctttctcaca
3301 gggataataa agttagagca ctctcgttgc a
```

Figure 8

Polypeptide of Human NALP7, 1009 amino acid isoform (SEQ ID NO: 5; GenBank accession No. NM_139176, DAA01246.1)

```
  1 mtspqlewtl qtlleqlned elksfksllw afpledvlqk tpwseveead geklaeilvn
 61 tssenwirna tvnileemnl telckmakae mmedgqvqei dnpelgdaee dselakpgek
121 egwrnsmekq slvwkntfwq gdidnfhddv tlrnqrfipf lnprtprklt pytvvlhgpa
181 gvgkttlakk cmldwtdcnl sptlryafyl sckelsrmgp csfaeliskd wpelqddips
241 ilaqaqrilf vvdgldelkv ppgaliqdic gdwekkkpvp vllgsllkrk mlpraallvt
301 trpralrdlq llaqqpiyvr vegfleedrr ayflrhfgde dqamrafelm rsnaalfqlg
361 sapavcwivc ttlklqmekg edpvptcltr tglflrflcs rfpqgaqlrg alrtlsllaa
421 qglwaqmsvf hredlerlgv qesdlrlfld gdilrqdrvs kgcysfihls fqqfltalfy
481 alekeegedr dghawdigdv qkllsgeerl knpdliqvgh flfglanekr akeleatfgc
541 rmspdikqel lqckahlhan kplsvtdlke vlgclyesqe eelakvvvap fkeisihltn
601 tsevmhcsfs lkhcqdlqkl slqvakgvfl enymdfeldi efessnsnlk flevkqsfls
661 dssvrilcdh vtrstchlqk veiknvtpdt ayrdfclafi gkktlthltl aghiewertm
721 mlmlcdllrn hkcnlqylrl gghcatpeqw aeffyvlkan qslkhlrlsa nvlldegaml
781 lyktmtrpkh flqmlslenc rlteasckdl aavlvvskkl thlclaknpi gdtgvkflce
841 glsypdcklq tlvlqqcsit klgcrylsea lqeacsltnl dlsinqiarg lwilcqalen
901 pncnlkhlrl wscslmpfyc qhlgsallsn qkletldlgq nhlwksgiik lfgvlrqrtg
961 slkilrlkty etnleikkll eevkeknpkl tidcnasgat appccdffc
```

Figure 8 : continued

SEQUENCE LISTING

```
<160> NUMBER OF SEQ ID NOS: 44

<210> SEQ ID NO 1
<211> LENGTH: 18242
<212> TYPE: DNA
<213> ORGANISM: Homo sapiens

<400> SEQUENCE: 1
ttcttcagcc ttaacctaag gtctcatact cggagcacta tgacatcgcc ccagctagag      60
tggactctgc agacccttct ggagcagctg aacgaggatg aattaaagag tttcaaatcc     120
cttttatggg cttttcccct cgaagacgtg ctacagaaga ccccatggtc tgaggtggaa     180
gaggctgatg gcaagaaact ggcagaaatt ctggtcaaca cctcctcaga aaattggata     240
aggaatgcga ctgtgaacat cttggaagag atgaatctca cggaattgtg taagatggca     300
aaggctgaga tgatgggtaa gtagaacctg gggtgtcctg gtcattttt tttttttttt      360 ttttttttg agatggagtc tcgttctgtc gcccaggctg gagtgtaagg ctggagtgca     420
gtggcgagat ctgggctcac tgcaacctcc gcctctgggt tcaagtgatt ctcctatctc     480
agcctccgga gtagctggga ttacaggcgt gtttcaccac acctggctaa tttttttttt     540
tttgtatttt tagtagagat ggggtttgc catgttggcc aggctggtct tgatctcctg     600
accttgtgat ccgcccacct cagccttcca aagtgctgtg attacaggca tgagccacca     660
tgcctggctg acactttatg tacaataatg tctgatttac gaagtgtaaa ttactgtgtc     720
aggcttacat ctaagtattt tacagaggac ggacaggtgc aagaaataga taatcctgag     780
```

-continued

```
ctgggagatg cagaagaaga ctcggagtta gcaaagccag gtgggtaaat acggtcctat    840
ggtcatgagt ttggtgtttg agagcatgca aggtgcatca cttcttcctg gttttattca    900
tttctggtag tttttttttt ttttgagacg gaatcttgct ctgtagccca ggctggagtg    960
tagtggctcc gtctctgctc attgcaacct ctgcctcccg ggttcaagca attctctgcc   1020
tcagcctcct gagtagccgg gattacaggc ggccgccact accccagct aatgttttgt    1080
atttttagta gagatggggt ttcactatct tggccaggct ggtcttgaac tcctgacctc   1140
aagtgatcca cccaccttgg cctcccaaag tgccgggatt acaagcatga cacccgtgc    1200
ctggccctca tttctggtac ttgacaaaat aattcagaaa atcatcatca tcaacctcaa   1260
ctgtcctatg ggctgtcact gcaggtgaaa aggaaggatg agaaattca atggagaaac    1320
agtctttggt ctggaagaac accttttggc aaggagacat tgacaatttc catgacgacg   1380
tcactctgag aaaccaacgg ttcattccat tcttgaatcc cagaacaccc aggaagctaa   1440
caccttacac ggtggtgctg cacgccccg caggcgtggg gaaaaccacg ctggccaaaa    1500
agtgtatgct ggactggaca gactgcaacc tcagcccgac gctcagatac gcgttctacc   1560
tcagctgcaa ggagctcagc cgcatgggcc cctgcagttt tgcagagctg atctccaaag   1620
actggcctga attgcaggat gacattccaa gcatcctagc caagcacag agaatcctgt    1680
tcgtggtcga tggccttgat gagctgaaag tcccacctgg ggcgctgatc caggacatct   1740
gcggggactg ggagaagaag aagccggtgc ccgtcctcct ggggagtttg ctgaagagga   1800
agatgttacc cagggcagcc ttgctggtca ccacgcggcc cagggcactg agggacctcc   1860
agctcctggc gcagcagccg atctacgtaa gggtggaggg cttcctggag gaggacagga   1920
gggcctattt cctgagacac tttggagacg aggaccaagc catgcgtgcc tttgagctaa   1980
tgaggagcaa cgcggccctg ttccagctgg gctcggcccc cgcggtgtgc tggattgtgt   2040
gcacgactct gaagctgcag atggagaagg gggaggaccc ggtccccacc tgcctcaccc   2100
gcacgggct gttcctgcgt ttcctctgca gccggttccc gcaggcgca cagctgcggg    2160
gcgcgctgcg gacgctgagc ctcctggccg cgcagggcct gtgggcgcag atgtccgtgt   2220
tccaccgaga ggacctggaa aggctcgggg tgcaggagtc cgacctccgt ctgttcctgg   2280
acggagacat cctccgccag gacagagtct ccaaaggctg ctactccttc atccacctca   2340
gcttccagca gtttctcact gccctgttct acgccctgga gaaggaggag ggggaggaca   2400
gggacggcca cgcctgggac atcggggacg tacagaagct gctttccgga gaagaaagac   2460
tcaagaaccc cgacctgatt caagtaggac acttcttatt cggcctcgct aacgagaaga   2520
gagccaagga gttggaggcc acttttggct gccggatgtc accggacatc aaacaggaat   2580
tgctgcaatg caaagcacat cttcatgcaa ataagccctt atccgtgacc gacctgaagg   2640
aggtcttggg ctgcctgtat gagtctcagg aggaggagct ggcgaaggtg gtggtggccc   2700
cgttcaagga aatttctatt cacctgacaa atacttctga agtgatgcat gttccttca    2760
gcctgaagca ttgtcaagac ttgcagaaac tctcactgca ggtagcaaag ggggtgttcc   2820
tggagaatta catggatttt gaactggaca ttgaatttga aggtaagaa ctgttttccc    2880
atcccacgct ccactaggaa gaggccagcg tctcctttgc cctgtcgctt actgtcagaa   2940
tttccctctg gctggacttc tttccagctt catgttcaac gtggagacac gacttggcaa   3000
ttaggaattg gggcttttta tttttgagac ggagtctcgc tctgtccccc aggctggagt   3060
gcagtggcgc gatcttggct cactgcaacc tccgcctccc gggttcaagt gattctcctg   3120
cctcagcctc ccgagtagct gggactatgg gcgtgcacca ccttgcccgg ttaattattt   3180
```

```
tatttttttg tagagatggg ggtctcagtt tctagcccaa gttggtctta aactcctggg    3240
ctcaagtgat cttcccactt tggcctagca aagtgttggg attacaggca tgagccacct    3300
cactcagcct tatctattat tttatttttt ttgtaaaact taagatctat actggtagca    3360
aagcatgtga tgcaatattg tttactatag acactgtttt aggttggtgc aaaagtaatt    3420 gtggttttg ccattgaaat gtggtttgca gatgcccatc tcaccatgca ggtactagtc     3480
ctaagagatg aacgtgtgtt ctcctgcagg tgcacttacc taaccattcc gaactgggct    3540
cggcaggatc ttcgctctct tcgcctctgg acagatttct gctctctctt cagctcaaac    3600
agcaacctca gtttctgga agtgaaacaa agcttcctga gtgactcttc tgtgcggatt     3660
ctttgtgacc acgtaacccg tagcacctgt catctgcaga aagtggagta agtagaagct    3720
catcttgcaa ggaagaccct gaacgatgac taagcttctt gtacttttgt tttttaaatt    3780
tggaaatgtg ctgtttcatc tccatgtatt tggggatttt ccagctgtct tttttttttt    3840
tttttttttt ggtgagacgg agatttactc ttgttgccca ggctggagtg caatggcgcg    3900
atctcagctc actgcatcct ccacctccca ggttcaagca attctcctgc ctcagcctcc    3960
cgagtagctg ggattacagg catgtgccac cttgcccggc taattttgta cttttagcac    4020
agacaggttt tcaccgtgtt gcccaggctg atctcgagct cctgacctca ggtgatttgc    4080
ctgcctcggc cttccaaagt gctgggatta taggcatgag ccgctgcacc tggccccttt    4140 tttattttt attttttctg agacagagtt tcactctgtc acctaggcgc tggagtgcaa    4200
tgacttaatc ttgtgttttt agtagaggtg aatttctc catcttggcc aggcttgtct     4260
cgaactcctg acctaaggtg atgcgcctgc ctcggtcttc gaaagtgctg ggattacagg    4320
catgagccac catgcctggc cccagctatc ttttttttgg tttgttttgt taccaaaaca    4380
aaccaaaaag taggtacaag tacaggttag ttacacaggt aaccgtgtgt cataggagtt    4440
tgttgtacag attattttgt cacccaagta ttaagcctag tacccttag ttgttttcc     4500 tgatcctctg cttcttgact tttttttttt ttttgagac agtctcgcta tgttccccag    4560
gctggagtgc agtgcagcaa tctcggctca ctgcaagccc tgcctccgg gttcatgcca    4620 ttctcctgcc tcagcctccc gagtagctgg gactacaggc gccgccacc acgcccggct   4680 agttttttgt aattttagta aagacggggt ttcaccgtgt tagccaggat ggtcttgatc    4740
tcctgacctc gtgatccacc cgcctcggcc tcggcctccc aaagtgctgg gattacaggc    4800
gtgagccacc acaccggcg aattttttt tcttttgaga tggagtcttg ctctgttgcc     4860
caggctggag tgcagtggtg cggtctcggc tcactgcaac ctctgcctcc tggattcaag    4920
tgattctcct acctcagcct cccgaatacc tgggactaca agcatgcccc tccatgtgca    4980
gctaattttt gtatttttag tagagacggg gcttccccat gttggccagg ctggtctcga    5040
actcctgacc tcaggcgatc tgcctgcctc ggccccagct aatttatttt ttgtagagat    5100
ggagtttcac catgttgccc aggttggtct cagactcctg acctcaggtt atcctcctgc    5160
ctcagcctcc caaagtgctg gggttacaga cacgagccac tgcacccggc caagaacttc    5220
taataatttc taaatgtgaa acagcttttt gtttatacat gcctccacac aatgtgagta    5280
ttaatcactc caagtggaat ctcttctgct tttccctagg attaaaaacg tcacccctga    5340
caccgcgtac cggacttct gtcttgcttt cattgggaag aagaccctca cgcacctgac     5400
cctggcaggg cacatcgagt gggaacgcac gatgatgctg atgctgtgtg acctgctcag    5460
aaatcataaa tgcaacctgc agtacctgag gtgggtctca cggtcacggc tctccccagc    5520
acctggagtc cactgcaccg tgttgctggg ggatctagga aaagggtaa ccactccaga     5580
```

```
tgccgtccca gacagggaat gtattcctca acaggcctg tgtgggggag tcggcctctc    5640
ctctttcccc caccagcttg tcttctgtgt tgcataacca gctatccatg caaagaaaca    5700
ccccgaattc tgtgctgggt tccagcttta gggacatgct attcctgact gcaccttgcc    5760
taattgttgg gattgagagc agtggccccc agccttttct gcaccgcggg ccggttttgc    5820
acaagacagt ttttccaca gacgggtttg ggggtagttt tgggatgaaa ctgttcgatc    5880
tcagatcagg cacaggagct aatcgttggt gcctgatcct atggagtgca tgatcctcgc    5940
actttgggag cctgaggaga atggatcatc aatctcagat catcaggagt taggtattca    6000
taaggagcat gcaaccttct ctgcactcaa tgagaatctt tttttttttt tttttcttt    6060
gagacagttt tattcttgtc acccaggctg gagcgcagtg gcgcgatctc gttcactgca    6120
acctccgcct cctgggttca gcagttctg cctcagcttc ccgagtagct ggggttacag    6180
gcgtgcacca ccacgcctgg caaatgtttg tattttttaat agagacaggg tttcaccatg    6240
ttggccaggc tggtctcgaa ctcctgacct caagtgatcc gcctgtctcg gcctcccaaa    6300
gtgctaggat tacaggcatg aaccactgcg cctggccagg ataaaatttt tattttgagt    6360
attaagcatc aatttgcccc ttctagtccc agctacagtg gatgctgagg tgggaggatc    6420
atttgagccc aggagacagg ttgtggtgac ctgtgatcat gccactgcac tccagcctgg    6480
gcaacagagc gagatcctgt ctcaaaaaaa aattttttt ttcccccctg caaaatcatc    6540
cacacaggcc gttttggtga acattgcac agaattgtat tacaatctct tggagaagtg    6600
gctggatgtt accctaatgg ccatgggat acttgaagaa gcagaggcaa cattagatct    6660
ctccagtaat tcaggccagg gttggaggca tgagtagaat gagataaacc aaagacataa    6720
tgtcttggga agtgaagcag aagaagctga tctgggccag gcgcggtggc tcacacctgt    6780
aatcccagta cttcggtagg ccaaggtggg tggatcacct gaggtcagga gttcaagacc    6840
agtgtggcca acatggtgaa atcccgtctc tactaaaaat acaaaaattg gcgaatgcct    6900
gtaatcccag ctacttcgga ggctgaggca ggagaatagc ttgaacccgg gaggcggagg    6960
ctgcagtgag gtgagatcac gcctttgcat tccagactgg gcaacagagt gaaactctgt    7020
ctcaaaaaaa aaaagctgat agggtatact ctgtcctccc agaagaatga cttttcccac    7080
tcttttcaca ggttgggagg tcactgtgcc accccggagc agtgggctga attcttctat    7140
gtcctcaaag ccaaccagtc cctgaagcac ctgcgtctct cagccaatgt gctcctggat    7200
gagggtgcca tgttgctgta caagaccatg acacgcccaa acacttcct gcagatgttg    7260
tcgtaagtct cctcttccca tgggcagctc tggtttagtt ctgggctat agaagagaaa    7320
gggtaacacc tgacttactg cgccacccac gtggcgcctc ttgctgaaat aaacacctgc    7380
ttcaggcccg gcacggtggc tcctgcctgt aatctcagca gagaggtggg cggatcatct    7440
gagttcagga gttcgagacc aacctggcca acatggtgaa accctgtttc tattaaaaat    7500
accaaaaaca ggccgggtgc ggtggctcat gcctgtaatc ccagcacgtt gggaggccaa    7560
ggcggggaga tcacgaggtc aagagatcga gaccatcctg gctaacatgg tgaaacccccg    7620
tctctactaa aaatacaaaa aaattatcca ggtgtggtgg gcgcctgtag tcccagctac    7680
tcaggaggct gagtcagcag aatggtgtaa acctgggagg cggcgattgg cagtgaaccg    7740
agatcgcgcc actgcactcc agcctgggcg acagagcgag actccgtctc aaaaacaaca    7800
cctgtgtcct gtgatggctc caggtggacc gctgcatctt ggccttctcg ccttcctgct    7860
cttttgtggc catgatgact cccacaggac agagggcagg ggatgaacag gaagggctga    7920
agctgagtac cctagcatgt ggacatcact gagcaggttg gagttgtgga aatgttctca    7980
```

```
tccttctacc atttgtttca tattttttgca ggttggaaaa ctgtcgtctt acagaagcca   8040
gttgcaagga ccttgctgct gtcttggttg tcagcaagaa gctgacacac ctgtgcttgg   8100
ccaagaaccc cattggggat acaggggtga agtttctgtg tgagggcttg agttaccctg   8160
attgtaaact gcagaccttg gtgtaagtcc ctgctgggtg tgtgtgtgtg tgcacatgaa   8220
ttcaagcagg agagacatga aagtacttgt taattcattt caaatgtaac ttttaaaaac   8280
ctggtaagaa ttaaagaaca ggcagaggcc aggcgtggtg gctcatgcct gtaatcccag   8340
cactttggga ggccgaggcg ggtggatcat gaggtcagga gatggagacc atcctggtta   8400
acatggtgaa accctgtctg tactaaaaat accaaaaatt agccaggtgt ggtggcggat   8460
gcctgtagtc ccagctactt gggaggatga acaggagaa tggcgtgaac ctggaaggcg   8520
gaggttgcag tgagccgaga tcgcaccact gcactccagc ctgggcgaca gaacaagact   8580
ccttctcaaa aaacaaaga aacaaaaaaa accaggcaga tacaggtaga aacatgttaa   8640
tatttgcatg tcagcagagc ctcttcctgc tatgaaggaa gatttgagat gagtagttgg   8700
ttctcggatc tgatgctttg tgtgtgttct ttcaaattcc tatgacatag tactgcctgc   8760
tattggaggt agattgagtt atgtggtagg gccagtggca cctttttta aacttttatt   8820
tccataggtt attggggaac aggtggtgaa tggtgggcag atcacctaag gttcgagacc   8880
agcctggcca acatggtgaa aacccatcgc tactaaaaaa tacaaaaatt aaccaggctt   8940
ggtggtgcgt gcctatagta ccagctactc agaaggctga ggtaggagaa tcgcttgaat   9000
ctggaggca gaggctgcag tgagctgaga tggcgccact gcactccagc ccgggcgaca   9060
gagtgagact ccgtctcaag aaaaaaacaa aaaaaaactc aacaaaaatc cttatttgta   9120
aaagacatag gtggcaggtt ggaattgacc cacgaactat agttggctga atcttgttat   9180
atggaaagaa gcccagcgtg agctacctgt tcacattaaa attatggtta gaaaatatt   9240
caagagattg catagggttg aagacctgtt cctgttcaga aattctagct agtggtcatt   9300
tctgagattc attttttttt ttttggatga agtctcactc tgtcgcccag actggaatgc   9360
agtggtgtaa tcttggctga ctgcaacttc tgcctcccag gttcaagcga ttctcctgcc   9420
tcagcctccc aagtagctgg gattacaggt gccctccacc atgcctggct aatttttgca   9480
cttttagtgg agatgaggtt tcaccatgtt ggccaggctg gtcttgaact cctggcctta   9540
agtgatctgc ctgcctcggc ctcccaaagt gctggcgttc caggcatgag ccactgtgcc   9600
tggcttagaa taactattgt taaacaaaca gtcacctacc tgatcgttat acgaagtgta   9660
cctgcaccaa aacatcacac tatacccta tatatgaga atgtgtcagt taagacaaa   9720
acttaaacat gaaataaaat gacagggaaa gtgaaatttc cataatctaa ccacgcagaa   9780
aataagtgac ccagggctca gatcctgtcc tgggtcggtc tgaacccaga gcctaagctg   9840
ttgtcccagg cagagctgga aatggatgga atcagaaggc catttggatg tttttttttt   9900
tttttaaca gtctctctct gtcaccaggc tggagtgcag tggtgcgatc ttggctcact   9960
gcaacctccg cttcctgggt tcaagtaatt ctcctacctc agcctcctga gtagctagga  10020
ttacaggcat gggccgccac acctggctaa tttttttttt tttttgagat ggagtttcgc  10080
tcttgcccag gctggagtgc aatggtgcaa tctctgctca ccacaacctc cgtctcccca  10140
gttcaagaga ttctcctgcc tcagcctcct gagtagctgg gattacaggc atgtgccacc  10200
acacctggct aatttttgtat ttttagtaga acgggtttc tccatattgc ttaggctggt  10260
cttgaactcc cgacctcagg tgatctgtct gcctcagcct cccaaagtgc tgagattaca  10320
ggtgtgagcc atcgtgccca gctaattttt gtatttagta aagatggggt ttcaccactt  10380
```

```
tggccaggct ggtcttgaac tcctgatctt gtgattcacc caccttggtc tcccaaagtg   10440
ctgagattac aggtttgagc caccgcgccc ggcccgattt tgtattttt tagtagagat    10500 ggggttttcac catgttggcc aggctggtct tgaactcctg acctcaaatg atctgcccgt  10560
cttggcctcc cactgctgtg attataggcg tgagccactg tgcccggccc atttgcatgc   10620
ttttatgtgc aagcccacct ggaagtatat agctccagtt catgggtcaa ttcctacctg   10680
ccacctatgt tttatataaa tactttttgt tgttgttgtt gttttcttga gacggagtct   10740
cgctctgtcg cccgggctgg agtgcagtgg cgcgatctca gctcactgca gcctctgcct   10800
cccggattca agcgattctc ctgcctcagt cttctgagta gctggcacta caggcgtgca   10860
ccaccaagtc tggttatata ggtggcgggc acctataatc ccagctactt gggaggctga   10920
ggcagaagaa tcgcttgaac ctgggaggca gaggttgcag tgagccaaga gtgcagcact   10980
gcattccagt atataagtgg aaggtatata gtgttggaaa taactgcttc acagggcgtt   11040
agccagaggg ataacaggct tctcttcctt tgattatcct gtaggttaca gcaatgcagc   11100
ataaccaagc ttggctgtag atatctctca gaggcgctcc aagaagcctg cagcctcaca   11160
aacctggact tgagtatcaa ccagatagct cgtggattgt ggattctctg tcaggcatta   11220
gagaatccaa actgtaacct aaaacaccta cggtaggcga ttttctttt cttctttctt    11280 tcttttttg agacagggtc ttgctctgtc ccccagcctg gagtgcagtg gggtgattac    11340
ggctcactgc ggcttcggtc ttccaggctt gatcggttct cccacctcag cctcctgagt   11400
agctggctct acaggcatgt attaccatgg ccaggtaact gttttctgta gagatgaggt   11460
cttgtcatct ttcccgggct ggttttgaat tctggtgctc aaggaatcct cccacctcgg   11520
cctcccaatg tgctaggatt acaggcatga gccatcatgc ctggcctcat ttttaaagtg   11580
tttggaaatc tggaaatcct taatttctat gttttctttt ttttttttt tttttgagac    11640 ggagcctcgt tctagttgcc caggctgag tgcagtggcg cgatctcggc ttactgcaac    11700
ctcttcctcc cgggttctcg ctattctcct gcctcagcct cctgagtagc tgggactaca   11760
gatgcccgcc accgtgcctg gctaattttt tttgtatttt tagtagagat gggttttcaca  11820 gtgttagcca ggatggtctc gatctcctga cctcatgatc tgcccgcctt ggccttccaa   11880
agtgctggga ttacaggcgt gagccaccac gcccggccaa tttctatgtt ttcaatatct   11940
cagactgtat cacttcggat ccagttttaa gatcaaaccc ctccagaaac tgaatatatg   12000
tgggtgggca cttctaaagt caggtagagg gcctggagaa gtgaaatata taacaatg     12060 gcccccagtg acctggactt cagcagcatg ctgcttctgc tgggatccag taatcaggaa   12120
gcagtgagcc tgccccacct cataaaccca gggaaccata ggtgggatac cacccccaga   12180
aaatgcaaag tctccacaaa tggaatgcg agctcttcat cacttctctc cccaaagttt    12240
gtcagttgca tctcttggat gcaacctatt ttccaactag aatctgcaat cctaatgcaa   12300
agagaatctg cacgtcatta ctacttagct ttgctgtaga gtaaagaaaa aaacactag    12360 aacacagggt actttttttc tttttcaga cagagtctcg ctttgtcacc caggctggag    12420
tgcagtggtc cgatcttggc tcactgcaac ctcagcctcc aaggttcaag cgattctcct   12480
gattgagctg agtagttggg attacaggcg tgcaccacca tacccagcta atttttgtat   12540
ttttagtaga gaccaggttt caccatgtta gccagactgg tctcaaactc ctgacctcaa   12600
gtgatccacc tgcctcaacc tcccaaagtg ctgggattac aggcatgagc caccattcct   12660
ggcctcctga gtttcttaa cccatccccc tgaggaatat ttcaagcctc aagccagacc    12720 gtgataccctt tatttccaaa gactcaaaag ctcaatgcaa acgggtggat tacctggtgt   12780
```

```
cttgttcctg taatctcagc tatgactgta atcctagatt ctcgggaggc tggggcagga    12840
gaatcgcttg aacccaggag gcggaggttg cagtgagccg agatcacgcc attgcactcc    12900
agccttggca acaagagtga aactctgcct taaaaaaaac aaaaccaaag gcttctacag    12960
tggcctacag ggcctatggg gggatcctcg tgtaagttat gagccataaa tcattctact    13020
ttctcactag ctcagtattt tatttacaag attccctccc ccagttagca tgctggttca    13080
tgatctacca tccttcagtt tctttcctca tatcactttc caaaagagga cttaaatgac    13140
cagcataagt ctagccaatc aatgcctctc tgtttgactt acctctaccc tgtttatttt    13200
aataccatca tccattgtct tcaatagaac atatcgagat gtctgctgtc actaaaaact    13260
ctgaggacaa ggatttcttc tgctcactcc cctctgcctt tcctcactac tggagcccca    13320
gcaaatatgc tgcttgtttt tttgttttgt tttgttgag accaagtctc actcttcac     13380 ccaagctgga atgcagtggt gatatgttgg ctaactacaa cctctgcctc ctggttcagg    13440
cgattctcct gcctctcgag tagctggaat tataggtggt tccaccatac ctggctaatt    13500
tttgtatttt cattttatgt tatatatttg tgagatggag tctcattcta ttgcccaggc    13560
tggagtgcag tggcgcaatc tgggctcact gtaacctccg cctcccaggc tgaagcgatt    13620
cttgtgcctc agcctcccaa gtagctagca ttaaaggcac acaccaccat gcatggctaa    13680 tttttttgtag agatggggtt ttgccatgtt ggcctggctg gtctcgaact cctgacctca    13740
ggtgatctac cctcctcggc ctcccaaggt gctgggccta caggtgtctg tccccacgcc    13800
ctgcctaatc tttgtatttt tagtagagat ggggtttgac cgtgttggca aggctggtct    13860
cgaacacctg gcctcaagtg atccacccgc cttggcctcc cgaagtgttg ggattacacg    13920
cttgagccac tacctgctca gtgaatgcgt ggatttccat gttcttcctc aacagcctct    13980
ggagctgctc cctcatgcct ttctattgtc agcatcttgg atctgctctc ctcagcaatc    14040
agaagcttga aactctggac ctgggccaga atcatttgtg gaagagtggc ataattaagc    14100
tctttggggt tctaagacaa agaactggat ccttgaagat actcaggtat gggtttttg    14160 ttttgttttg ttttgttttt tgttttgtt tttttgagat ggagtcgtgc tctgtcattc    14220
aggctggagt gcagtggcgc aatcttggct caccgcaacc tctgcctctc aggttcaagc    14280
aattctcctg cctcagcctc atgagtagct gggcctagag gcatgccaac atgtccagct    14340
aatttttttc ttttctttt ttttttttg agacggagtt ttgttcttgt agcccaggct    14400
ggagtgcagt ggtgcgatct tggctcactg caaccccac ctcctgggtt caagcgattc    14460
tcccaccttg gcctcccaag tagctggaat tacagatgcc tgccaccatg cctggctaat    14520
tttttagtag agaggggttt caccatgttg gccaggctag tcttgaactc ctgacctcag    14580
gtgagccacc tgcctcggcc tcccaaagtg gtgggattac agaggtgagc cattgcaccc    14640 ggccttttg gttttgctt tttgggatgg agtctcactg ttgcccaggc tggagtgcag    14700
tggcgcgatc ttgactcact gcagcctcct tctcacaggt tgaagcgatt tcctgcctc    14760 aacctcctga gtagctggga ttacaggtac acaccaccac agctggctaa tttttttttt    14820 ttttttttt tttaaagac agagtctctc tctgtccccc aggctggagt gcagtggcgc    14880
tatctcggct cagtgcaacc tctgcctcct gggttcaagt gattctcctg cctcagcctc    14940
ctgagtagct aggattacag tcgctcgcca ccacacccag ctaattttg tatttttagt    15000 agagatgggg ttttgccatg ttggccaggc tggtctcgag ctcctgacct caggtgatct    15060
tctcgccttg gcctcccaaa gtgctgggat tacaggcatg agccactgca cctggccaat    15120
ttttgtagtt tttagtagag atgggtttc accatgttgg tcaggttggt ctcaaactcc    15180
```

```
caacctcagg tgatccacct gcctcagcct ctcaaagtgc cgggattaca ggcgtgagcc   15240
actgtgctcg gccctgggat ggctgtttca catggtgaat ttcccatgca gagaagagtt   15300
ttttgggag tgtgtgtact ctttgtaggg atcaacttaa ggcatctttc tatagcacac    15360
tcctagctta ggagataatt taaaaattag atacttttct aaaatgctct gtgaattgaa   15420
tattgtccaa ctttccccca aaacacttag tcctaggcat actgagagtt taaatcatcc   15480
tggagtacag actggaagct tgtgtgtatg tgtgtgcatg agcacacaca cacacacaca   15540
cacacccta atcattatat ccaaaaatag gtagttccca gagctgtcct gggtcttagc    15600
ttttcagaag atcgtcctac agatgctccc ttagttgtga cccgtgtata tctttttcaat  15660
gacttatttg tatttttat ttttttttga dacggagtct tttttttgag acggagtctg    15720
tcttttttt tgaatctgtc ttttttttga gacagagact ccagtctctg tcgcccaggc    15780
tggagtgaag cggtgcgatc tcggctcact gcaagctcca cctcccgggt tcacgccatt   15840
ctcctgcctc agcctcccga gcagctggga ctacaggcgc ccgccaccac gcccggctaa   15900
tttttttgtat ttttagtaga gatggggttt cactatgttg gccaggctgg tctcgaattc  15960
ctgacctcag gtgatctgcc cacctcggcc tcccaaagtg ctgggattac aggcgtgagc   16020
caccgcgccc ggcctcagtg acttatttta acgtaatcta cctttagttt cttcttgcct   16080
ttgtctttc ttttctgaga caacgttttg ctctgctgca ctgtgtggcc gtgttgccga    16140
ggttctcaaa ctcctggctt caaacgatcc tcctgtcttg gcctcacaaa gtacccggat   16200
tgcaggcgtg agccactgtg cacagcccac ttgtcttatt caagagttat tttagttgta   16260
gagatgatac gcatgtaaac tgcttcatga tgcccagtgt tgcattattg gaacgctaag   16320
catgtgggag ttatttatat cctgctcaag gtacgatttt tcacacgtct gcagttcaaa   16380
taattgtaac ctctggcata aatgggttaa ggttttaggg gtatatcatg aaacttgagc   16440
taaatagtgt catgcttctc ttgttggtgg gaccgaggtc tgtaatgcca ccaaggacta   16500
ttggtgacaa atctctagcc ccctgtggtc tcttatgtca tatgtttggg gcgtatttct   16560
tttctcattc ctcagttcct cctttgggag gccaaggtgg gaggattgtt tgaggccagg   16620
agtttgagac cagcctgggc aacatagcaa gccagtgtct ccacaatcac caccccctcat 16680
gttcacatac acaggcttgc atgctgcagc cacgttagag ccaagtttgc tatcattaac   16740
cctggggttc actctggcat tctccttagtt ctactgaagg tttgatttgc cactattttt  16800
tatttattta tttggaggca gagtctcgct ctgtcacccg ggctgcagta cagtggtgcg   16860
gtattggctc actgcaacat ctgcctccca ggttcaaagc gattctcctg tctcagcctc   16920
ctgagtagct ggtattacag ttgtctgcca ccatgcccag ctaattttg tattttagt    16980
agagacgggg tttcactatg ttggccaggc tggtctcgaa ttcctgacct caggtgatct   17040
gcccgcctcg gcctcccaaa gtgctggaat tataggcgtg agtcaccgtg caccagcctg   17100
attatctatt ttttaaattt atttttttaaa ggcatgtttt actctgttac caggctggag   17160
tgcagtaggg caatctctag ctcgttgcaa cctccgcctc ctgggctcaa gtgatcctct   17220
tgcctccgcc tcccgagtag ctgggactat aggcgtgcac caccattcct ggctaacttt   17280
ttctattttt ggtagagaca gggtttcacc gtgttgccca ggctggcctt gaactgcgga   17340
gctcaagcaa tctgcctgcc ttggcctccc aaagtgctgg gactacaggt gcgagacacc   17400
gtgcctggcc ataatctttt tttttcttaga cttataagga tccccattgt gtgggtctaa   17460
atttctttt agaaaacttt tctgactggg tgctgtggct cacatctgta atcccatggc    17520
tttgggaggc cgaggtggat ggatcacttg aggccagaag ttcgagacca gcctggctaa   17580
```

-continued

```
catgtcgaaa ccccatctct actgtaaata caaaacttag ccaagcgtgg tggtgcacac    17640
ctgtaatcac agttactcag gagcctgagg catgagaatt gcttgaactt gggagctgga    17700
ggttgcagag agccaagatg gcaccactgt accccagcct gggcaacaga gcaagaccct    17760 gtccccaga aaatcccaaa aacgtttcct gctttgagtg tttgaaaaca gatattcagg     17820
catcctgggt agttgagaat gaatttctgg gaacatttgt gttctctgat ccctccaggt    17880
tgaagaccta tgaaactaat ttggaaatca agaagctgtt ggaggaagtg aaagaaaaga    17940
atcccaagct gactattgat tgcaatgctt ccggggcaac ggcacctccg tgctgtgact    18000
ttttttgctg agcagcctgg gatcgctcta cgaattacac aggaagcggg attcgggtct    18060
ctaagatgtc ttatgaatgc aggtcagagg gtcacatgtt aacactagag tctgtcgaga    18120
ggtaggattt gacactggtt ttctcactat ttttgggaga ttctgcacga gtcacgcacc    18180
cccttcacat gacgctatgt actttctcac agggataata aagttagagc actctcgttg    18240
ca                                                                  18242
```

```
<210> SEQ ID NO 2
<211> LENGTH: 3245
<212> TYPE: DNA
<213> ORGANISM: Homo sapiens
<220> FEATURE:
<221> NAME/KEY: CDS
<222> LOCATION: (71)..(3013)

<400> SEQUENCE: 2
```

```
caggctggaa gcaagacctg acctgaggga gttcttcagc cttaacctaa ggtctcatac    60
tcggagcact atg aca tcg ccc cag cta gag tgg act ctg cag acc ctt     109
             Met Thr Ser Pro Gln Leu Glu Trp Thr Leu Gln Thr Leu
              1               5                  10 ctg gag cag ctg aac gag gat gaa tta aag agt ttc aaa tcc ctt tta    157
Leu Glu Gln Leu Asn Glu Asp Glu Leu Lys Ser Phe Lys Ser Leu Leu
         15                  20                  25 tgg gct ttt ccc ctc gaa gac gtg cta cag aag acc cca tgg tct gag    205
Trp Ala Phe Pro Leu Glu Asp Val Leu Gln Lys Thr Pro Trp Ser Glu
 30                  35                  40                  45 gtg gaa gag gct gat ggc aag aaa ctg gca gaa att ctg gtc aac acc    253
Val Glu Glu Ala Asp Gly Lys Lys Leu Ala Glu Ile Leu Val Asn Thr
                 50                  55                  60 tcc tca gaa aat tgg ata agg aat gcg act gtg aac atc ttg gaa gag    301
Ser Ser Glu Asn Trp Ile Arg Asn Ala Thr Val Asn Ile Leu Glu Glu
             65                  70                  75 atg aat ctc acg gaa ttg tgt aag atg gca aag gct gag atg atg gag    349
Met Asn Leu Thr Glu Leu Cys Lys Met Ala Lys Ala Glu Met Met Glu
         80                  85                  90 gac gga cag gtg caa gaa ata gat aat cct gag ctg gga gat gca gaa    397
Asp Gly Gln Val Gln Glu Ile Asp Asn Pro Glu Leu Gly Asp Ala Glu
 95                 100                 105 gaa gac tcg gag tta gca aag cca ggt gaa aag gaa gga tgg aga aat    445
Glu Asp Ser Glu Leu Ala Lys Pro Gly Glu Lys Glu Gly Trp Arg Asn
110                 115                 120                 125 tca atg gag aaa cag tct ttg gtc tgg aag aac acc ttt tgg caa gga    493
Ser Met Glu Lys Gln Ser Leu Val Trp Lys Asn Thr Phe Trp Gln Gly
                130                 135                 140 gac att gac aat ttc cat gac gac gtc act ctg aga aac caa cgg ttc    541
Asp Ile Asp Asn Phe His Asp Asp Val Thr Leu Arg Asn Gln Arg Phe
            145                 150                 155 att cca ttc ttg aat ccc aga aca ccc agg aag cta aca cct tac acg    589
Ile Pro Phe Leu Asn Pro Arg Thr Pro Arg Lys Leu Thr Pro Tyr Thr
        160                 165                 170
```

| | | | | | | | | | | | | | | | | |
|---|---|---|---|---|---|---|---|---|---|---|---|---|---|---|---|---|
| gtg | gtg | ctg | cac | ggc | ccc | gca | ggc | gtg | ggg | aaa | acc | acg | ctg | gcc | aaa | 637 |
| Val | Val | Leu | His | Gly | Pro | Ala | Gly | Val | Gly | Lys | Thr | Thr | Leu | Ala | Lys | |
| | 175 | | | | 180 | | | | | 185 | | | | | | |

| | | | | | | | | | | | | | | | | |
|---|---|---|---|---|---|---|---|---|---|---|---|---|---|---|---|---|
| aag | tgt | atg | ctg | gac | tgg | aca | gac | tgc | aac | ctc | agc | ccg | acg | ctc | aga | 685 |
| Lys | Cys | Met | Leu | Asp | Trp | Thr | Asp | Cys | Asn | Leu | Ser | Pro | Thr | Leu | Arg | |
| 190 | | | | | 195 | | | | | 200 | | | | | 205 | |

| | | | | | | | | | | | | | | | | |
|---|---|---|---|---|---|---|---|---|---|---|---|---|---|---|---|---|
| tac | gcg | ttc | tac | ctc | agc | tgc | aag | gag | ctc | agc | cgc | atg | ggc | ccc | tgc | 733 |
| Tyr | Ala | Phe | Tyr | Leu | Ser | Cys | Lys | Glu | Leu | Ser | Arg | Met | Gly | Pro | Cys | |
| | | | | 210 | | | | | 215 | | | | | 220 | | |

| | | | | | | | | | | | | | | | | |
|---|---|---|---|---|---|---|---|---|---|---|---|---|---|---|---|---|
| agt | ttt | gca | gag | ctg | atc | tcc | aaa | gac | tgg | cct | gaa | ttg | cag | gat | gac | 781 |
| Ser | Phe | Ala | Glu | Leu | Ile | Ser | Lys | Asp | Trp | Pro | Glu | Leu | Gln | Asp | Asp | |
| | | | 225 | | | | | 230 | | | | | 235 | | | |

| | | | | | | | | | | | | | | | | |
|---|---|---|---|---|---|---|---|---|---|---|---|---|---|---|---|---|
| att | cca | agc | atc | cta | gcc | caa | gca | cag | aga | atc | ctg | ttc | gtg | gtc | gat | 829 |
| Ile | Pro | Ser | Ile | Leu | Ala | Gln | Ala | Gln | Arg | Ile | Leu | Phe | Val | Val | Asp | |
| | | 240 | | | | | 245 | | | | | 250 | | | | |

| | | | | | | | | | | | | | | | | |
|---|---|---|---|---|---|---|---|---|---|---|---|---|---|---|---|---|
| ggc | ctt | gat | gag | ctg | aaa | gtc | cca | cct | ggg | gcg | ctg | atc | cag | gac | atc | 877 |
| Gly | Leu | Asp | Glu | Leu | Lys | Val | Pro | Pro | Gly | Ala | Leu | Ile | Gln | Asp | Ile | |
| 255 | | | | | 260 | | | | | 265 | | | | | | |

| | | | | | | | | | | | | | | | | |
|---|---|---|---|---|---|---|---|---|---|---|---|---|---|---|---|---|
| tgc | ggg | gac | tgg | gag | aag | aag | aag | ccg | gtg | ccc | gtc | ctc | ctg | ggg | agt | 925 |
| Cys | Gly | Asp | Trp | Glu | Lys | Lys | Lys | Pro | Val | Pro | Val | Leu | Leu | Gly | Ser | |
| 270 | | | | | 275 | | | | | 280 | | | | | 285 | |

| | | | | | | | | | | | | | | | | |
|---|---|---|---|---|---|---|---|---|---|---|---|---|---|---|---|---|
| ttg | ctg | aag | agg | aag | atg | tta | ccc | agg | gca | gcc | ttg | ctg | gtc | acc | acg | 973 |
| Leu | Leu | Lys | Arg | Lys | Met | Leu | Pro | Arg | Ala | Ala | Leu | Leu | Val | Thr | Thr | |
| | | | | 290 | | | | | 295 | | | | | 300 | | |

| | | | | | | | | | | | | | | | | |
|---|---|---|---|---|---|---|---|---|---|---|---|---|---|---|---|---|
| cgg | ccc | agg | gca | ctg | agg | gac | ctc | cag | ctc | ctg | gcg | cag | cag | ccg | atc | 1021 |
| Arg | Pro | Arg | Ala | Leu | Arg | Asp | Leu | Gln | Leu | Leu | Ala | Gln | Gln | Pro | Ile | |
| | | 305 | | | | | 310 | | | | | 315 | | | | |

| | | | | | | | | | | | | | | | | |
|---|---|---|---|---|---|---|---|---|---|---|---|---|---|---|---|---|
| tac | gta | agg | gtg | gag | ggc | ttc | ctg | gag | gag | gac | agg | agg | gcc | tat | ttc | 1069 |
| Tyr | Val | Arg | Val | Glu | Gly | Phe | Leu | Glu | Glu | Asp | Arg | Arg | Ala | Tyr | Phe | |
| | | 320 | | | | | 325 | | | | | 330 | | | | |

| | | | | | | | | | | | | | | | | |
|---|---|---|---|---|---|---|---|---|---|---|---|---|---|---|---|---|
| ctg | aga | cac | ttt | gga | gac | gag | gac | caa | gcc | atg | cgt | gcc | ttt | gag | cta | 1117 |
| Leu | Arg | His | Phe | Gly | Asp | Glu | Asp | Gln | Ala | Met | Arg | Ala | Phe | Glu | Leu | |
| | | 335 | | | | | 340 | | | | | 345 | | | | |

| | | | | | | | | | | | | | | | | |
|---|---|---|---|---|---|---|---|---|---|---|---|---|---|---|---|---|
| atg | agg | agc | aac | gcg | gcc | ctg | ttc | cag | ctg | ggc | tcg | gcc | ccc | gcg | gtg | 1165 |
| Met | Arg | Ser | Asn | Ala | Ala | Leu | Phe | Gln | Leu | Gly | Ser | Ala | Pro | Ala | Val | |
| 350 | | | | | 355 | | | | | 360 | | | | | 365 | |

| | | | | | | | | | | | | | | | | |
|---|---|---|---|---|---|---|---|---|---|---|---|---|---|---|---|---|
| tgc | tgg | att | gtg | tgc | acg | act | ctg | aag | ctg | cag | atg | gag | aag | ggg | gag | 1213 |
| Cys | Trp | Ile | Val | Cys | Thr | Thr | Leu | Lys | Leu | Gln | Met | Glu | Lys | Gly | Glu | |
| | | | | 370 | | | | | 375 | | | | | 380 | | |

| | | | | | | | | | | | | | | | | |
|---|---|---|---|---|---|---|---|---|---|---|---|---|---|---|---|---|
| gac | ccg | gtc | ccc | acc | tgc | ctc | acc | cgc | acg | ggg | ctg | ttc | ctg | cgt | ttc | 1261 |
| Asp | Pro | Val | Pro | Thr | Cys | Leu | Thr | Arg | Thr | Gly | Leu | Phe | Leu | Arg | Phe | |
| | | | 385 | | | | | 390 | | | | | 395 | | | |

| | | | | | | | | | | | | | | | | |
|---|---|---|---|---|---|---|---|---|---|---|---|---|---|---|---|---|
| ctc | tgc | agc | cgg | ttc | ccg | cag | ggc | gca | cag | ctg | cgg | ggc | gcg | ctg | cgg | 1309 |
| Leu | Cys | Ser | Arg | Phe | Pro | Gln | Gly | Ala | Gln | Leu | Arg | Gly | Ala | Leu | Arg | |
| | | | 400 | | | | | 405 | | | | | 410 | | | |

| | | | | | | | | | | | | | | | | |
|---|---|---|---|---|---|---|---|---|---|---|---|---|---|---|---|---|
| acg | ctg | agc | ctc | ctg | gcc | gcg | cag | ggc | ctg | tgg | gcg | cag | atg | tcc | gtg | 1357 |
| Thr | Leu | Ser | Leu | Leu | Ala | Ala | Gln | Gly | Leu | Trp | Ala | Gln | Met | Ser | Val | |
| | | 415 | | | | | 420 | | | | | 425 | | | | |

| | | | | | | | | | | | | | | | | |
|---|---|---|---|---|---|---|---|---|---|---|---|---|---|---|---|---|
| ttc | cac | cga | gag | gac | ctg | gaa | agg | ctc | ggg | gtg | cag | gag | tcc | gac | ctc | 1405 |
| Phe | His | Arg | Glu | Asp | Leu | Glu | Arg | Leu | Gly | Val | Gln | Glu | Ser | Asp | Leu | |
| 430 | | | | | 435 | | | | | 440 | | | | | 445 | |

| | | | | | | | | | | | | | | | | |
|---|---|---|---|---|---|---|---|---|---|---|---|---|---|---|---|---|
| cgt | ctg | ttc | ctg | gac | gga | gac | atc | ctc | cgc | cag | gac | aga | gtc | tcc | aaa | 1453 |
| Arg | Leu | Phe | Leu | Asp | Gly | Asp | Ile | Leu | Arg | Gln | Asp | Arg | Val | Ser | Lys | |
| | | | | 450 | | | | | 455 | | | | | 460 | | |

| | | | | | | | | | | | | | | | | |
|---|---|---|---|---|---|---|---|---|---|---|---|---|---|---|---|---|
| ggc | tgc | tac | tcc | ttc | atc | cac | ctc | agc | ttc | cag | cag | ttt | ctc | act | gcc | 1501 |
| Gly | Cys | Tyr | Ser | Phe | Ile | His | Leu | Ser | Phe | Gln | Gln | Phe | Leu | Thr | Ala | |
| | | | 465 | | | | | 470 | | | | | 475 | | | |

| | | | | | | | | | | | | | | | | |
|---|---|---|---|---|---|---|---|---|---|---|---|---|---|---|---|---|
| ctg | ttc | tac | gcc | ctg | gag | aag | gag | gag | ggg | gag | gac | agg | gac | ggc | cac | 1549 |
| Leu | Phe | Tyr | Ala | Leu | Glu | Lys | Glu | Glu | Gly | Glu | Asp | Arg | Asp | Gly | His | |
| | | | | 480 | | | | | 485 | | | | | 490 | | |

```
gcc tgg gac atc ggg gac gta cag aag ctg ctt tcc gga gaa gaa aga    1597
Ala Trp Asp Ile Gly Asp Val Gln Lys Leu Leu Ser Gly Glu Glu Arg
    495                 500                 505 ctc aag aac ccc gac ctg att caa gta gga cac ttc tta ttc ggc ctc    1645
Leu Lys Asn Pro Asp Leu Ile Gln Val Gly His Phe Leu Phe Gly Leu
510                 515                 520                 525 gct aac gag aag aga gcc aag gag ttg gag gcc act ttt ggc tgc cgg    1693
Ala Asn Glu Lys Arg Ala Lys Glu Leu Glu Ala Thr Phe Gly Cys Arg
                530                 535                 540 atg tca ccg gac atc aaa cag gaa ttg ctg caa tgc aaa gca cat ctt    1741
Met Ser Pro Asp Ile Lys Gln Glu Leu Leu Gln Cys Lys Ala His Leu
            545                 550                 555 cat gca aat aag ccc tta tcc gtg acc gac ctg aag gag gtc ttg ggc    1789
His Ala Asn Lys Pro Leu Ser Val Thr Asp Leu Lys Glu Val Leu Gly
        560                 565                 570 tgc ctg tat gag tct cag gag gag gag ctg gcg aag gtg gtg gtg gcc    1837
Cys Leu Tyr Glu Ser Gln Glu Glu Glu Leu Ala Lys Val Val Val Ala
    575                 580                 585 ccg ttc aag gaa att tct att cac ctg aca aat act tct gaa gtg atg    1885
Pro Phe Lys Glu Ile Ser Ile His Leu Thr Asn Thr Ser Glu Val Met
590                 595                 600                 605 cat tgt tcc ttc agc ctg aag cat tgt caa gac ttg cag aaa ctc tca    1933
His Cys Ser Phe Ser Leu Lys His Cys Gln Asp Leu Gln Lys Leu Ser
                610                 615                 620 ctg cag gta gca aag ggg gtg ttc ctg gag aat tac atg gat ttt gaa    1981
Leu Gln Val Ala Lys Gly Val Phe Leu Glu Asn Tyr Met Asp Phe Glu
            625                 630                 635 ctg gac att gaa ttt gaa agg tgc act tac cta acc att ccg aac tgg    2029
Leu Asp Ile Glu Phe Glu Arg Cys Thr Tyr Leu Thr Ile Pro Asn Trp
        640                 645                 650 gct cgg cag gat ctt cgc tct ctt cgc ctc tgg aca gat ttc tgc tct    2077
Ala Arg Gln Asp Leu Arg Ser Leu Arg Leu Trp Thr Asp Phe Cys Ser
    655                 660                 665 ctc ttc agc tca aac agc aac ctc aag ttt ctg gaa gtg aaa caa agc    2125
Leu Phe Ser Ser Asn Ser Asn Leu Lys Phe Leu Glu Val Lys Gln Ser
670                 675                 680                 685 ttc ctg agt gac tct tct gtg cgg att ctt tgt gac cac gta acc cgt    2173
Phe Leu Ser Asp Ser Ser Val Arg Ile Leu Cys Asp His Val Thr Arg
                690                 695                 700 agc acc tgt cat ctg cag aaa gtg gag att aaa aac gtc acc cct gac    2221
Ser Thr Cys His Leu Gln Lys Val Glu Ile Lys Asn Val Thr Pro Asp
            705                 710                 715 acc gcg tac cgg gac ttc tgt ctt gct ttc att ggg aag aag acc ctc    2269
Thr Ala Tyr Arg Asp Phe Cys Leu Ala Phe Ile Gly Lys Lys Thr Leu
        720                 725                 730 acg cac ctg acc ctg gca ggg cac atc gag tgg gaa cgc acg atg atg    2317
Thr His Leu Thr Leu Ala Gly His Ile Glu Trp Glu Arg Thr Met Met
    735                 740                 745 ctg atg ctg tgt gac ctg ctc aga aat cat aaa tgc aac ctg cag tac    2365
Leu Met Leu Cys Asp Leu Leu Arg Asn His Lys Cys Asn Leu Gln Tyr
750                 755                 760                 765 ctg agg ttg gga ggt cac tgt gcc acc ccg gag cag tgg gct gaa ttc    2413
Leu Arg Leu Gly Gly His Cys Ala Thr Pro Glu Gln Trp Ala Glu Phe
                770                 775                 780 ttc tat gtc ctc aaa gcc aac cag tcc ctg aag cac ctg cgt ctc tca    2461
Phe Tyr Val Leu Lys Ala Asn Gln Ser Leu Lys His Leu Arg Leu Ser
            785                 790                 795 gcc aat gtg ctc ctg gat gag ggt gcc atg ttg ctg tac aag acc atg    2509
Ala Asn Val Leu Leu Asp Glu Gly Ala Met Leu Leu Tyr Lys Thr Met
        800                 805                 810
```

```
aca cgc cca aaa cac ttc ctg cag atg ttg tcg ttg gaa aac tgt cgt      2557
Thr Arg Pro Lys His Phe Leu Gln Met Leu Ser Leu Glu Asn Cys Arg
    815                 820                 825 ctt aca gaa gcc agt tgc aag gac ctt gct gct gtc ttg gtt gtc agc      2605
Leu Thr Glu Ala Ser Cys Lys Asp Leu Ala Ala Val Leu Val Val Ser
830                 835                 840                 845 aag aag ctg aca cac ctg tgc ttg gcc aag aac ccc att ggg gat aca      2653
Lys Lys Leu Thr His Leu Cys Leu Ala Lys Asn Pro Ile Gly Asp Thr
            850                 855                 860 ggg gtg aag ttt ctg tgt gag ggc ttg agt tac cct gat tgt aaa ctg      2701
Gly Val Lys Phe Leu Cys Glu Gly Leu Ser Tyr Pro Asp Cys Lys Leu
        865                 870                 875 cag acc ttg gtg tta cag caa tgc agc ata acc aag ctt ggc tgt aga      2749
Gln Thr Leu Val Leu Gln Gln Cys Ser Ile Thr Lys Leu Gly Cys Arg
    880                 885                 890 tat ctc tca gag gcg ctc caa gaa gcc tgc agc ctc aca aac ctg gac      2797
Tyr Leu Ser Glu Ala Leu Gln Glu Ala Cys Ser Leu Thr Asn Leu Asp
895                 900                 905 ttg agt atc aac cag ata gct cgt gga ttg tgg att ctc tgt cag gca      2845
Leu Ser Ile Asn Gln Ile Ala Arg Gly Leu Trp Ile Leu Cys Gln Ala
910                 915                 920                 925 tta gag aat cca aac tgt aac cta aaa cac cta cgg ttg aag acc tat      2893
Leu Glu Asn Pro Asn Cys Asn Leu Lys His Leu Arg Leu Lys Thr Tyr
            930                 935                 940 gaa act aat ttg gaa atc aag aag ctg ttg gag gaa gtg aaa gaa aag      2941
Glu Thr Asn Leu Glu Ile Lys Lys Leu Leu Glu Glu Val Lys Glu Lys
        945                 950                 955 aat ccc aag ctg act att gat tgc aat gct tcc ggg gca acg gca cct      2989
Asn Pro Lys Leu Thr Ile Asp Cys Asn Ala Ser Gly Ala Thr Ala Pro
    960                 965                 970 ccg tgc tgt gac ttt ttt tgc tga gcagcctggg atcgctctac gaattacaca    3043
Pro Cys Cys Asp Phe Phe Cys
    975                 980 ggaagcggga ttcgggtctc taagatgtct tatgaatgca ggtcagaggg tcacatgtta    3103
acactagagt ctgtcgagag gtaggatttg acactggttt tctcactatt tttgggagat    3163
tctgcacgag tcacgcaccc ccttcacatg acgctatgta ctttctcaca gggataataa    3223
agttagagca ctctcgttgc aa                                             3245

<210> SEQ ID NO 3
<211> LENGTH: 980
<212> TYPE: PRT
<213> ORGANISM: Homo sapiens

<400> SEQUENCE: 3

Met Thr Ser Pro Gln Leu Glu Trp Thr Leu Gln Thr Leu Leu Glu Gln
1               5                   10                  15

Leu Asn Glu Asp Glu Leu Lys Ser Phe Lys Ser Leu Leu Trp Ala Phe
            20                  25                  30

Pro Leu Glu Asp Val Leu Gln Lys Thr Pro Trp Ser Glu Val Glu Glu
        35                  40                  45

Ala Asp Gly Lys Lys Leu Ala Glu Ile Leu Val Asn Thr Ser Ser Glu
    50                  55                  60

Asn Trp Ile Arg Asn Ala Thr Val Asn Ile Leu Glu Glu Met Asn Leu
65                  70                  75                  80

Thr Glu Leu Cys Lys Met Ala Lys Ala Glu Met Met Glu Asp Gly Gln
                85                  90                  95

Val Gln Glu Ile Asp Asn Pro Glu Leu Gly Asp Ala Glu Glu Asp Ser
```

-continued

```
                100                 105                 110
Glu Leu Ala Lys Pro Gly Glu Lys Gly Trp Arg Asn Ser Met Glu
            115                 120                 125
Lys Gln Ser Leu Val Trp Lys Asn Thr Phe Trp Gln Gly Asp Ile Asp
            130                 135                 140
Asn Phe His Asp Asp Val Thr Leu Arg Asn Gln Arg Phe Ile Pro Phe
145                 150                 155                 160
Leu Asn Pro Arg Thr Pro Arg Lys Leu Thr Pro Tyr Thr Val Val Leu
                165                 170                 175
His Gly Pro Ala Gly Val Gly Lys Thr Thr Leu Ala Lys Lys Cys Met
                180                 185                 190
Leu Asp Trp Thr Asp Cys Asn Leu Ser Pro Thr Leu Arg Tyr Ala Phe
                195                 200                 205
Tyr Leu Ser Cys Lys Glu Leu Ser Arg Met Gly Pro Cys Ser Phe Ala
                210                 215                 220
Glu Leu Ile Ser Lys Asp Trp Pro Glu Leu Gln Asp Asp Ile Pro Ser
225                 230                 235                 240
Ile Leu Ala Gln Ala Gln Arg Ile Leu Phe Val Val Asp Gly Leu Asp
                245                 250                 255
Glu Leu Lys Val Pro Pro Gly Ala Leu Ile Gln Asp Ile Cys Gly Asp
                260                 265                 270
Trp Glu Lys Lys Lys Pro Val Pro Val Leu Leu Gly Ser Leu Leu Lys
                275                 280                 285
Arg Lys Met Leu Pro Arg Ala Ala Leu Leu Val Thr Thr Arg Pro Arg
                290                 295                 300
Ala Leu Arg Asp Leu Gln Leu Leu Ala Gln Gln Pro Ile Tyr Val Arg
305                 310                 315                 320
Val Glu Gly Phe Leu Glu Glu Asp Arg Arg Ala Tyr Phe Leu Arg His
                325                 330                 335
Phe Gly Asp Glu Asp Gln Ala Met Arg Ala Phe Glu Leu Met Arg Ser
                340                 345                 350
Asn Ala Ala Leu Phe Gln Leu Gly Ser Ala Pro Ala Val Cys Trp Ile
                355                 360                 365
Val Cys Thr Thr Leu Lys Leu Gln Met Glu Lys Gly Glu Asp Pro Val
                370                 375                 380
Pro Thr Cys Leu Thr Arg Thr Gly Leu Phe Leu Arg Phe Leu Cys Ser
385                 390                 395                 400
Arg Phe Pro Gln Gly Ala Gln Leu Arg Gly Ala Leu Arg Thr Leu Ser
                405                 410                 415
Leu Leu Ala Ala Gln Gly Leu Trp Ala Gln Met Ser Val Phe His Arg
                420                 425                 430
Glu Asp Leu Glu Arg Leu Gly Val Gln Glu Ser Asp Leu Arg Leu Phe
                435                 440                 445
Leu Asp Gly Asp Ile Leu Arg Gln Asp Arg Val Ser Lys Gly Cys Tyr
                450                 455                 460
Ser Phe Ile His Leu Ser Phe Gln Gln Phe Leu Thr Ala Leu Phe Tyr
465                 470                 475                 480
Ala Leu Glu Lys Glu Glu Gly Glu Asp Arg Asp Gly His Ala Trp Asp
                485                 490                 495
Ile Gly Asp Val Gln Lys Leu Leu Ser Gly Glu Arg Leu Lys Asn
                500                 505                 510
Pro Asp Leu Ile Gln Val Gly His Phe Leu Phe Gly Leu Ala Asn Glu
                515                 520                 525
```

-continued

Lys Arg Ala Lys Glu Leu Glu Ala Thr Phe Gly Cys Arg Met Ser Pro
530                 535                 540

Asp Ile Lys Gln Glu Leu Leu Gln Cys Lys Ala His Leu His Ala Asn
545                 550                 555                 560

Lys Pro Leu Ser Val Thr Asp Leu Lys Glu Val Leu Gly Cys Leu Tyr
                565                 570                 575

Glu Ser Gln Glu Glu Leu Ala Lys Val Val Ala Pro Phe Lys
            580                 585                 590

Glu Ile Ser Ile His Leu Thr Asn Thr Ser Glu Val Met His Cys Ser
        595                 600                 605

Phe Ser Leu Lys His Cys Gln Asp Leu Gln Lys Leu Ser Leu Gln Val
610                 615                 620

Ala Lys Gly Val Phe Leu Glu Asn Tyr Met Asp Phe Glu Leu Asp Ile
625                 630                 635                 640

Glu Phe Glu Arg Cys Thr Tyr Leu Thr Ile Pro Asn Trp Ala Arg Gln
                645                 650                 655

Asp Leu Arg Ser Leu Arg Leu Trp Thr Asp Phe Cys Ser Leu Phe Ser
            660                 665                 670

Ser Asn Ser Asn Leu Lys Phe Leu Glu Val Lys Gln Ser Phe Leu Ser
        675                 680                 685

Asp Ser Ser Val Arg Ile Leu Cys Asp His Val Thr Arg Ser Thr Cys
690                 695                 700

His Leu Gln Lys Val Glu Ile Lys Asn Val Thr Pro Asp Thr Ala Tyr
705                 710                 715                 720

Arg Asp Phe Cys Leu Ala Phe Ile Gly Lys Lys Thr Leu Thr His Leu
                725                 730                 735

Thr Leu Ala Gly His Ile Glu Trp Glu Arg Thr Met Met Leu Met Leu
            740                 745                 750

Cys Asp Leu Leu Arg Asn His Lys Cys Asn Leu Gln Tyr Leu Arg Leu
        755                 760                 765

Gly Gly His Cys Ala Thr Pro Glu Gln Trp Ala Glu Phe Phe Tyr Val
770                 775                 780

Leu Lys Ala Asn Gln Ser Leu Lys His Leu Arg Leu Ser Ala Asn Val
785                 790                 795                 800

Leu Leu Asp Glu Gly Ala Met Leu Leu Tyr Lys Thr Met Thr Arg Pro
                805                 810                 815

Lys His Phe Leu Gln Met Leu Ser Leu Glu Asn Cys Arg Leu Thr Glu
            820                 825                 830

Ala Ser Cys Lys Asp Leu Ala Ala Val Leu Val Val Ser Lys Lys Leu
        835                 840                 845

Thr His Leu Cys Leu Ala Lys Asn Pro Ile Gly Asp Thr Gly Val Lys
850                 855                 860

Phe Leu Cys Glu Gly Leu Ser Tyr Pro Asp Cys Lys Leu Gln Thr Leu
865                 870                 875                 880

Val Leu Gln Gln Cys Ser Ile Thr Lys Leu Gly Cys Arg Tyr Leu Ser
                885                 890                 895

Glu Ala Leu Gln Glu Ala Cys Ser Leu Thr Asn Leu Asp Leu Ser Ile
            900                 905                 910

Asn Gln Ile Ala Arg Gly Leu Trp Ile Leu Cys Gln Ala Leu Glu Asn
        915                 920                 925

Pro Asn Cys Asn Leu Lys His Leu Arg Leu Lys Thr Tyr Glu Thr Asn
930                 935                 940

Leu Glu Ile Lys Lys Leu Leu Glu Glu Val Lys Glu Lys Asn Pro Lys
945                 950                 955                 960

```
Leu Thr Ile Asp Cys Asn Ala Ser Gly Ala Thr Ala Pro Pro Cys Cys
            965                 970                 975

Asp Phe Phe Cys
            980

<210> SEQ ID NO 4
<211> LENGTH: 3331
<212> TYPE: DNA
<213> ORGANISM: Homo sapiens
<220> FEATURE:
<221> NAME/KEY: CDS
<222> LOCATION: (71)..(3100)

<400> SEQUENCE: 4
caggctggaa gcaagacctg acctgaggga gttcttcagc cttaacctaa ggtctcatac      60
tcggagcact atg aca tcg ccc cag cta gag tgg act ctg cag acc ctt       109
            Met Thr Ser Pro Gln Leu Glu Trp Thr Leu Gln Thr Leu
              1               5                  10 ctg gag cag ctg aac gag gat gaa tta aag agt ttc aaa tcc ctt tta       157
Leu Glu Gln Leu Asn Glu Asp Glu Leu Lys Ser Phe Lys Ser Leu Leu
 15              20                  25 tgg gct ttt ccc ctc gaa gac gtg cta cag aag acc cca tgg tct gag       205
Trp Ala Phe Pro Leu Glu Asp Val Leu Gln Lys Thr Pro Trp Ser Glu
30              35                  40                  45 gtg gaa gag gct gat ggc aag aaa ctg gca gaa att ctg gtc aac acc       253
Val Glu Glu Ala Asp Gly Lys Lys Leu Ala Glu Ile Leu Val Asn Thr
             50                  55                  60 tcc tca gaa aat tgg ata agg aat gcg act gtg aac atc ttg gaa gag       301
Ser Ser Glu Asn Trp Ile Arg Asn Ala Thr Val Asn Ile Leu Glu Glu
         65                  70                  75 atg aat ctc acg gaa ttg tgt aag atg gca aag gct gag atg atg gag       349
Met Asn Leu Thr Glu Leu Cys Lys Met Ala Lys Ala Glu Met Met Glu
     80                  85                  90 gac gga cag gtg caa gaa ata gat aat cct gag ctg gga gat gca gaa       397
Asp Gly Gln Val Gln Glu Ile Asp Asn Pro Glu Leu Gly Asp Ala Glu
 95                 100                 105 gaa gac tcg gag tta gca aag cca ggt gaa aag gaa gga tgg aga aat       445
Glu Asp Ser Glu Leu Ala Lys Pro Gly Glu Lys Glu Gly Trp Arg Asn
110                 115                 120                 125 tca atg gag aaa cag tct ttg gtc tgg aag aac acc ttt tgg caa gga       493
Ser Met Glu Lys Gln Ser Leu Val Trp Lys Asn Thr Phe Trp Gln Gly
                130                 135                 140 gac att gac aat ttc cat gac gac gtc act ctg aga aac caa cgg ttc       541
Asp Ile Asp Asn Phe His Asp Asp Val Thr Leu Arg Asn Gln Arg Phe
            145                 150                 155 att cca ttc ttg aat ccc aga aca ccc agg aag cta aca cct tac acg       589
Ile Pro Phe Leu Asn Pro Arg Thr Pro Arg Lys Leu Thr Pro Tyr Thr
        160                 165                 170 gtg gtg ctg cac ggc ccc gca ggc gtg ggg aaa acc acg ctg gcc aaa       637
Val Val Leu His Gly Pro Ala Gly Val Gly Lys Thr Thr Leu Ala Lys
    175                 180                 185 aag tgt atg ctg gac tgg aca gac tgc aac ctc agc ccg acg ctc aga       685
Lys Cys Met Leu Asp Trp Thr Asp Cys Asn Leu Ser Pro Thr Leu Arg
190                 195                 200                 205 tac gcg ttc tac ctc agc tgc aag gag ctc agc cgc atg ggc ccc tgc       733
Tyr Ala Phe Tyr Leu Ser Cys Lys Glu Leu Ser Arg Met Gly Pro Cys
                210                 215                 220 agt ttt gca gag ctg atc tcc aaa gac tgg cct gaa ttg cag gat gac       781
Ser Phe Ala Glu Leu Ile Ser Lys Asp Trp Pro Glu Leu Gln Asp Asp
            225                 230                 235
```

```
att cca agc atc cta gcc caa gca cag aga atc ctg ttc gtg gtc gat    829
Ile Pro Ser Ile Leu Ala Gln Ala Gln Arg Ile Leu Phe Val Val Asp
    240             245             250 ggc ctt gat gag ctg aaa gtc cca cct ggg gcg ctg atc cag gac atc    877
Gly Leu Asp Glu Leu Lys Val Pro Pro Gly Ala Leu Ile Gln Asp Ile
255             260             265 tgc ggg gac tgg gag aag aag aag ccg gtc ccc gtc ctc ctg ggg agt    925
Cys Gly Asp Trp Glu Lys Lys Lys Pro Val Pro Val Leu Leu Gly Ser
270             275             280             285 ttg ctg aag agg aag atg tta ccc agg gca gcc ttg ctg gtc acc acg    973
Leu Leu Lys Arg Lys Met Leu Pro Arg Ala Ala Leu Leu Val Thr Thr
            290             295             300 cgg ccc agg gca ctg agg gac ctc cag ctc ctg gcg cag cag ccg atc   1021
Arg Pro Arg Ala Leu Arg Asp Leu Gln Leu Leu Ala Gln Gln Pro Ile
305             310             315 tac gta agg gtg gag ggc ttc ctg gag gag gac agg agg gcc tat ttc   1069
Tyr Val Arg Val Glu Gly Phe Leu Glu Glu Asp Arg Arg Ala Tyr Phe
    320             325             330 ctg aga cac ttt gga gac gag gac caa gcc atg cgt gcc ttt gag cta   1117
Leu Arg His Phe Gly Asp Glu Asp Gln Ala Met Arg Ala Phe Glu Leu
335             340             345 atg agg agc aac gcg gcc ctg ttc cag ctg ggc tcg gcc ccc gcg gtg   1165
Met Arg Ser Asn Ala Ala Leu Phe Gln Leu Gly Ser Ala Pro Ala Val
350             355             360             365 tgc tgg att gtg tgc acg act ctg aag ctg cag atg gag aag ggg gag   1213
Cys Trp Ile Val Cys Thr Thr Leu Lys Leu Gln Met Glu Lys Gly Glu
            370             375             380 gac ccg gtc ccc acc tgc ctc acc cgc acg ggg ctg ttc ctg cgt ttc   1261
Asp Pro Val Pro Thr Cys Leu Thr Arg Thr Gly Leu Phe Leu Arg Phe
                385             390             395 ctc tgc agc cgg ttc ccg cag ggc gca cag ctg cgg ggc gcg ctg cgg   1309
Leu Cys Ser Arg Phe Pro Gln Gly Ala Gln Leu Arg Gly Ala Leu Arg
        400             405             410 acg ctg agc ctc ctg gcc gcg cag ggc ctg tgg gcg cag atg tcc gtg   1357
Thr Leu Ser Leu Leu Ala Ala Gln Gly Leu Trp Ala Gln Met Ser Val
    415             420             425 ttc cac cga gag gac ctg gaa agg ctc ggg gtg cag gag tcc gac ctc   1405
Phe His Arg Glu Asp Leu Glu Arg Leu Gly Val Gln Glu Ser Asp Leu
430             435             440             445 cgt ctg ttc ctg gac gga gac atc ctc cgc cag gac aga gtc tcc aaa   1453
Arg Leu Phe Leu Asp Gly Asp Ile Leu Arg Gln Asp Arg Val Ser Lys
            450             455             460 ggc tgc tac tcc ttc atc cac ctc agc ttc cag cag ttt ctc act gcc   1501
Gly Cys Tyr Ser Phe Ile His Leu Ser Phe Gln Gln Phe Leu Thr Ala
                465             470             475 ctg ttc tac gcc ctg gag aag gag gag ggg gag gac agg gac ggc cac   1549
Leu Phe Tyr Ala Leu Glu Lys Glu Glu Gly Glu Asp Arg Asp Gly His
        480             485             490 gcc tgg gac atc ggg gac gta cag aag ctg ctt tcc gga gaa gaa aga   1597
Ala Trp Asp Ile Gly Asp Val Gln Lys Leu Leu Ser Gly Glu Glu Arg
    495             500             505 ctc aag aac ccc gac ctg att caa gta gga cac ttc tta ttc ggc ctc   1645
Leu Lys Asn Pro Asp Leu Ile Gln Val Gly His Phe Leu Phe Gly Leu
510             515             520             525 gct aac gag aag aga gcc aag gag ttg gag gcc act ttt ggc tgc cgg   1693
Ala Asn Glu Lys Arg Ala Lys Glu Leu Glu Ala Thr Phe Gly Cys Arg
            530             535             540 atg tca ccg gac atc aaa cag gaa ttg ctg caa tgc aaa gca cat ctt   1741
Met Ser Pro Asp Ile Lys Gln Glu Leu Leu Gln Cys Lys Ala His Leu
                545             550             555
```

```
cat gca aat aag ccc tta tcc gtg acc gac ctg aag gag gtc ttg ggc         1789
His Ala Asn Lys Pro Leu Ser Val Thr Asp Leu Lys Glu Val Leu Gly
        560             565             570 tgc ctg tat gag tct cag gag gag gag ctg gcg aag gtg gtg gtg gcc         1837
Cys Leu Tyr Glu Ser Gln Glu Glu Glu Leu Ala Lys Val Val Val Ala
575             580             585 ccg ttc aag gaa att tct att cac ctg aca aat act tct gaa gtg atg         1885
Pro Phe Lys Glu Ile Ser Ile His Leu Thr Asn Thr Ser Glu Val Met
590             595             600             605 cat tgt tcc ttc agc ctg aag cat tgt caa gac ttg cag aaa ctc tca         1933
His Cys Ser Phe Ser Leu Lys His Cys Gln Asp Leu Gln Lys Leu Ser
        610             615             620 ctg cag gta gca aag ggg gtg ttc ctg gag aat tac atg gat ttt gaa         1981
Leu Gln Val Ala Lys Gly Val Phe Leu Glu Asn Tyr Met Asp Phe Glu
        625             630             635 ctg gac att gaa ttt gaa agc tca aac agc aac ctc aag ttt ctg gaa         2029
Leu Asp Ile Glu Phe Glu Ser Ser Asn Ser Asn Leu Lys Phe Leu Glu
        640             645             650 gtg aaa caa agc ttc ctg agt gac tct tct gtg cgg att ctt tgt gac         2077
Val Lys Gln Ser Phe Leu Ser Asp Ser Ser Val Arg Ile Leu Cys Asp
655             660             665 cac gta acc cgt agc acc tgt cat ctg cag aaa gtg gag att aaa aac         2125
His Val Thr Arg Ser Thr Cys His Leu Gln Lys Val Glu Ile Lys Asn
670             675             680             685 gtc acc cct gac acc gcg tac cgg gac ttc tgt ctt gct ttc att ggg         2173
Val Thr Pro Asp Thr Ala Tyr Arg Asp Phe Cys Leu Ala Phe Ile Gly
        690             695             700 aag aag acc ctc acg cac ctg acc ctg gca ggg cac atc gag tgg gaa         2221
Lys Lys Thr Leu Thr His Leu Thr Leu Ala Gly His Ile Glu Trp Glu
        705             710             715 cgc acg atg atg ctg atg ctg tgt gac ctg ctc aga aat cat aaa tgc         2269
Arg Thr Met Met Leu Met Leu Cys Asp Leu Leu Arg Asn His Lys Cys
        720             725             730 aac ctg cag tac ctg agg ttg gga ggt cac tgt gcc acc ccg gag cag         2317
Asn Leu Gln Tyr Leu Arg Leu Gly Gly His Cys Ala Thr Pro Glu Gln
735             740             745 tgg gct gaa ttc ttc tat gtc ctc aaa gcc aac cag tcc ctg aag cac         2365
Trp Ala Glu Phe Phe Tyr Val Leu Lys Ala Asn Gln Ser Leu Lys His
750             755             760             765 ctg cgt ctc tca gcc aat gtg ctc ctg gat gag ggt gcc atg ttg ctg         2413
Leu Arg Leu Ser Ala Asn Val Leu Leu Asp Glu Gly Ala Met Leu Leu
        770             775             780 tac aag acc atg aca cgc cca aaa cac ttc ctg cag atg ttg tcg ttg         2461
Tyr Lys Thr Met Thr Arg Pro Lys His Phe Leu Gln Met Leu Ser Leu
        785             790             795 gaa aac tgt cgt ctt aca gaa gcc agt tgc aag gac ctt gct gct gtc         2509
Glu Asn Cys Arg Leu Thr Glu Ala Ser Cys Lys Asp Leu Ala Ala Val
        800             805             810 ttg gtt gtc agc aag aag ctg aca cac ctg tgc ttg gcc aag aac ccc         2557
Leu Val Val Ser Lys Lys Leu Thr His Leu Cys Leu Ala Lys Asn Pro
815             820             825 att ggg gat aca ggg gtg aag ttt ctg tgt gag ggc ttg agt tac cct         2605
Ile Gly Asp Thr Gly Val Lys Phe Leu Cys Glu Gly Leu Ser Tyr Pro
830             835             840             845 gat tgt aaa ctg cag acc ttg gtg tta cag caa tgc agc ata acc aag         2653
Asp Cys Lys Leu Gln Thr Leu Val Leu Gln Gln Cys Ser Ile Thr Lys
        850             855             860 ctt ggc tgt aga tat ctc tca gag gcg ctc caa gaa gcc tgc agc ctc         2701
Leu Gly Cys Arg Tyr Leu Ser Glu Ala Leu Gln Glu Ala Cys Ser Leu
        865             870             875
```

-continued

| | | |
|---|---|---|
| aca aac ctg gac ttg agt atc aac cag ata gct cgt gga ttg tgg att<br>Thr Asn Leu Asp Leu Ser Ile Asn Gln Ile Ala Arg Gly Leu Trp Ile<br>880 885 890 | 2749 |
| ctc tgt cag gca tta gag aat cca aac tgt aac cta aaa cac cta cgc<br>Leu Cys Gln Ala Leu Glu Asn Pro Asn Cys Asn Leu Lys His Leu Arg<br>895 900 905 | 2797 |
| ctc tgg agc tgc tcc ctc atg cct ttc tat tgt cag cat ctt gga tct<br>Leu Trp Ser Cys Ser Leu Met Pro Phe Tyr Cys Gln His Leu Gly Ser<br>910 915 920 925 | 2845 |
| gct ctc ctc agc aat cag aag ctt gaa act ctg gac ctg ggc cag aat<br>Ala Leu Leu Ser Asn Gln Lys Leu Glu Thr Leu Asp Leu Gly Gln Asn<br>930 935 940 | 2893 |
| cat ttg tgg aag agt ggc ata att aag ctc ttt ggg gtt cta aga caa<br>His Leu Trp Lys Ser Gly Ile Ile Lys Leu Phe Gly Val Leu Arg Gln<br>945 950 955 | 2941 |
| aga act gga tcc ttg aag ata ctc agg ttg aag acc tat gaa act aat<br>Arg Thr Gly Ser Leu Lys Ile Leu Arg Leu Lys Thr Tyr Glu Thr Asn<br>960 965 970 | 2989 |
| ttg gaa atc aag aag ctg ttg gag gaa gtg aaa gaa aag aat ccc aag<br>Leu Glu Ile Lys Lys Leu Leu Glu Glu Val Lys Glu Lys Asn Pro Lys<br>975 980 985 | 3037 |
| ctg act att gat tgc aat gct tcc ggg gca acg gca cct ccg tgc tgt<br>Leu Thr Ile Asp Cys Asn Ala Ser Gly Ala Thr Ala Pro Pro Cys Cys<br>990 995 1000 1005 | 3085 |
| gac ttt ttt tgc tga gcagcctggg atcgctctac gaattacaca ggaagcggga<br>Asp Phe Phe Cys | 3140 |
| ttcgggtctc taagatgtct tatgaatgca ggtcagaggg tcacatgtta acactagagt | 3200 |
| ctgtcgagag gtaggatttg acactggttt tctcactatt tttgggagat tctgcacgag | 3260 |
| tcacgcaccc ccttcacatg acgctatgta ctttctcaca gggataataa agttagagca | 3320 |
| ctctcgttgc a | 3331 |

<210> SEQ ID NO 5
<211> LENGTH: 1009
<212> TYPE: PRT
<213> ORGANISM: Homo sapiens

<400> SEQUENCE: 5

Met Thr Ser Pro Gln Leu Glu Trp Thr Leu Gln Thr Leu Leu Glu Gln
1               5                   10                  15

Leu Asn Glu Asp Glu Leu Lys Ser Phe Lys Ser Leu Leu Trp Ala Phe
            20                  25                  30

Pro Leu Glu Asp Val Leu Gln Lys Thr Pro Trp Ser Glu Val Glu Glu
        35                  40                  45

Ala Asp Gly Lys Lys Leu Ala Glu Ile Leu Val Asn Thr Ser Ser Glu
    50                  55                  60

Asn Trp Ile Arg Asn Ala Thr Val Asn Ile Leu Glu Glu Met Asn Leu
65                  70                  75                  80

Thr Glu Leu Cys Lys Met Ala Lys Ala Glu Met Met Glu Asp Gly Gln
                85                  90                  95

Val Gln Glu Ile Asp Asn Pro Glu Leu Gly Asp Ala Glu Glu Asp Ser
            100                 105                 110

Glu Leu Ala Lys Pro Gly Glu Lys Glu Gly Trp Arg Asn Ser Met Glu
        115                 120                 125

Lys Gln Ser Leu Val Trp Lys Asn Thr Phe Trp Gln Gly Asp Ile Asp
    130                 135                 140

Asn Phe His Asp Asp Val Thr Leu Arg Asn Gln Arg Phe Ile Pro Phe
145                 150                 155                 160

```
Leu Asn Pro Arg Thr Pro Arg Lys Leu Thr Pro Tyr Thr Val Val Leu
                165                 170                 175
His Gly Pro Ala Gly Val Gly Lys Thr Thr Leu Ala Lys Lys Cys Met
            180                 185                 190
Leu Asp Trp Thr Asp Cys Asn Leu Ser Pro Thr Leu Arg Tyr Ala Phe
        195                 200                 205
Tyr Leu Ser Cys Lys Glu Leu Ser Arg Met Gly Pro Cys Ser Phe Ala
    210                 215                 220
Glu Leu Ile Ser Lys Asp Trp Pro Glu Leu Gln Asp Ile Pro Ser
225                 230                 235                 240
Ile Leu Ala Gln Ala Gln Arg Ile Leu Phe Val Val Asp Gly Leu Asp
                245                 250                 255
Glu Leu Lys Val Pro Pro Gly Ala Leu Ile Gln Asp Ile Cys Gly Asp
            260                 265                 270
Trp Glu Lys Lys Lys Pro Val Pro Val Leu Leu Gly Ser Leu Leu Lys
        275                 280                 285
Arg Lys Met Leu Pro Arg Ala Ala Leu Leu Val Thr Thr Arg Pro Arg
    290                 295                 300
Ala Leu Arg Asp Leu Gln Leu Leu Ala Gln Gln Pro Ile Tyr Val Arg
305                 310                 315                 320
Val Glu Gly Phe Leu Glu Glu Asp Arg Arg Ala Tyr Phe Leu Arg His
                325                 330                 335
Phe Gly Asp Glu Asp Gln Ala Met Arg Ala Phe Glu Leu Met Arg Ser
            340                 345                 350
Asn Ala Ala Leu Phe Gln Leu Gly Ser Ala Pro Ala Val Cys Trp Ile
        355                 360                 365
Val Cys Thr Thr Leu Lys Leu Gln Met Glu Lys Gly Glu Asp Pro Val
    370                 375                 380
Pro Thr Cys Leu Thr Arg Thr Gly Leu Phe Leu Arg Phe Leu Cys Ser
385                 390                 395                 400
Arg Phe Pro Gln Gly Ala Gln Leu Arg Gly Ala Leu Arg Thr Leu Ser
                405                 410                 415
Leu Leu Ala Ala Gln Gly Leu Trp Ala Gln Met Ser Val Phe His Arg
            420                 425                 430
Glu Asp Leu Glu Arg Leu Gly Val Gln Glu Ser Asp Leu Arg Leu Phe
        435                 440                 445
Leu Asp Gly Asp Ile Leu Arg Gln Asp Arg Val Ser Lys Gly Cys Tyr
    450                 455                 460
Ser Phe Ile His Leu Ser Phe Gln Gln Phe Leu Thr Ala Leu Phe Tyr
465                 470                 475                 480
Ala Leu Glu Lys Glu Glu Gly Glu Asp Arg Asp Gly His Ala Trp Asp
                485                 490                 495
Ile Gly Asp Val Gln Lys Leu Leu Ser Gly Glu Glu Arg Leu Lys Asn
            500                 505                 510
Pro Asp Leu Ile Gln Val Gly His Phe Leu Phe Gly Leu Ala Asn Glu
        515                 520                 525
Lys Arg Ala Lys Glu Leu Glu Ala Thr Phe Gly Cys Arg Met Ser Pro
    530                 535                 540
Asp Ile Lys Gln Glu Leu Leu Gln Cys Lys Ala His Leu His Ala Asn
545                 550                 555                 560
Lys Pro Leu Ser Val Thr Asp Leu Lys Glu Val Leu Gly Cys Leu Tyr
                565                 570                 575
Glu Ser Gln Glu Glu Glu Leu Ala Lys Val Val Val Ala Pro Phe Lys
```

```
                580             585             590
Glu Ile Ser Ile His Leu Thr Asn Thr Ser Glu Val Met His Cys Ser
        595                 600                 605

Phe Ser Leu Lys His Cys Gln Asp Leu Gln Lys Leu Ser Leu Gln Val
        610                 615                 620

Ala Lys Gly Val Phe Leu Glu Asn Tyr Met Asp Phe Glu Leu Asp Ile
625                 630                 635                 640

Glu Phe Glu Ser Ser Asn Ser Asn Leu Lys Phe Leu Glu Val Lys Gln
                645                 650                 655

Ser Phe Leu Ser Asp Ser Ser Val Arg Ile Leu Cys Asp His Val Thr
            660                 665                 670

Arg Ser Thr Cys His Leu Gln Lys Val Glu Ile Lys Asn Val Thr Pro
        675                 680                 685

Asp Thr Ala Tyr Arg Asp Phe Cys Leu Ala Phe Ile Gly Lys Lys Thr
        690                 695                 700

Leu Thr His Leu Thr Leu Ala Gly His Ile Glu Trp Glu Arg Thr Met
705                 710                 715                 720

Met Leu Met Leu Cys Asp Leu Leu Arg Asn His Lys Cys Asn Leu Gln
                725                 730                 735

Tyr Leu Arg Leu Gly Gly His Cys Ala Thr Pro Glu Gln Trp Ala Glu
            740                 745                 750

Phe Phe Tyr Val Leu Lys Ala Asn Gln Ser Leu Lys His Leu Arg Leu
        755                 760                 765

Ser Ala Asn Val Leu Leu Asp Glu Gly Ala Met Leu Leu Tyr Lys Thr
        770                 775                 780

Met Thr Arg Pro Lys His Phe Leu Gln Met Leu Ser Leu Glu Asn Cys
785                 790                 795                 800

Arg Leu Thr Glu Ala Ser Cys Lys Asp Leu Ala Ala Val Leu Val Val
                805                 810                 815

Ser Lys Lys Leu Thr His Leu Cys Leu Ala Lys Asn Pro Ile Gly Asp
            820                 825                 830

Thr Gly Val Lys Phe Leu Cys Glu Gly Leu Ser Tyr Pro Asp Cys Lys
        835                 840                 845

Leu Gln Thr Leu Val Leu Gln Gln Cys Ser Ile Thr Lys Leu Gly Cys
        850                 855                 860

Arg Tyr Leu Ser Glu Ala Leu Gln Glu Ala Cys Ser Leu Thr Asn Leu
865                 870                 875                 880

Asp Leu Ser Ile Asn Gln Ile Ala Arg Gly Leu Trp Ile Leu Cys Gln
                885                 890                 895

Ala Leu Glu Asn Pro Asn Cys Asn Leu Lys His Leu Arg Leu Trp Ser
            900                 905                 910

Cys Ser Leu Met Pro Phe Tyr Cys Gln His Leu Gly Ser Ala Leu Leu
        915                 920                 925

Ser Asn Gln Lys Leu Glu Thr Leu Asp Leu Gly Gln Asn His Leu Trp
        930                 935                 940

Lys Ser Gly Ile Ile Lys Leu Phe Gly Val Leu Arg Gln Arg Thr Gly
945                 950                 955                 960

Ser Leu Lys Ile Leu Arg Leu Lys Thr Tyr Glu Thr Asn Leu Glu Ile
                965                 970                 975

Lys Lys Leu Leu Glu Glu Val Lys Glu Lys Asn Pro Lys Leu Thr Ile
            980                 985                 990

Asp Cys Asn Ala Ser Gly Ala Thr  Ala Pro Pro Cys Cys  Asp Phe Phe
        995                 1000                1005
```

Cys

<210> SEQ ID NO 6
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 6
gcccaattac agccaaatcc ctgag                                   25

<210> SEQ ID NO 7
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 7
ggccgaggca gacagattac ctaaa                                   25

<210> SEQ ID NO 8
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 8
accgtgctgg gccagatttt cagt                                    24

<210> SEQ ID NO 9
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 9
gcagaggttg caatgagcag agacg                                   25

<210> SEQ ID NO 10
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 10
ccaccatgcc tggctgacac tttat                                   25

<210> SEQ ID NO 11
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 11
gcagaggttg caatgagcag agacg                                   25

<210> SEQ ID NO 12
<211> LENGTH: 25
<212> TYPE: DNA
<213> ORGANISM: Artificial sequence
<220> FEATURE:

<223> OTHER INFORMATION: synthetic oligonucleotide

<400> SEQUENCE: 12
gtagtggctc cgtctctgct cattg                                  25

<210> SEQ ID NO 13
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 13
aggccatcga ccacgaacag gattc                                  25

<210> SEQ ID NO 14
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 14
gacgacgtca ctctgagaaa ccaac                                  25

<210> SEQ ID NO 15
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 15
tgcagaggaa acgcaggaac agc                                    23

<210> SEQ ID NO 16
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 16
tttgctgaag aggaagatgt taccc                                  25

<210> SEQ ID NO 17
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 17
cgaggccgaa taagaagtgt cctac                                  25

<210> SEQ ID NO 18
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 18
gtgggcgcag atgtccgtgt tc                                     22

<210> SEQ ID NO 19

```
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 19
cctaattgcc aagtcgtgtc tcc                                              23

<210> SEQ ID NO 20
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 20
ggtctcagtt tctagcccaa gtt                                              23

<210> SEQ ID NO 21
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 21
acacggtgaa aacctgtctg tgc                                              23

<210> SEQ ID NO 22
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 22
ccactgcacc cggccaagaa ctt                                              23

<210> SEQ ID NO 23
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 23
gctgggggcc actgctctca atc                                              23

<210> SEQ ID NO 24
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 24
gatcacgcct ttgcattcca gactg                                            25

<210> SEQ ID NO 25
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 25
```

-continued

```
aactcagatg atccgcccac ctctc                                           25

<210> SEQ ID NO 26
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 26
aaaacaacac ctgtgtcctg tgatg                                           25

<210> SEQ ID NO 27
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 27
ttaacatgtt tctacctgta tctgc                                           25

<210> SEQ ID NO 28
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 28
cttcacaggg cgttagccag agg                                             23

<210> SEQ ID NO 29
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 29
ccagcccggg aaagatgaca aga                                             23

<210> SEQ ID NO 30
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 30
aaggtgctgg ggctacaggt gtct                                            24

<210> SEQ ID NO 31
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 31
gccaacatgg tgaaacccct ctc                                             23

<210> SEQ ID NO 32
<211> LENGTH: 25
<212> TYPE: DNA
<213> ORGANISM: Artificial sequence
<220> FEATURE:
```

<223> OTHER INFORMATION: synthetic oligonucleotide

<400> SEQUENCE: 32
ctgtccccca gaaatccca aaaac                25

<210> SEQ ID NO 33
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 33
caaccgaatc atccctgaac ttc                23

<210> SEQ ID NO 34
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 34
caaacaccaa actcatgacc ata                23

<210> SEQ ID NO 35
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 35
tccttccagc atcctcgcac                20

<210> SEQ ID NO 36
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 36
atgaccagga caccccaggt tcta                24

<210> SEQ ID NO 37
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 37
caccttgcat gctctcaaac acca                24

<210> SEQ ID NO 38
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 38
caagaagctt agtcatcgtt                20

<210> SEQ ID NO 39

```
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 39
agctgatagg gtatactctg                                            20

<210> SEQ ID NO 40
<211> LENGTH: 18
<212> TYPE: DNA
<213> ORGANISM: Artificial sequence
<220> FEATURE:
<223> OTHER INFORMATION: synthetic oligonucleotide

<400> SEQUENCE: 40
aaacccatac ctgagtat                                              18

<210> SEQ ID NO 41
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 41
tggccatgat gactcccaca gg                                         22

<210> SEQ ID NO 42
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 42
ccaggttttt aaaagttaca tttg                                       24

<210> SEQ ID NO 43
<211> LENGTH: 13
<212> TYPE: DNA
<213> ORGANISM: Homo sapiens

<400> SEQUENCE: 43
agccaggtgg gta                                                   13

<210> SEQ ID NO 44
<211> LENGTH: 13
<212> TYPE: DNA
<213> ORGANISM: Homo sapiens

<400> SEQUENCE: 44
agccagatgg gta                                                   13
```

NALP7-BASED DIAGNOSIS OF FEMALE REPRODUCTIVE CONDITIONS

CROSS REFERENCE TO RELATED APPLICATIONS

This application is a National Phase Application of PCT International Application No. PCT/CA2006/001256, filed Aug. 3, 2006, which was published in English under PCT Article 21(2) as International Publication No. WO 2007/014463. This application further claims the benefit of U.S. Provisional Patent Application No. 60/704,896 filed Aug. 3, 2005. All of these applications are incorporated herein by reference in their entirety.

REFERENCE TO SEQUENCE LISTING

Pursuant to 37 C.F.R. 1.821(c), a sequence listing is submitted herewith as an ASCII compliant text file named "Sequence Listing.txt" which was created on Feb. 22, 2011 and has a size of 77,390 bytes. The content of the aforementioned file named "Sequence listing.txt" is hereby incorporated by reference in its entirety.

FIELD OF THE INVENTION

The present invention relates to methods and reagents for the diagnosis of conditions of the female reproductive system.

BACKGROUND OF THE INVENTION

A number of female reproductive conditions exist which not only have adverse effects on fertility, but may pose serious health concerns to female sufferers, such as cancer. Such conditions include gestational trophoblastic diseases, such as the phenomenon of recurrent hydatidiform moles (HM), an abnormal human pregnancy with no embryo and cystic degeneration of placental villi. Recurrent HM is a rare clinical entity in which molar tissues are diploids and have a biparental contribution to their genome. In a number of cases this condition has been observed to have a familial basis. Recurrent hydatidiform molar tissues are undistinguishable at both gross morphology and histopathology levels from the common non-recurrent moles, which are androgenetic in most of the cases (80% of the cases), but may also be biparental (in 20% of the cases). The common form of hydatidiform moles occur in 1 in every 1500 pregnancies in western countries, but at a higher incidence in the Far East, Africa and Central America where the incidence of this condition may reach 1 in 100 pregnancies. Epidemiological studies performed to correlate this higher incidence with various environmental factors failed to reach significant conclusions, but shows a higher risk of hydatidiform moles at the beginning and end of a woman's reproductive cycle. In addition, the relative risk of developing a second HM after a previous molar pregnancy is 20 to 40 times the incidence of moles in the general population indicating genetic susceptibility to moles.

In mammals, maternal effect genes, in addition to those coding for oocyte mRNAs and proteins that accumulate in the egg during oogenesis, extend to genes required in the maternal reproductive tract for normal preimplantation and implantation development. Applicant has previously mapped a genetic region responsible for recurrent HMs to a 15-cM interval on 19q13.4 in two unrelated families, MoLb1 and MoGe2 (Moglabey et al., 1999). Additional families from various ethnic groups were reported and most of them were found linked to 19q13.4, indicating a major locus in this region leading to recurrent HMs. The analysis of these families narrowed down the HM candidate region to a 1.1-Mb interval (Sensi et al. 2000; Hodges et al. 2003).

Therefore, there is a continued need to identify the gene associated with such disorders.

The present description refers to a number of documents, the content of which is herein incorporated by reference in their entirety.

SUMMARY OF THE INVENTION

The invention relates to NALP7 and conditions of the female reproductive system, including diagnosis of such conditions based on NALP7.

Accordingly, In a first aspect, the invention provides a method for diagnosing a reproductive condition or a predisposition for a reproductive condition in a female (e.g., human) subject, the method comprising detecting an alteration in the sequence of the NALP7 gene or the sequence of its mRNA or encoded polypeptide in a tissue sample from said subject relative to the sequence of the wild-type NALP7 gene or the sequence of its mRNA or encoded polypeptide, wherein said alteration indicates that the subject suffers from or has a predisposition for the reproductive condition. In embodiments, the reproductive condition is selected from gestational trophoplastic disease, gestational trophoblastic tumor, hydatidiform mole, molar pregnancy, biparental molar pregnancy, androgenetic molar pregnancy, invasive mole, choriocarcinoma, premature ovarian failure, infertility, endometriosis, implantation failure, blighted ovum, recurrent spontaneous abortions, and preeclampsia.

In embodiments, the alteration is associated with altered splicing of a NALP7 transcript, such as altered splicing of exon 3, exon 7, or both, of said NALP7 gene.

In an embodiment, the method further comprises amplification of a nucleic acid sequence suspected of comprising the alteration in the sample prior to the detection of the alteration.

In embodiments, detection of the alteration is performed using a method selected from: (a) sequencing of the NALP7 nucleic acid sequence; (b) hybridization of a nucleic acid probe capable of specifically hybridizing to a NALP7 nucleic acid sequence comprising the alteration and not to a corresponding wild-type NALP7 nucleic acid sequence; (c) restriction fragment length polymorphism analysis (RFLP); (d) amplified fragment length polymorphism PCR (AFLP-PCR); (e) amplification of a nucleic acid fragment comprising a NALP7 nucleic acid sequence using a primer specific for the alteration, wherein the primer produces an amplified product if the alteration is present and does not produce the same amplified product when a corresponding wild-type NALP7 nucleic acid sequence is used as a template for amplification; (f) sequencing of the NALP7 polypeptide; (g) digestion of the NALP7 polypeptide followed by mass spectrometry or HPLC analysis of the peptide fragments, wherein the alteration of the NALP7 polypeptide results in an altered mass spectrometry or HPLC spectrum as compared to wild-type NALP7 polypeptide; and (h) immunodetection using an immunological reagent which exhibits altered immunoreactivity with a NALP7 polypeptide comprising the alteration relative to a corresponding wild-type NALP7 polypeptide.

In an embodiment, the method further comprises determining cytokine release of an immune cell of said subject, wherein a decrease in cytokine release relative to a control level of cytokine release is further indicative that the subject suffers from or has a predisposition for the reproductive condition.

In embodiments, the control level of cytokine release is selected from an established standard and a level of cytokine release of an immune cell comprising a wild-type NALP7 nucleic acid.

In an embodiment, the method further comprises selecting a prophylactic or therapeutic course of action in accordance with the detected alteration.

In a further aspect, the invention provides a nucleic acid probe capable of specifically hybridizing to an altered NALP7 nucleotide sequence and not to a corresponding wild-type NALP7 nucleotide sequence.

The invention further provides a primer or an amplification pair capable of specifically producing an amplified product from a template comprising an altered NALP7 nucleotide sequence and which does not produce the same amplified product from a template comprising a corresponding wild-type NALP7 nucleotide sequence. In embodiments, the primer or amplification pair are selected from SEQ ID NOs: 6-42.

The invention further provides an isolated altered NALP7 nucleic acid or fragment thereof, wherein said altered NALP7 nucleic acid or fragment thereof comprises a nucleotide sequence comprising an alteration relative to the nucleotide sequence of a wild-type NALP7 nucleic acid or fragment thereof.

The invention further provides an isolated nucleic acid comprising a sequence that encodes an altered NALP7 polypeptide or fragment thereof.

The invention further provides an isolated nucleic acid comprising an alteration described herein and which is substantially identical to or substantially complementary to the above-mentioned isolated nucleic acid.

In an embodiment, the nucleic acid comprises an altered NALP7 nucleotide sequence comprising an alteration associated with altered splicing of a NALP7 transcript, such as altered splicing of exon 3, exon 7, or both, of said NALP7 gene.

In an embodiment, the alteration occurs at a splice donor site, such as at the splice donor site at the boundary of exon 3 and intron 3, the splice donor site at the boundary of exon 7 and intron 7, or both, of the NALP7 gene.

In an embodiment, the alteration results in a loss of a cleavage site for a restriction endonuclease (e.g., BstN1) in the NALP7 gene.

In an embodiment, the alteration is at an amino acid position within the NALP7 polypeptide selected from position 693, 399, 379, 99 and 657 of the NALP7 polypeptide.

In embodiments, the alteration is selected from a substitution of the C corresponding to the first position of the codon for Arg 693 of the NALP7 polypeptide and a substitution of the G corresponding to the second position of the codon for Arg 693 of the NALP7 polypeptide. In further embodiments, the alteration is selected from a substitution of Arg 693 with Trp (R693W).

In further embodiments, the alteration is selected from (a) a substitution of Cys 399 with Tyr (C399Y); (b) a substitution of Lys 379 with Asn (K379N); (c) a substitution of the codon for Glu 99 with a stop codon (E99X); and (d) a substitution of Asp 657 with Val (D657V).

In embodiments, the alteration is selected from: (a) a substitution of G with A at the splice donor site at the boundary of exon 3 and intron 3 (IVS3+1G>A); (b) a substitution of G with A at the splice donor site at the boundary of exon 7 and intron 7 (IVS7+1G>A); (c) a substitution of C with T corresponding to the first position of the codon for Arg 693 of the NALP7 polypeptide; (d) a substitution of G with A corresponding to the second position of the codon for Cys 84 of the NALP7 polypeptide; (e) a substitution of G with A corresponding to the second position of the codon for Cys 399 of the NALP7 polypeptide; (f) a substitution of G with C corresponding to the third position of the codon for Lys 379 of the NALP7 polypeptide; (g) a substitution of G with T corresponding to the first position of the codon for Glu 99 of the NALP7 polypeptide; and (h) a substitution of A with T corresponding to the second position of Asp 657 of the NALP7 polypeptide The invention further provides a replicative cloning vector comprising the above-mentioned nucleic acid and a replicon operative in a host cell.

The invention further provides a vector (e.g., an expression vector) comprising the above-mentioned nucleic acid operably linked to a transcriptionally regulatory element.

The invention further provides a host cell transformed with the above-mentioned vector, replicative cloning vector or expression vector.

The invention further provides an isolated, recombinant or substantially pure altered NALP7 polypeptide encoded by the above-mentioned nucleic acid.

The invention further provides a polypeptide comprising an alteration described herein and which is substantially identical to the above-mentioned isolated, recombinant or substantially pure altered NALP7 polypeptide.

The invention further provides an antibody that binds specifically binds the above-mentioned altered NALP7 polypeptide.

The invention further provides an antibody capable of altered immunoreactivity with a NALP7 polypeptide comprising the alteration relative to a corresponding wild-type NALP7 polypeptide, such as an antibody that selectively binds to the altered NALP7 polypeptide but does not bind to or binds to a lesser extent to a corresponding wild-type NALP7 polypeptide under the same conditions.

The invention further provides a kit for diagnosing a reproductive condition or a predisposition for a reproductive condition in a female subject, said kit comprising means for detection of an alteration in the sequence of a NALP7 gene or the sequence of its mRNA or encoded polypeptide in a tissue sample from said subject relative to the sequence of a corresponding wild-type NALP7 gene or the sequence of its mRNA or encoded polypeptide. In embodiments, such means are chosen from reagents for: (a) sequencing of the NALP7 nucleic acid sequence; (b) hybridization of a nucleic acid probe capable of specifically hybridizing to a NALP7 nucleic acid sequence comprising the alteration and not to a corresponding wild-type NALP7 nucleic acid sequence; (c) restriction fragment length polymorphism analysis (RFLP); (d) amplified fragment length polymorphism PCR (AFLP-PCR); (e) amplification of a nucleic acid fragment comprising a NALP7 nucleic acid sequence using a primer specific for the alteration, wherein the primer produces an amplified product if the alteration is present and does not produce the same amplified product when a corresponding wild-type NALP7 nucleic acid sequence is used as a template for amplification; (f) sequencing of the NALP7 polypeptide; (g) digestion of the NALP7 polypeptide followed by mass spectrometry or HPLC analysis of the peptide fragments, wherein the alteration of the NALP7 polypeptide results in an altered mass spectrometry or HPLC spectrum as compared to wild-type NALP7 polypeptide; and (h) immunodetection using an immunological reagent which exhibits altered immunoreactivity with a NALP7 polypeptide comprising the alteration relative to a corresponding wild-type NALP7 polypeptide. In embodiments, the reagents are chosen from the above-mentioned antibody, primer (or pair), and probe.

In an embodiment, the kit further comprises means to determine cytokine release of an immune cell of said subject.

In an embodiment, the kit further comprises instructions for diagnosing a reproductive condition or a predisposition for a reproductive condition in a female subject.

The Invention further provides a method of identifying a compound for restoring defective immune function associated with a reproductive condition, said method comprising determining whether cytokine release of an immune cell comprising an altered NALP7 nucleic acid or polypeptide is increased in the presence of a test compound relative to in the absence of said test compound; wherein said increase is indicative that said test compound may be used for restoring defective immune function associated with a reproductive condition.

In an embodiment, the immune cell is a a peripheral blood mononuclear cell (PBMC). Iin a further embodiment, the immune cell is a lymphocyte or monocyte.

In embodiments, the cytokine is selected from interleukin-1β (IL-1β) and TNF alpha (TNFα).

Other advantages and features of the present invention will become more apparent upon reading of the following non-restrictive description of specific embodiments thereof, given by way of example only with reference to the accompanying drawings.

BRIEF DESCRIPTION OF THE DRAWINGS

FIG. 6: Genomic DNA sequence of human NALP7 (SEQ ID NO: 1; derived from GenBank accession No. NT_011109.15)

FIG. 7: DNA (SEQ ID NO: 2) and polypeptide (SEQ ID NO: 3) sequence of human NALP7, 980 amino acid isoform (GenBank accession No. AY154462 or NM_206828). Coding sequence is defined by position 71-3013 of DNA sequence.

FIG. 8: DNA (SEQ ID NO: 4) and polypeptide (SEQ ID NO: 5) sequence of human NALP7, 1009 amino acid isoform (GenBank accession No. NM_139176). Coding sequence is defined by position 71-3100 of DNA sequence.

DESCRIPTION OF ILLUSTRATIVE EMBODIMENTS

Figure 1:
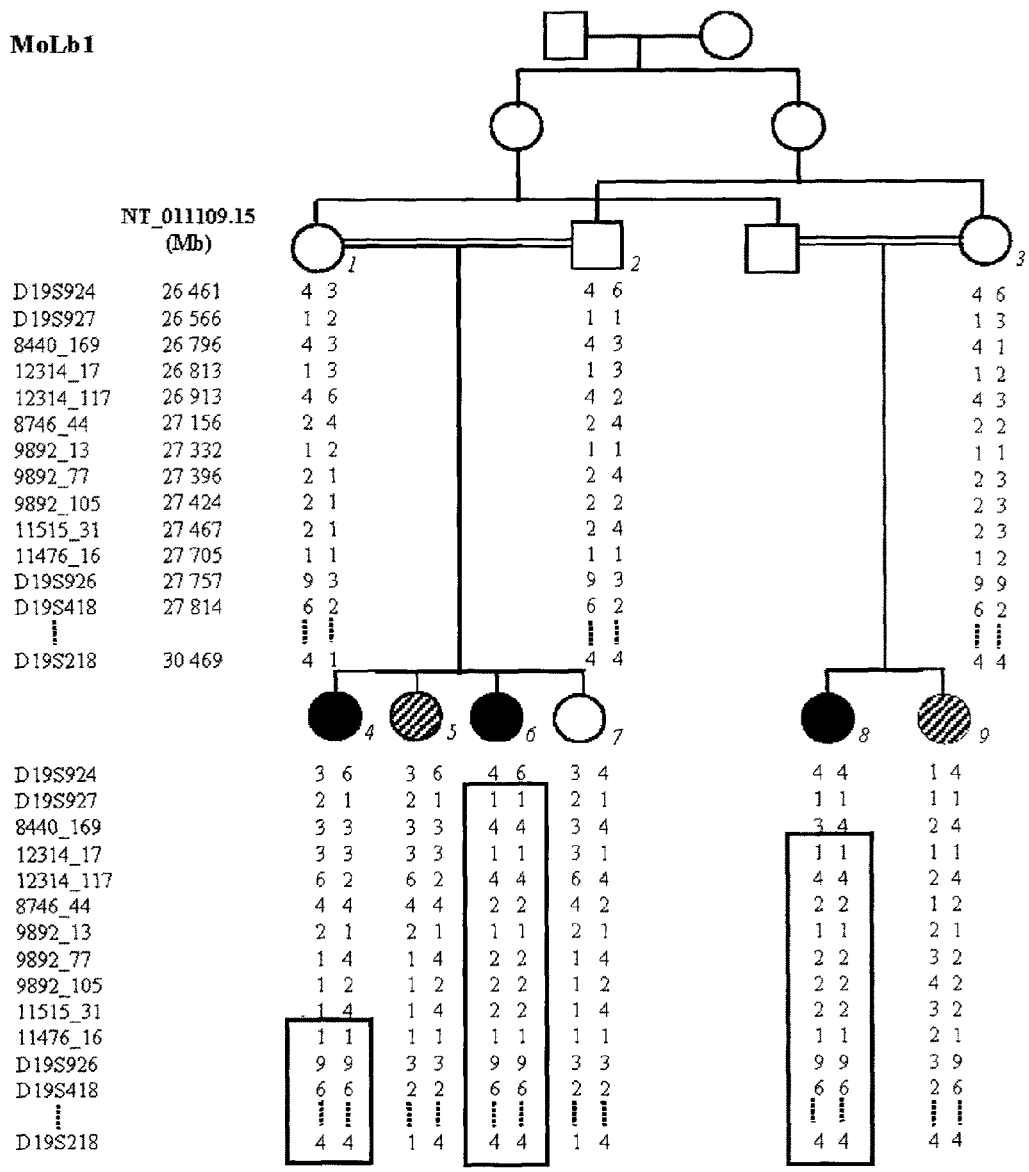
FIG. 1: Partial pedigree of family MoLb1 showing the limit of the proximal boundary of the hydatidiform mole candidate locus on 19q13.4. Markers are ordered (top to bottom) from centromere to telomere and their positions are given in contig NT_011109.15. Genotyping was performed using publicly available and newly generated microsatellite markers by incorporation of radiolabelled nucleotides in the PCR amplification and separation of the products on 5% denaturing polyacrylamide gels. Black symbols indicate affected women, white symbols unaffected, and shaded symbol indicates a woman with unknown disease status. The homozygous region in the three affected sisters is indicated. The black box shows the region that is homozygous in each patient. The proximal border of the candidate region is defined by marker 11515_31 due to its heterozygosity in patient 4.

In the studies described herein, applicant has identified a defective maternal gene, NALP7, and its causative role in different conditions affecting the female reproductive system, such as recurrent molar pregnancies.

NALP7 is one of 14 members of the NALP proteins, a large subfamily of the CATERPILLER protein family involved in inflammation and apoptosis. NALP7 is related to the mouse MATER, (also a member of the CATERPILLER protein family). The NALP7 gene consists of 11 exons encoding for 1009 amino acid protein (the longest isoform). Three transcriptional isoforms NALP7V1-V3 involving the alternative splicing of exons 5, 9, and 10 have been described (Okada et al., 2004). NALP7 contains an amino-terminal PYRIN domain (PYD) (also called DAPIN), a putative protein-protein interaction domain found in all the CATERPILLER protein family and thought to function in apoptotic and inflammatory signaling pathways; a NACHT domain found in neuronal apoptosis inhibitor proteins as well as in those involved in the major histocompatibility complex (MHC) class II transactivation and caspase-recruitment proteins; a nuclear localization signal (NLS) present within the NACHT domain; and 9 to 10 leucine-rich repeats (LRRs) (depending on the splicing isoforms) found in the Ran GTPase activating proteins (Ran-GAP1), highly conserved proteins essential for nuclear transport, cell cycle regulation, mitotic spindle formation, and post mitotic nuclear envelope assembly. NALP7 has been shown to inhibit caspase-1 dependent IL-1β secretion, which in turn induces NALP7 expression. NALP7 (also referred to as PYPAF3) was recently shown to be upregulated in testicular seminoma tumors where its down regulation by transfection with small interfering RNA results in growth suppression (Okada et al., 2004; International patent application publication no. WO2004/031410 [Nakamura et al., Apr. 15, 2004]).

As described herein, applicants have identified a number of mutations in the NALP7 gene in families having female members suffering from reproductive conditions, such as recurrent hydatidiform moles. Such identified mutations include:
a) a substitution of G with A in the GT sequence of the splice donor site at the boundary of exon 3 and intron 3 (IVS3+1G>A) of the NALP7 gene;
b) a substitution of G with A in the GT sequence of the splice donor site at the boundary of exon 7 and intron 7 (IVS7+1G>A) of the NALP7 gene;
c) a substitution of C with T corresponding to the first position of the codon for Arg 693 of the NALP7 polypeptide;
d) a substitution of G with A corresponding to the second position of the codon for Cys 84 of the NALP7 polypeptide,
e) a substitution of G with A corresponding to the second position of the codon for Cys 399 of the NALP7 polypeptide,
f) a substitution of G with C corresponding to the third position of the codon for Lys 379 of the NALP7 polypeptide,
g) a substitution of G with T corresponding to the first position of the codon for Glu 99 of the NALP7 polypeptide; and
h) a substitution of A with T corresponding to the second position of Asp 657 of the NALP7 polypeptide.

The above mutations (a) and (b) have resulted in incorrect splicing of the NALP7 transcript, notably in respect of the exon 3/intron 3 boundary and the exon 7/intron 7 boundary, respectively. For example of incorrect splicing in case of (b), the mutation was shown to result in the inclusion of the entire intron 7 resulting in the addition of one amino acid (a serine) to exon 7, followed by a stop codon, resulting therefore in a shortened protein of 824 amino acids.

The above mutation (a) has also resulted in a loss of a cleavage site of the restriction endonuclease BstN1.

The above mutation (c) has resulted in an alteration at Arg 693 of the NALP7 polypeptide sequence, notably its substitution with Trp. The above mutation (d) has resulted in an alteration at Cys 84 of the NALP7 polypeptide sequence, notably its substitution with Tyr. The above mutation (e) has resulted in an alteration at Cys 399 of the NALP7 polypeptide sequence, notably its substitution with Tyr. The above mutation (f) has resulted in an alteration at Lys 379 of the NALP7 polypeptide sequence, notably its substitution with Asn. The above mutation (g) has resulted in an alteration at Glu 99 of the NALP7 polypeptide sequence, notably its substitution with a stop codon. The above mutation (h) has resulted in an alteration at Asp 657 of the NALP7 polypeptide, notably its substitution with a Val.

Applicant has further shown herein NALP7 transcription in EBV lymphoblastoid cell lines, normal human uterus, ovaries, unfertilized oocytes at the germinal vesicle and metaphase I stages, early embryo cleavage (1 to 6 cells) and first trimester chorionic villi at 6 and 12 weeks of gestation.

Accordingly, in an aspect, the invention relates to NALP7-based diagnosis of conditions of the female reproductive system. The invention thus provides methods and reagents to detect an alteration in NALP7 or its encoded polypeptide, including an alteration in its nucleic acid sequence (including its DNA, mRNA (or cDNA)) or polypeptide sequence, in a sample from a female subject. The presence of an alteration relative to the corresponding wild-type nucleic acid sequence or polypeptide sequence is indicative that the female subject suffers from or has a predisposition for the reproductive condition. The invention further relates to screening to identify compounds capable of restoring defective immune function associated with a female reproductive condition, e.g., that associated with mutant NALP7.

The invention thus provides a method for diagnosing a reproductive condition or a predisposition for a reproductive condition in a female subject, the method comprising detecting an alteration in the sequence of the NALP7 gene or the sequence of its mRNA or encoded polypeptide in a tissue sample from said subject relative to the sequence of the wild-type NALP7 gene or the sequence of its mRNA or encoded polypeptide. The presence of the alteration indicates that the subject suffers from or has a predisposition for the reproductive condition.

The invention further provides an in vitro method for diagnosing a reproductive condition or a predisposition for a reproductive condition in a female subject, the method comprising detecting an alteration in the sequence of the NALP7 gene or the sequence of its mRNA or encoded polypeptide in a tissue sample from said subject relative to the sequence of the wild-type NALP7 gene or the sequence of its mRNA or encoded polypeptide. The presence of the alteration indicates that the subject suffers from or has a predisposition for the reproductive condition.

Examples of wild-type NALP7 DNA and polypeptide sequences are provided in FIGS. 6-8 and SEQ ID NOs 1, 2 and 4 (DNA) and SEQ ID NOs 3 and 5 (polypeptide).

Applicant has further described herein a decrease in cytokine release in immune cells obtained from a patient harboring a NALP7 mutation. Accordingly, in an embodiment, the above-mentioned method further comprises determining cytokine release of an immune cell of said subject, wherein a decrease in cytokine release relative to a control level of cytokine release is further indicative that the subject suffers from or has a predisposition for the reproductive condition.

The above-mentioned control level of cytokine release may be for example an established standard (e.g., a level established in the art for an immune cell capable of wild-type, normal or healthy immune function) or a level of cytokine release of an immune cell comprising a wild-type NALP7 nucleic acid or polypeptide.

The above-mentioned immune cell may be for example a peripheral blood mononuclear cell (PBMC), lymphocyte, or monocyte.

In embodiments, the above-mentioned cytokine is selected from interleukin-1β (IL-1β) and TNF alpha (TNFα).

In an embodiment, the subject is a female mammal, e.g., a human female subject.

In embodiments, the reproductive condition is selected gestational trophoplastic disease, gestational trophoblastic tumor, hydatidiform mole, molar pregnancy, biparental molar pregnancy, androgenetic molar pregnancy, invasive mole, choriocarcinoma, premature ovarian failure, infertility, endometriosis, implantation failure, blighted ovum, recurrent spontaneous abortions, preeclampsia, and stillbirth.

In various embodiments, the above noted tissue sample comprises a tissue or body fluid from the subject, such as blood, serum, lymphocytes, epithelia, endometrial and uterine biopsies, and oocytes.

"Alteration" as used herein in respect of a nucleotide or polypeptide sequence refers to any type of mutation or change relative to the corresponding wild-type nucleotide or polypeptide sequence, including deletions, insertions, substitutions and point mutations. In the case of a nucleotide sequence, such an alteration may occur in coding and/or non-coding regions. Mutations of a nucleotide sequence may for example result in the creation of a stop codon, frameshift mutation, altered splicing or an amino acid substitution. In the case of mutations in a regulatory region (e.g., a promoter), a decrease or loss of mRNA expression may result. Accordingly, in various embodiments, the alteration is selected from a deletion from, substitution of and/or insertion into a NALP7 nucleic acid and/or polypeptide sequence.

In an embodiment, the alteration results in altered splicing relative to wild-type NALP7. Such altered splicing may occur in respect of exon 3 and/or exon 7. In embodiments, the alteration may occur in the splice donor site, such as in the GT splice donor sequence.

In an embodiment the alteration results in altered sensitivity to a restriction endonuclease, such as a loss of a cleavage site for a restriction endonuclease. In an embodiment, the restriction endonuclease is BstN1.

In an embodiment, the alteration occurs at position 693 of the NALP7 polypeptide, in further embodiments, the alteration is a substitution of Arg 693 with a different amino acid, such as Trp.

In an embodiment, the alteration occurs at position Cys 84 of the NALP7 polypeptide, in further embodiments, the alteration is a substitution of Cys 84 with a different amino acid, such as Tyr.

In an embodiment, the alteration occurs at position 399 of the NALP7 polypeptide, in further embodiments, the alteration is a substitution of Cys 399 with a different amino acid, such as Tyr.

In an embodiment, the alteration occurs at position 379 of the NALP7 polypeptide, in further embodiments, the alteration is a substitution of Lys 379 with a different amino acid, such as Asn.

In an embodiment, the alteration occurs at position 99 of the NALP7 polypeptide, in further embodiments, the alteration is a substitution of Glu 99, such as with a stop codon In an embodiment, the alteration occurs at position 657 of the NALP7 polypeptide, in further embodiments, the alteration is a substitution of Asp 657 with a different amino acid, such as Val.

In an embodiment, the alteration occurs at a splice donor and/or splice acceptor site. In an embodiment, the alteration occurs at a splice donor site at the boundary of exon 3 and intron 3, in a further embodiment, at a splice donor site at the boundary of exon 7 and intron 7.

In further embodiments, the alteration is selected from (a) a substitution of G with A in the GT sequence of the splice donor site at the boundary of exon 3 and intron 3 (IVS3+1G>A) of the NALP7 gene; (b) a substitution of G with A in the GT sequence of the splice donor site at the boundary of exon 7 and intron 7 (IVS7+1G>A) of the NALP7 gene; (c) a substitution of C with T corresponding to the first position of the codon for Arg 693 of the NALP7 polypeptide; (d) a substitution of G with A corresponding to the second position of the codon for Cys 84 of the NALP7 polypeptide; (f) a substitution of G with C corresponding to the third position of the codon for Lys 379 of the NALP7 polypeptide; (g) a substitution of G with T corresponding to the first position of the codon for Glu 99 of the NALP7 polypeptide; and (h) a substitution of A with T corresponding to the second position of Asp 657 of the NALP7 polypeptide.

The above-noted alteration is relative to a wild-type NALP7 sequence, examples of which are provided in FIGS. 6-8 and SEQ ID NOs 1, 2 and 4 (DNA) and SEQ ID NOs 3 and 5 (polypeptide). The invention further provides an isolated nucleic acid or polypeptide comprising an nucleotide or amino acid sequence selected from SEQ ID NOs 1, 2 and 4 (DNA) and SEQ ID NOs 3 and 5 (polypeptide) further comprising an alteration noted herein or any combination of the alterations noted herein.

The detection of any combination of the above-noted alterations may also be used in the methods of the invention.

Further, the above-mentioned method may further comprise selection of a prophylactic or therapeutic course of action in accordance with the detected alteration.

The above noted alteration may be detected by a number of methods which are known in the art. Examples of suitable methods include sequencing of the NALP7 nucleic acid sequence; hybridization of a nucleic acid probe capable of specifically hybridizing to a NALP7 nucleic acid sequence comprising the alteration and not to (or to a lesser extent to) a corresponding wild-type NALP7 nucleic acid sequence (under comparable hybridization conditions); restriction fragment length polymorphism analysis (RFLP); Amplified fragment length polymorphism PCR (AFLP-PCR); amplification of a nucleic acid fragment comprising a NALP7 nucleic acid sequence using a primer specific for the alteration, wherein the primer produces an amplified product if the alteration is present and does not produce the same amplified product when a corresponding wild-type NALP7 nucleic acid sequence is used as a template for amplification (e.g. allele-specific PCR); sequencing of the NALP7 polypeptide; Digestion of the NALP7 polypeptide followed by mass spectrometry or HPLC analysis of the peptide fragments, wherein the alteration of the NALP7 polypeptide results in an altered mass spectrometry or HPLC spectrum as compared to wild-type NALP7 polypeptide; and immunodetection using an immunological reagent (e.g. an antibody, a ligand) which exhibits altered immunoreactivity with a NALP7 polypeptide comprising the alteration relative to a corresponding wild-type NALP7 polypeptide; Immunodetection can measure the amount of binding between a polypeptide molecule and an anti-protein antibody by the use of enzymatic, chromodynamic, radioactive, magnetic, or luminescent labels which are attached to either the anti-protein antibody or a secondary antibody which binds the anti-protein antibody. In addition, other high affinity ligands may be used. Immunoassays which can be used include e.g. ELISAs, Western blots, and other techniques known to those of ordinary skill in the art (see Harlow and Lane, Antibodies: A Laboratory Manual, Cold Spring Harbor Laboratory Press, Cold Spring Harbor, N.Y., 1999 and Edwards R, Immunodiagnostics: A Practical Approach, Oxford University Press, Oxford; England, 1999). All these detection techniques may also be employed in the format of microarrays, protein-arrays, antibody microarrays, tissue microarrays, electronic biochip or protein-chip based technologies (see Schena M., Microarray Biochip Technology, Eaton Publishing, Natick, Mass., 2000).

Further, NALP7 nucleic acid-containing sequences may be amplified using known methods (e.g. polymerase chain reaction [PCR]) prior to or in conjunction with the detection methods noted herein. Examples of PCR primers for amplification of NALP7 sequences are provided in the Examples herein. The design of various primers for such amplification is known in the art.

The detection methods herein may also be performed in an assay utilizing a substrate having detection reagents attached thereto at discrete locations, such as a nucleic acid microarray. The invention further provides a substrate comprising an isolated altered NALP7 nucleic acid described herein attached thereto.

The invention further provides a nucleic acid, e.g., a probe, capable of specifically hybridizing to the altered NALP7 nucleotide sequence and not to (or to a lesser extent to) a corresponding wild-type NALP7 nucleic acid sequence (under comparable hybridization conditions). Such hybridization may be under moderately stringent, or preferably stringent, conditions, e.g. as noted below. Such a probe or plurality thereof may in embodiments be attached to a solid substrate, as noted above.

The invention further provides (a) nucleic acid primer(s) (e.g. an amplification pair) specific for the alteration, wherein the primer(s) produce(s) an amplified product if the alteration is present and does not produce the same amplified product when a corresponding wild-type NALP7 nucleic acid sequence is used as a template for amplification.

The invention further provides an isolated nucleic acid encoding the above-mentioned altered NALP7 polypeptide. The invention further provides an isolated altered NALP7 nucleic acid comprising the above noted alteration. The invention further provides an isolated, substantially pure, or recombinant polypeptide encoded by the above-mentioned nucleic acid, as well as fusion proteins comprising the polypeptide and an additional polypeptide sequence (e.g. a heterologous polypeptide sequence). The invention further provides an isolated, substantially pure, or recombinant polypeptide comprising the above noted alteration. The invention further provides isolated nucleic acids having a nucleotide sequence which is substantially identical to the above-noted altered NALP7 nucleic acid of the invention. The invention further provides an isolated, substantially pure, or recombinant polypeptide having an amino acid sequence which is substantially identical to the above-noted altered NALP7 polypeptide of the invention.

"Altered NALP7 nucleic acid" or "altered NALP7 gene" as used herein refer to a nucleic acid comprising a nucleotide sequence which differs from a wild-type NALP7 nucleotide sequence in that it comprises an alteration as noted herein. "NALP7 nucleic acid", "NALP7 gene", "wild-type NALP7 nucleic acid" or "wild-type NALP7 gene" as used herein refer to a nucleic acid comprising a nucleotide sequence encoding a NALP7 polypeptide or protein. "NALP7 polypeptide", "NALP7 protein", "wild-type NALP7 polypeptide" or "wild-type NALP7 protein" as used herein refer to a polypeptide comprising the amino acid sequence of a NALP7 polypeptide present in subjects not suffering from a reproductive condition, and having NALP7 activity. Examples of nucleotide sequences of human wild-type NALP7 genes or nucleic acids are set forth in FIGS. 6-8 and SEQ ID NOs: 1, 2 and 4. Examples of amino acid sequences of human wild-type NALP7 polypeptides or proteins are set forth in FIGS. 7 and 8 and SEQ ID NOs: 3 (980 amino acid isoform) and 5 (1009 amino acid isoform).

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid sequence is "homologous" to another sequence if the two sequences are "substantially identical", as used herein, and the functional activity of the sequences is conserved (as used herein, the term 'homologous' does not infer evolutionary relatedness). Two nucleic acid sequences are considered "substantially identical" if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%. As used herein, a given percentage of homology between sequences denotes the degree of sequence identity in optimally aligned sequences. The invention thus further provides a nucleic acid comprising a nucleotide sequence having at least 60%, 70%, 75%, 80%, 85%, 90% or 95% identity with any of SEQ ID Nos 6-42, or with an altered version of any of SEQ ID NOs 1, 2 and 4 (DNA) and SEQ ID NOs 3 and 5 (polypeptide) comprising an alteration noted herein or any combination of the alterations noted herein. An "unrelated" or "non-homologous" sequence shares less than 40% identity, though preferably less than about 25% identity, with any of SEQ ID NOs described herein.

Substantially complementary nucleic acids are nucleic acids in which the complement of one molecule is "substantially identical" to the other molecule. Two nucleic acid or protein sequences are considered "substantially identical" if, when optimally aligned, they share at least about 70% sequence identity. In alternative embodiments, sequence identity may for example be at least 75%, at least 80%, at least 85%, at least 90%, or at least 95%. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information (through the internet at http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Examples of nucleic acid hybridization conditions are described further below.

The invention further provides a vector comprising the above-mentioned nucleic acid and a replicon active in a host cell (e.g. replicative cloning vector). The invention further provides a vector comprising the above-mentioned nucleic acid operably-linked to a transcriptionally regulatory sequence (e.g. an expression vector).

The invention further provides a host cell transformed with the above-mentioned vector.

The invention further provides an immunological reagent, such as an antibody, which exhibits different immunoreactivity with an altered NALP7 polypeptide, i.e., comprising the above-noted alteration, relative to a wild-type NALP7 polypeptide.

As noted above, an isolated nucleic acid, for example a nucleic acid sequence encoding a polypeptide of the invention, or homolog, fragment or variant thereof, may further be incorporated into a vector, such as a recombinant expression vector. In an embodiment, the vector will comprise transcriptional regulatory sequences or a promoter operably-linked to a nucleic acid comprising a sequence capable of encoding a peptide compound, polypeptide or domain of the invention. A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences. Generally, operably-linked DNA sequences are contiguous and, where necessary to join two protein coding regions, in reading frame. However, since for example enhancers generally function when separated from the promoters by several kilobases and intronic sequences may be of variable lengths, some polynucleotide elements may be operably-linked but not contiguous. "Transcriptional regulatory sequence/element" is a generic term that refers to DNA sequences, such as initiation and termination signals, enhancers, and promoters, splicing signals, polyadenylation signals which induce or control transcription of protein coding sequences with which they are operably-linked. "Promoter" refers to a DNA regulatory region capable of binding directly or indirectly to RNA polymerase in a cell and initiating transcription of a downstream (3' direction) coding sequence. For purposes of the present invention, the promoter is bound at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain "TATA" boses and "CCAT" boxes. Prokaryotic promoters contain Shine-Dalgarno sequences in addition to the −10 and −35 consensus sequences.

As used herein, "nucleic acid molecule", refers to a polymer of nucleotides. Non-limiting examples thereof include DNA (i.e. genomic DNA, cDNA) and RNA molecules (i.e. mRNA). The nucleic acid molecule can be obtained by cloning techniques or synthesized. DNA can be double-stranded or single-stranded (coding strand or non-coding strand [antisense]).

The term "recombinant DNA" as known in the art refers to a DNA molecule resulting from the joining of DNA segments. This is often referred to as genetic engineering.

The terminology "amplification pair" refers herein to a pair of oligonucleotides (oligos) of the present invention, which are selected to be used together in amplifying a selected nucleic acid sequence by one of a number of types of amplification processes, preferably a polymerase chain reaction. Other types of amplification processes include ligase chain reaction, strand displacement amplification, or nucleic acid sequence-based amplification. As commonly known in the art, the oligos are designed to bind to a complementary sequence under selected conditions. Accordingly, the invention further provides an amplification pair capable of amplifying an altered NALP7 nucleic acid, a wild-type NALP7 nucleic acid, or a fragment of an altered NALP7 nucleic acid or a wild-type NALP7 nucleic acid. Examples of suitable amplification pairs are set forth in Example 6 below, whereby any suitable combination of forward (fwd) and reverse (rev) primers for a given region are shown (both those utilized for PCR and sequencing may be used as an amplification pair). For example: For Exon 1, representative amplification pairs include SEQ ID NOs: 6 and 7, and SEQ ID NOs: 6 and 35. For Exon 2, representative amplification pairs include SEQ ID NOs: 8 and 9, and SEQ ID NOs: 8 and 36. For Exon 3, representative amplification pairs include SEQ ID NOs: 10 and 11, and SEQ ID NOs: 10 and 37. For Exon 4, representative amplification pairs include SEQ ID NOs: 12 and 13, SEQ ID NOs: 14 and 15, SEQ ID NOs: 16 and 17, and SEQ ID NOs: 18 and 19. For Exon 5, representative amplification pairs include SEQ ID NOs: 20 and 21, and SEQ ID NOs: 20 and 38. For Exon 6, a representative amplification pair is SEQ ID NOs: 22 and 23. For Exon 7, representative amplification pairs include SEQ ID NOs: 24 and 25, and SEQ ID NOs: 39 and 25. For Exon 8, representative amplification pairs include SEQ ID NOs: 26 and 27, and SEQ ID NOs: 41 and 42. For Exon 9, a representative amplification pair is SEQ ID NOs: 28 and 29. For Exon 10, representative amplification pairs include SEQ ID NOs: 30 and 31, and SEQ ID NOs: 30 and 40. For Exon 11, a representative amplification pair is SEQ ID NOs: 32 and 33. For the region comprising the IVS3+1 G>A mutation described herein, a representative amplification pair is SEQ ID NOs: 10 and 34.

Oligonucleotide probes or primers of the present invention may be of any suitable length, depending on the particular assay format and the particular needs and targeted sequences employed. In general, the oligonucleotide probes or primers are at least 12 nucleotides in length, preferably between 15 and 24 molecules, and they may be adapted to be especially suited to a chosen nucleic acid amplification system. As commonly known in the art, the oligonucleotide probes and primers can be designed by taking into consideration the melting point of hybridization thereof with its targeted sequence (see below and in Sambrook et al., 1989, Molecular Cloning—A Laboratory Manual, 2nd Edition, CSH Laboratories; Ausubel et al., 1989, in Current Protocols in Molecular Biology, John Wiley & Sons Inc., N.Y.).

"Nucleic acid hybridization" refers generally to the hybridization of two single-stranded nucleic acid molecules having complementary base sequences, which under appropriate conditions will form a thermodynamically favored double-stranded structure. Examples of hybridization conditions can be found in the two laboratory manuals referred above (Sambrook et al., 1989, supra and Ausubel, et al. (eds), 1989, *Current Protocols in Molecular Biology*, Vol. 1, Green Publishing Associates, Inc., and John Wiley & Sons, Inc., New York) and are commonly known in the art. Hybridization to filter-bound sequences under moderately stringent conditions may, for example, be performed in 0.5 M NaHPO$_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO$_4$, 7% SDS, 1 mM EDTA at 65° C., and washing in 0.1×SSC/0.1% SDS at 68° C. (see Ausubel, et al. (eds), 1989, supra). In other examples of hybridization, a nitrocellulose filter can be incubated overnight at 65° C. with a labeled probe in a solution containing 50% formamide, high salt (5×SSC or 5×SSPE), 5×Denhardt's solution, 1% SDS, and 100 µg/ml denatured carrier DNA (i.e. salmon sperm DNA). The non-specifically binding probe can then be washed off the filter by several washes in 0.2×SSC/0.1% SDS at a temperature which is selected in view of the desired stringency: room temperature (low stringency), 42° C. (moderate stringency) or 65° C. (high stringency). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York). The selected temperature is based on the melting temperature (Tm) of the DNA hybrid (Sambrook et al. 1989, supra). Generally, stringent conditions are selected to be about 5° C. lower than the thermal melting point for the specific sequence at a defined ionic strength and pH. Of course, RNA-DNA hybrids can also be formed and detected. In such cases, the conditions of hybridization and washing can be adapted according to well-known methods by the person of ordinary skill. Stringent conditions will be preferably used (Sambrook et al., 1989, supra).

Probes or primers of the invention can be utilized with naturally occurring sugar-phosphate backbones as well as modified backbones including phosphorothioates, dithionates, alkyl phosphonates and α-nucleotides and the like. Modified sugar-phosphate backbones are generally taught by Miller, 1988, Ann. Reports Med. Chem. 23:295 and Moran et al., 1987, Nucleic acid molecule. Acids Res., 14:5019. Probes or primers of the invention can be constructed of either ribonucleic acid (RNA) or deoxyribonucleic acid (DNA), and preferably of DNA.

The types of detection methods in which probes can be used include Southern blots (DNA detection), dot or slot blots (DNA, RNA), and Northern blots (RNA detection). Although less preferred, labeled proteins could also be used to detect a particular nucleic acid sequence to which it binds.

Although the present invention is not specifically dependent on the use of a label for the detection of a particular nucleic acid sequence, such a label might be beneficial, by increasing the sensitivity of the detection. Furthermore, it enables automation (the same can also be said of detection of proteins using ligands such as antibodies). Probes can be labeled according to numerous well-known methods (Sambrook et al., 1989, supra). Non-limiting examples of detectable markers include ligands, fluorophores, chemiluminescent agents, enzymes, and antibodies. Other detectable markers for use with probes, which can enable an increase in sensitivity of the method of the invention, include biotin and radionucleotides. It will be understood by the person of ordinary skill that the choice of a particular label dictates the manner in which it is bound to the probe.

As commonly known, radioactive nucleotides can be incorporated into probes of the invention by several methods. Non-limiting examples thereof include kinasing the 5' ends of the probes using gamma $^{32}$P ATP and polynucleotide kinase, using the Klenow fragment of Pol I of *E. coli* in the presence of radioactive dNTP (e.g. uniformly labeled DNA probe using random oligonucleotide primers in low-melt gels), using the SP6/T7 system to transcribe a DNA segment in the presence of one or more radioactive NTP, and the like.

As used herein, "oligonucleotides" or "oligos" define a molecule having two or more nucleotides (ribo or deoxyribonucleotides). The size of the oligo will be dictated by the particular situation and ultimately on the particular use thereof and adapted accordingly by the person of ordinary skill. An oligonucleotide can be synthesized chemically or derived by cloning according to well-known methods.

As used herein, a "primer" defines an oligonucleotide which is capable of annealing to a target sequence, thereby creating a double stranded region which can serve as an initiation point for DNA synthesis under suitable conditions.

Amplification of a selected, or target, nucleic acid sequence may be carried out by a number of suitable methods. See generally Kwoh et al., 1990, Am. Biotechnol. Lab. 8:14-25. Numerous amplification techniques have been described and can be readily adapted to suit particular needs of a person of ordinary skill. Non-limiting examples of amplification techniques include polymerase chain reaction (PCR), ligase chain reaction (LCR), strand displacement amplification (SDA), transcription-based amplification, the Qβ replicase system and NASBA (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 1989, supra). Preferably, amplification will be carried out using PCR.

Polymerase chain reaction (PCR) is carried out in accordance with known techniques. See, e.g., U.S. Pat. Nos. 4,683,195; 4,683,202; 4,800,159; and 4,965,188 (the disclosures of all three U.S. patent are incorporated herein by reference). In general, PCR involves, a treatment of a nucleic acid sample (e.g., in the presence of a heat stable DNA polymerase) under hybridizing conditions, with one oligonucleotide primer for each strand of the specific sequence to be detected. An extension product of each primer which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analyzed to assess whether the sequence or sequences to be detected are present. Detection of the amplified sequence may be carried out by visualization following EtBr staining of the DNA following gel electrophoresis, or using a detectable label in accordance with known techniques, and the like. For a review on PCR techniques (see PCR Protocols, A Guide to Methods and Amplifications, Michael et al. Eds, Acad. Press, 1990).

Ligase chain reaction (LCR) is carried out in accordance with known techniques (Weiss, 1991, Science 254:1292). Adaptation of the protocol to meet the desired needs can be carried out by a person of ordinary skill. Strand displacement amplification (SDA) is also carried out in accordance with known techniques or adaptations thereof to meet the particular needs (Walker et al., 1992, Proc. Natl. Acad. Sci. USA 89:392-396; and ibid., 1992, Nucleic Acids Res. 20:1691-1696).

The term "vector" is commonly known in the art and defines a plasmid DNA, phage DNA, viral DNA and the like, which can serve as a DNA vehicle into which DNA of the present invention can be cloned. Numerous types of vectors exist and are well known in the art.

The term "expression" defines the process by which a gene is transcribed into mRNA (transcription), the mRNA is then being translated (translation) into one polypeptide (or protein) or more.

The recombinant expression vector of the present invention can be constructed by standard techniques known to one of ordinary skill in the art and found, for example, in Sambrook et al. (supra). A variety of strategies are available for ligating fragments of DNA, the choice of which depends on the nature of the termini of the DNA fragments and can be readily determined by persons skilled in the art. The vectors of the present invention may also contain other sequence elements to facilitate vector propagation (e.g. a replicon) and selection in bacteria and host cells. In addition, the vectors of the present invention may comprise a sequence of nucleotides for one or more restriction endonuclease sites. Coding sequences such as for selectable markers and reporter genes are well known to persons skilled in the art.

A recombinant expression vector comprising a nucleic acid sequence of the present invention may be introduced into a host cell, which may include a living cell capable of expressing the protein coding region from the defined recombinant expression vector. The living cell may include both a cultured cell and a cell within a living organism. Accordingly, the invention also provides host cells containing the recombinant expression vectors of the invention. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into cells via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (supra), and other laboratory manuals.

Recombinant production is useful for the preparation of large quantities of the protein encoded by the DNA sequence of interest. The protein can be purified according to standard protocols that take advantage of the intrinsic properties thereof, such as size and charge (i.e. SDS gel electrophoresis, gel filtration, centrifugation, ion exchange chromatography . . . ). In addition, the protein of interest can be purified via affinity chromatography using polyclonal or monoclonal antibodies or other affinity-based systems (e.g. using a suitable incorporated "tag" in the form of a fusion protein and its corresponding ligand). Suitable recombinant systems include prokaryotic and eukaryotic expression systems, which are known in the art.

The term "allele" defines an alternative form of a gene which occupies a given locus on a chromosome.

As commonly known, a "mutation" is a detectable change in the genetic material which can be transmitted to a daughter cell. As well known, a mutation can be, for example, a detectable change in one or more deoxyribonucleotide. For example, nucleotides can be added, deleted, substituted for, inverted, or transposed to a new position. Spontaneous mutations and experimentally induced mutations exist. A mutant polypeptide can be encoded from a mutant nucleic acid molecule. In addition, mutant proteins can be produced through aberrant events during replication, transcription and/or translation. Frameshifting (the switching from a particular reading frame to another) is such a mechanism that can modify the sequence of the translated protein.

A compound is "substantially pure" when it is separated from the components that naturally accompany it. Typically, a compound is substantially pure when it is at least 60%, more generally 75% or over 90%, by weight, of the total material in a sample. Thus, for example, a polypeptide that is chemically synthesized or produced by recombinant technology will generally be substantially free from its naturally associated components. A nucleic acid molecule is substantially pure when it is not immediately contiguous with (i.e., covalently linked to) the coding sequences with which it is normally contiguous in the naturally occurring genome of the organism from which the DNA of the invention is derived. A substantially pure compound can be obtained, for example, by extraction from a natural source; by expression of a recombinant nucleic acid molecule encoding a polypeptide compound; or by chemical synthesis. Purity can be measured using any appropriate method such as column chromatography, gel electrophoresis, HPLC, etc.

As used herein, the terms "molecule", "compound", "agent", or "ligand" are used interchangeably and broadly to refer to natural, synthetic or semi-synthetic molecules or compounds. The term "molecule" therefore denotes for example chemicals, macromolecules, cell or tissue extracts (from plants or animals) and the like. Non-limiting examples of molecules include nucleic acid molecules, peptides, antibodies, carbohydrates and pharmaceutical agents. The agents can be selected and screened by a variety of means including random screening, rational selection and by rational design using for example protein or ligand modelling methods such as computer modelling.

A further aspect of the invention provides an antibody that recognizes an altered NALP7 polypeptide of the invention. Antibodies may be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monoclonal antibodies may also be in the form of immunoglobulin fragments, e.g., F(ab)'$_2$ Fab or Fab' fragments. The antibodies of the invention are of any isotype, e.g., IgG or IgA, and polyclonal antibodies are of a single isotype or a mixture of isotypes. In general, techniques for preparing antibodies (including monoclonal antibodies and hybridomas) and for detecting antigens using antibodies are well known in the art.

Antibodies against the altered NALP7 polypeptide of the present invention are generated by immunization of a mammal with a partially purified fraction comprising altered NALP7 polypeptide. Such antibodies may be polyclonal or monoclonal. Methods to produce polyclonal or monoclonal antibodies are well known in the art. For a review, see Harlow and Lane (1988) and Yelton et al. (1981), both of which are herein incorporated by reference. For monoclonal antibodies, see Kohler and Milstein (1975), and Campbell, 1984, In "Monoclonal Antibody Technology: Laboratory Techniques in Biochemistry and Molecular Biology", Elsevier Science Publisher, Amsterdam, The Netherlands.

The antibodies of the invention, which are raised to a partially purified fraction comprising altered NALP7 polypeptide of the invention, are produced and identified using standard immunological assays, e.g., Western blot analysis, dot blot assay, or ELISA (see, e.g., Coligan et al. (1994), herein incorporated by reference). The antibodies are used in diagnostic methods to detect the presence of a altered NALP7 polypeptide and activity in a sample, such as a tissue or body fluid. The antibodies are also used in affinity chromatography for obtaining a purified fraction comprising the altered NALP7 polypeptide and activity of the invention.

Accordingly, a further aspect of the invention provides (i) a reagent for detecting the presence of altered NALP7 polypeptide and activity in a tissue or body fluid; and (ii) a diagnostic method for detecting the presence of altered NALP7 polypeptide and activity in a tissue or body fluid, by contacting the tissue or body fluid with an antibody of the invention, such that an immune complex is formed, and by detecting such complex to indicate the presence of altered NALP7 polypeptide and activity in the sample or the organism from which the sample is derived.

Those skilled in the art will readily understand that the immune complex is formed between a component of the sample and the antibody, and that any unbound material is removed prior to detecting the complex. It is understood that an antibody of the invention is used for screening a sample, such as, for example, blood, plasma, lymphocytes, cerebrospinal fluid, urine, saliva, epithelia and fibroblasts, for the presence of an altered NALP7 polypeptide.

For diagnostic applications, the reagent (i.e., the antibody of the invention) is either in a free state or immobilized on a solid support, such as a tube, a bead, or any other conventional support used in the field. Immobilization is achieved using direct or indirect means. Direct means include passive adsorption (non-covalent binding) or covalent binding between the support and the reagent. By "indirect means" is meant that an anti-reagent compound that interacts with a reagent is first attached to the solid support. Indirect means may also employ a ligand-receptor system, for example, where a molecule such as a vitamin is grafted onto the reagent and the corresponding receptor immobilized on the solid phase. This is illustrated by the biotin-streptavidin system. Alternatively, a peptide tail is added chemically or by genetic engineering to the reagent and the grafted or fused product immobilized by passive adsorption or covalent linkage of the peptide tail.

The present invention also relates to a kit for diagnosing a condition of the female reproductive system, or a predisposition to contracting same, comprising suitable means to detect the above-mentioned alteration, such as a probe, primer (or primer pair), or immunological reagent (e.g. antibody) in accordance with the present invention. For example, a compartmentalized kit in accordance with the present invention includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers may for example include a container which will accept the test sample (DNA, protein or cells), a container which contains the primers used in the assay, containers which contain enzymes, containers which contain wash reagents, and containers which contain the reagents used to detect the indicator products. In an embodiment the kit further comprises instructions for diagnosing a condition of the female reproductive system, or a predisposition to contracting same.

In another aspect, the invention relates to the use of a NALP7-defective immune cell (e.g., having a mutated [e.g., comprising an alteration described herein] or disrupted NALP7 gene, lacking a NALP7 gene, or having been treated or engineered for decreased NALP7 expression or function [e.g., via NALP7-targeted RNA interference or antisense oligonucleotides]) in screening assays that may be used to identify compounds that are capable of restoring defective immune function associated with a female reproductive condition noted herein. In some embodiments, such an assay may comprise the steps of (a) providing a test compound; (b) providing a a NALP7-defective immune cell; and (c) determining cytokine release in the presence versus the absence of the test compound. An increase in cytokine release in the presence versus the absence of the compound is indicative that the compound is capable of restoring defective immune function associated with a female reproductive condition.

The above-mentioned immune cell may be for example a peripheral blood mononuclear cell (PBMC), lymphocyte or monocyte. The above-mentioned cytokine may be for example interleukin-1β (IL-1β) or TNF alpha (TNFα).

Cytokine release may in embodiments be measured in response to a suitable stimulus, such as in response to bacterial lipopolysaccharide (LPS) as described in the Examples below.

The above-noted assays may be applied to a single test compound or to a plurality or "library" of such compounds (e.g. a combinatorial library). Any such compounds may be utilized as lead compounds and further modified to improve their therapeutic, prophylactic and/or pharmacological properties.

Such assay systems may comprise a variety of means to enable and optimize useful assay conditions. Such means may include but are not limited to: suitable buffer solutions, for example, for the control of pH and ionic strength and to provide any necessary components for optimal stability (e.g. protease inhibitors) of assay components, temperature control means for optimal activity and or stability of assay components, and detection means to enable the detection of the indicator product. A variety of such detection means may be used, including but not limited to one or a combination of the following: radiolabelling (e.g. $^{32}P$, $^{14}C$, $^{3}H$), antibody-based detection, fluorescence, chemiluminescence, spectroscopic methods (e.g. generation of a product with altered spectroscopic properties), various reporter enzymes or proteins (e.g. horseradish peroxidase, green fluorescent protein), specific binding reagents (e.g. biotin/(streptavidin)), and others.

The present invention is illustrated in further details by the following non-limiting examples.

EXAMPLES

Example 1

Methods

Mutation screening and analysis. Genomic structure of the screened genes were obtained from publicly available databases (http://genome.ucsc.edu/) and the primers flanking predicted exons, exon/intron boundaries and 5' and 3'UTRs were designed using Primer Select v5.05 (DNAStar). Exons were PCR amplified, visualized on 2% agarose gels stained with ethidium bromide, and sequenced directly using a 3730XL DNA Analysis System (Applied Biosystems). Sequences were aligned using SeqManII v5.05 and screened for mutations.

RT-PCR. Total RNAs was extracted from EBV transformed lymphoblast cell lines using Trizol (Invitrogen). Three micrograms of total RNA were reverse-transcribed using 200 units of M-MLV Reverse Transcriptase (Invitrogen) with RNA Guard RNase Inhibitor (Amersham) in a total volume of 50 μl. Five microliters of this preparation were then PCR amplified according to standard protocols. Sequencing of cDNA fragments were done on direct PCR products or after purification of the appropriate bands and cloning using the TOPO TA™ Cloning Kit (Invitrogen).

Example 2

Fine Mapping of the HM Candidate Region

Figure 2:
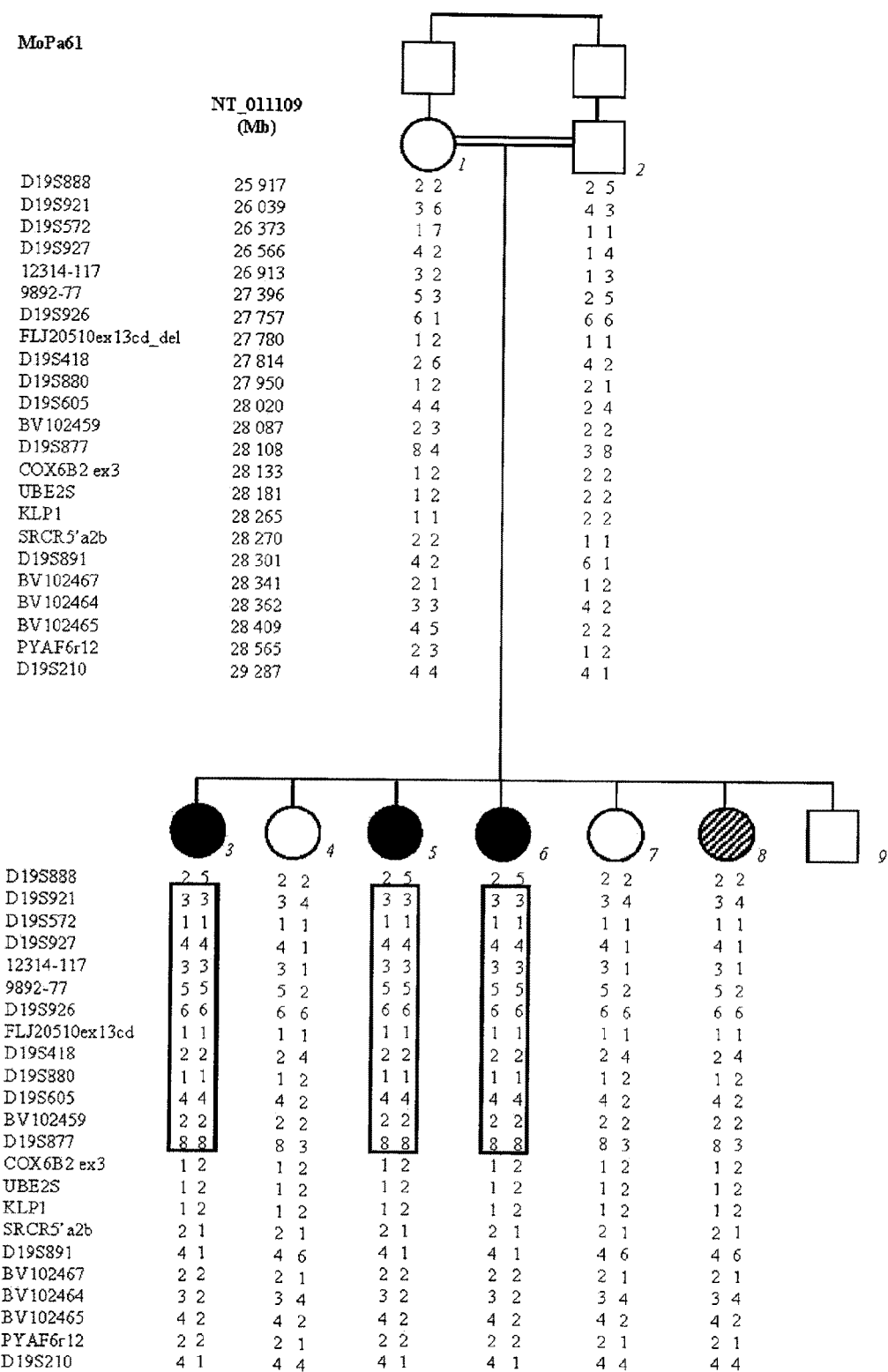
FIG. 2: Pedigree of family MoPa61 with recurrent hydatidiform moles. Twenty-three informative microsatellite markers were genotyped to determine linkage to 19q13.4. Markers are ordered (top to bottom) from centromere to telomere and are indicated on the left along with their position in contig NT_011109.15. These data define marker COX6B2 as the distal boundary of the HM candidate region due to its lack of homozygosity in all three affected sisters.

To identify the defective gene associated with recurrent HMs, applicant screened all the predicted exons of the 53 genes present in the reported hypothetical 1.1-Mb minimal interval (Sensi et al.; Hodges et al.). However, applicant did not find any mutations in this region. Applicant thus confirmed that the proximal boundary of the reported 1.1-Mb minimal interval is incorrect. Using a proximal boundary identified in family MoLb1 as a 1.29-Mb region between D19S924 and D19S926 (Moglabey et al., 1999), applicant identified herein nine new polymorphic markers from the available genomic DNA sequences and genotyped them in MoLb1. This analysis defined marker 11515-31 as the proximal boundary of the HM candidate region (FIG. 1). This new definition of the proximal boundary added a cluster of killer-cell immunoglobulin-like receptors (KIR) genes (7 to 14 genes depending on haplotypes), two KIR-related genes, NCR1, and FCAR, and NALP7. Genotyping of an additional family, MoPa61 previously reported by Mazhar and Janjua (1995) with 23 polymorphic markers from 19q13.4 demonstrated its linkage to this region and defined a single nucleotide polymorphism (SNP) located 16 bases upstream exon 3 of gene COX6B2 (NM_144613) as the distal boundary of the minimal HM candidate region (FIG. 2). Based on data from MoLb1 and MoPa61, applicant fine mapped the HM candidate region to 0.65-Mb between 11515-31 and COX6B2ex3.

Example 3

Mutation Analyses

Figure 3:
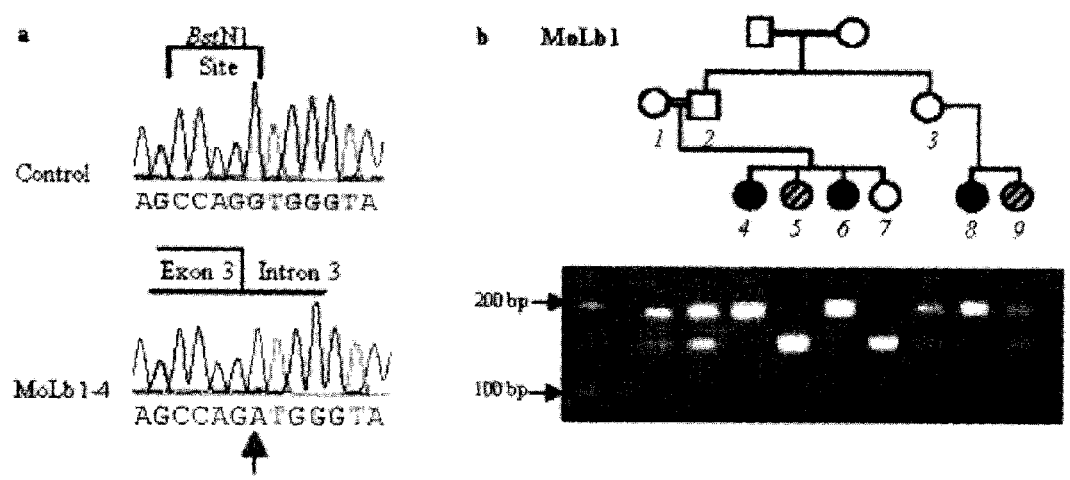
FIG. 3: Segregation of the IVS3+1G>A mutation in family MoLb1. a, sequence electropherogram showing the exon3/intron3 boundary in normal control and in patient MoLb1-4. The recognition site of the restriction enzyme BstN1, CCWGG, is abolished by the splice mutation IVS3+1G>A. Normal control sequence: AGCCAGGTGGGTA (SEQ ID NO: 43); MoLb1-4 patient sequence: AGCCAGATGGGTA (SEQ ID NO: 44). b, Partial pedigree of MoLb1 showing the genotypes of the different members for the IVS3+1 mutation. The band at 206 bp is uncut by BstN1 and thus contains the mutation, the band at 153 bp resulted from the digestion of the normal allele with BstN1. The parents (1, 2, and 3) are heterozygous for the mutation, the affected women, 4, 6, and 8, are homozygous for the mutation, the unaffected sister, 7, is homozygous for the normal allele, as is 5 whose status with respect to molar pregnancy is unknown. Member 9 is a carrier for the mutation and her phenotype is also unknown.
Figure 4:
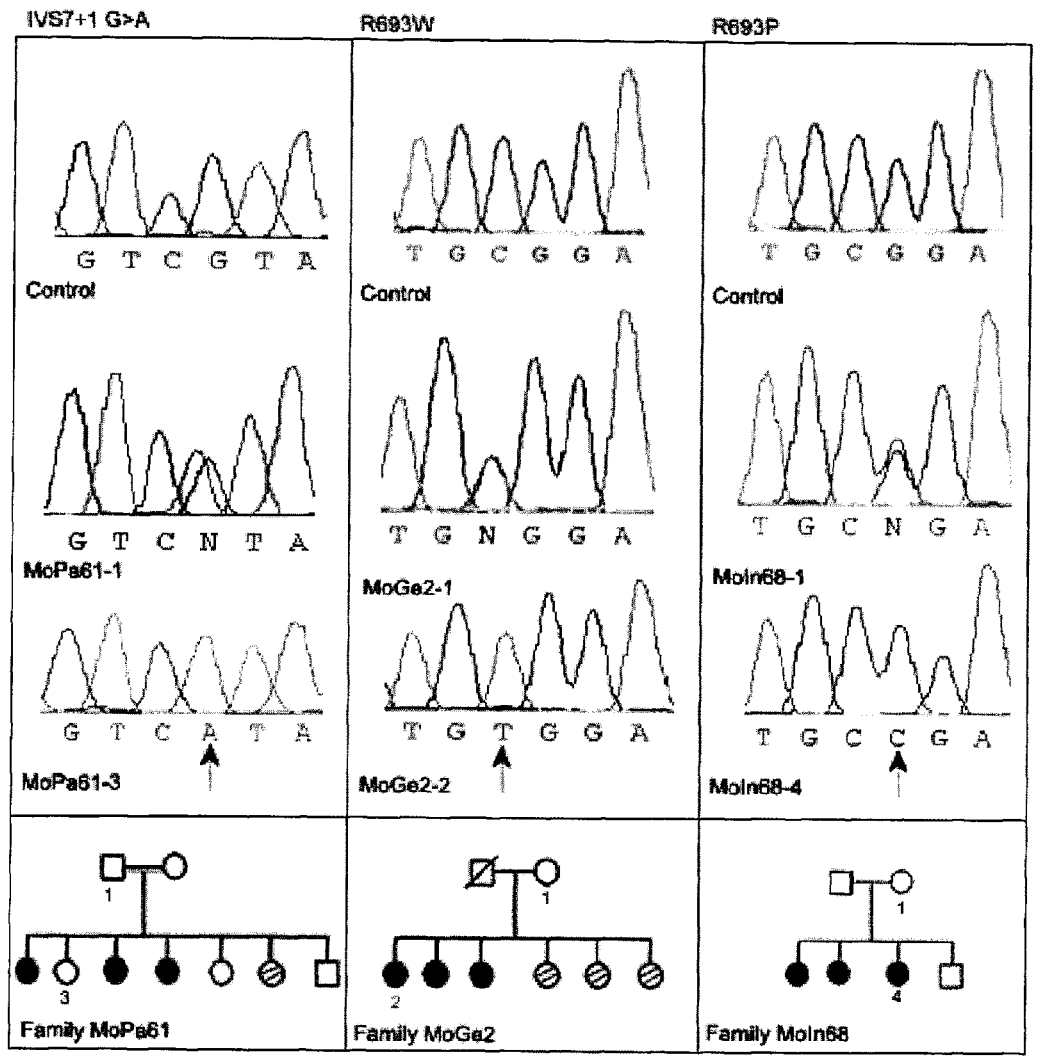
FIG. 4: DNA sequence electrophorograms showing the IVS7+1 G>A, R693W mutations. For each mutation, the control individuals homozygous for the normal alleles are shown at the top; the mothers of the patients who are heterozygous for the normal and mutant alleles are shown in the middle; and affected females, homozygous for the mutations are shown at the bottom. The pedigree symbols are as described in the legend of FIG. 1.

By screening the additional genes identified by the new definition of the proximal boundary herein, applicant identified in NALP7 (also called PYPAF3) two different mutations affecting the invariant G of the GT splice donor site at the junction of exon 3/intron 3 (IVS3+1G>A) in a patient from MoLb1 (FIG. 3a) and at the junction of exon 7/intron 7 (IVS7+1G>A) in a patient from MoPa61 (FIG. 4). The mutation in family MoLb1 abolishes a recognition site for the restriction enzyme BstN1 that applicant used to detect the mutation in the other members of the family (FIG. 3b) and in 100 control women (with 5 to 16 children) from various ethnic groups. In family MoPa61, IVS7+1G>A, the mutation was investigated in the other members of the family and controls by DNA sequencing (FIG. 4). Both mutations segregate with the disease phenotype in their respective families and were not found in the 200 control chromosomes screened. In family MoGe2, applicant identified in exon 5, a C to T change substituting an arginine for a tryptophan at amino acid 693, R693W (FIG. 4), a conserved residue in chimpanzee and cow NALP7 as well as in human, cow, and dog NALP2. By DNA sequencing, it was found that this change co-segregates with the disease status in MoGe2 and is not present on 274 chromosomes from control women with five to sixteen children.

To assess the role of NALP7 in recurrent molar pregnancies occurring in single-family members that are not homozygous at 19q13.4 markers and could not be investigated for linkage to 19q13.4 (because of the absence of other female siblings with known pregnancy outcomes in the family), applicant screened NALP7 in eight such cases and identified additional set of five new mutations, C399Y, E99X, C84Y, K379N, and D657V that were not found in controls. Mutations, clinical data, and coding DNA polymorphisms found in the different families and patients are summarized in Table 1.

TABLE 1

Summary of mutations, ethnic origin, and clinical manifestations of the patients

| Family | Population | Location | Nucleotide change | Amino acid change | Clinical manifestations and outcomes | Reference |
|---|---|---|---|---|---|---|
| Familial cases of recurrent moles | | | | | | |
| MoLb1 | Lebanese | Intron 3 | IVS3 + 1G > A | | NP, SB, SA, CHM, PHM, PTD, preeclampsia | Seoud et al, 1995, Helwani et al., 1999 |
| MoPa61 | Pakistani | Intron 7 | IVS7 + 1G > A | | SA, CHM | Mazhar and Janjua 1995 |
| MoGe2 | German | Exon 5 | 2077C > T | R693W | CHM | Kircheisen and Ried, 1994 |
| MoCh76 | Chinese | Exon 3 | 365G > T | E99X | SB, CHM | Present study |
| | | Exon 5 | 2040A > T | D657V | | |
| Single family member with recurrent moles | | | | | | |
| MoCh71 | Chinese | Exon 2 | 321G > A | C84Y Heterozygous | 2 CHMs | Present study |
| MoCh73 | Chinese | Exon 4 | 1207G > C | K379N Heterozygous | 2 CHMs, 1 PHM | Present study |
| MoCa57 | Moroccan | Exon 4 | 1266G > A | C399Y Heterozygous | SA, BO, TP + CHM | Present study |

With reference to Table 1, the phenotype of the conceptuses were as reported in the original papers listed under Reference. Nucleotide positions are given according to RefSeq mRNA NM_206828, amino acid positions according to Q8WX94. NP, normal pregnancy; SB, stillbirth; SA, spontaneous abortion; CHM, complete hydatidiform mole, PHM, partial hydatidiform mole PTD, persistent trophoblastic disease; BO, blighted ovum; TP, twin pregnancy.

Example 4

Expression of NALP7 in Normal Tissues

A recent study has reported NALP7 expression in a broad range of normal adult tissues (Kinoshita et al., 2005). To investigate the role of NALP7 in the pathology of moles, a disease caused by a maternal defective gene, applicant investigated its transcription by RT-PCR in normal human uterus and ovary using two combinations of primers located in exons 6 and 8, and in exons 8 and 11. Applicant identified two NALP7 transcripts, V1 and V2, in both tissues and also in EBV lymphoblastoid cell lines from normal subjects, and first trimester chorionic villi. By DNA sequencing, we found that V1 and V2 are due to the exclusion or inclusion of exon 10, respectively.

Example 5

Effect of the Splice Mutations on NALP7 Transcription

Figure 5:
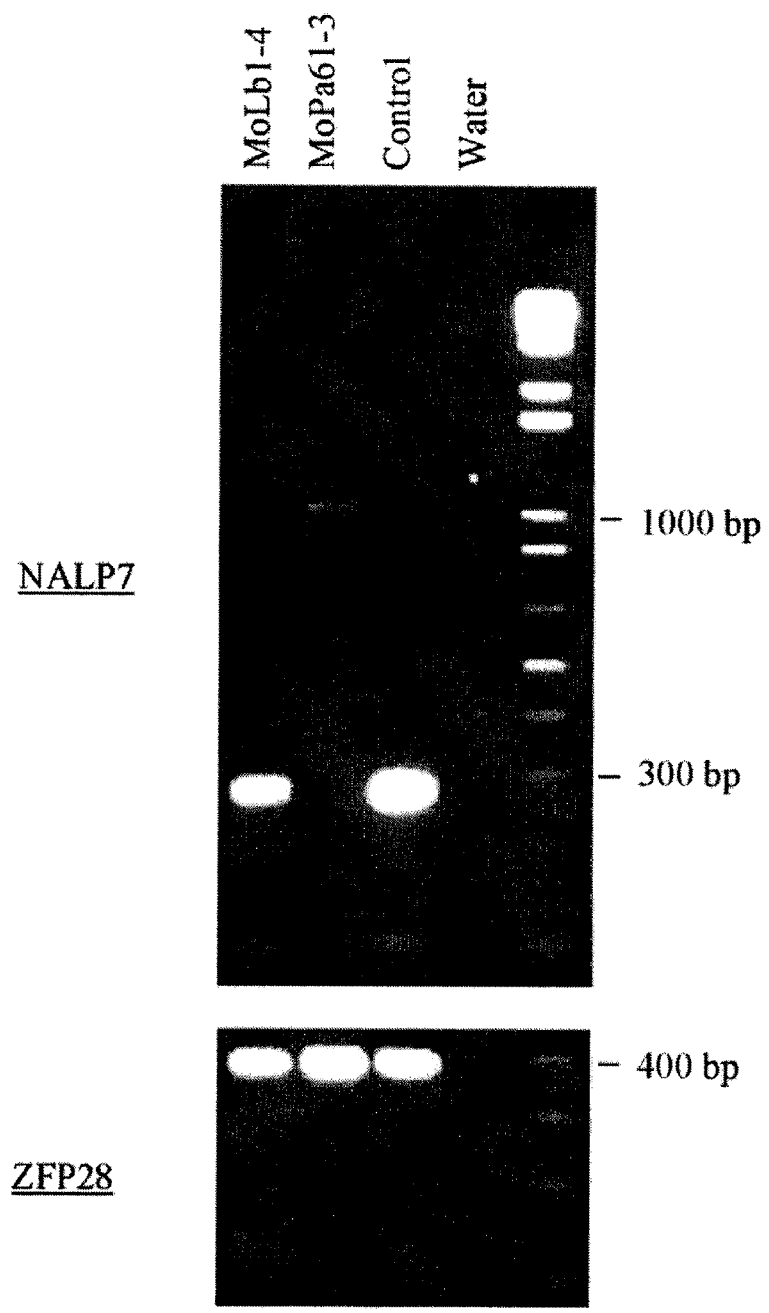
FIG. 5: Abnormal RNA splicing resulting from IVS7+1G>A mutations on RNA extracted from EBV-transformed lymphoblastoid cell lines from the patients. RT PCR using primers located in exons 6 and 8 of NALP7 in one patient from family MoPa61 amplified a ~1 kb fragment present only in the patient from MoPa61, but not in a patient from MoLb1 (with IVS+1G>A) or in control. The ZNF28 gene was amplified on the same samples to show the equal amount of cDNA.

The two splice mutations identified herein affect exons 3 and 7 (these exons are present in all reported transcriptional isoforms). Using GENSCAN (http://genes.mit.edu/GENSCAN.html), the splice mutation IVS3+1G>A was predicted to result in the skipping of exon 3, while SSPNN (http://www.fruitfly.org/seq_tools/splice.html) analysis, predicts the activation and usage of a cryptic intronic splice site located 4-bp downstream of exon 3. Using both programs, GENSCAN and SSPNN, the splice mutation IVS7+1G>A is predicted to lead to the skipping of exon 7. Primers located in exons 6 and 8 amplified a large fragment (~1 kb) in the three patients from MoPa61, that does not correspond to the size of the genomic fragment (2635 bp) between the two primers (FIG. 5). This fragment was observed only after reverse transcription and was not present in 5 normal control subjects. Applicant cloned and sequenced this fragment and found it to correspond to the inclusion of the entire intron 7. The inclusion of intron 7 is expected to add next to exon 7 only one amino acid, a serine, followed by a stop codon, TAA, leading to a shorter protein of 824 amino acids.

Example 6

Primers for PCR Amplification of Regions of NALP7

```
Exon 1:
PCR
Fwd: NALP7ex1a
                                        (SEQ ID NO: 6)
GCCCAATTACAGCCAAATCCCTGAG Rev: NALP7ex1b
Product Size: 604 bp
                                        (SEQ ID NO: 7)
GGCCGAGGCAGACAGATTACCTAAA Sequencing
NALP7ex1a
(see SEQ ID NO: 6 above)
NALP7Rev2
                                        (SEQ ID NO: 35)
TCCTTCCAGCATCCTCGCAC Exon 2:
PCR
NALP7ex2-fwd
                                        (SEQ ID NO: 8)
ACCGTGCTGGGCCAGATTTTCAGT NALPex3-rev
Product size: 777 bp
                                        (SEQ ID NOs: 9; 11)
GCAGAGGTTGCAATGAGCAGAGACG Sequencing
NALP7ex2-fwd
(see SEQ ID NO: 8 above)

NALP7ex2rev2
                                        (SEQ ID NO: 36)
ATGACCAGGACACCCCAGGTTCTA Exon3:
PCR
NALPex3-fwd
                                        (SEQ ID NO: 10)
CCACCATGCCTGGCTGACACTTTAT NALPex3-rev
Product size: 340 bp
                                        (SEQ ID NOs: 11; 9)
GCAGAGGTTGCAATGAGCAGAGACG Sequencing
NALP7ex3-fwd
(see SEQ ID NO: 10 above)

NALP3ex2rev2
                                        (SEQ ID NO: 37)
CACCTTGCATGCTCTCAAACACCA Exon 4:
1-PCR
NALP7ex4-1 fwd
                                        (SEQ ID NO: 12)
GTAGTGGCTCCGTCTCTGCTCATTG NALP7ex4-1 rev
Product Size: 737 bp
                                        (SEQ ID NO: 13)
AGGCCATCGACCACGAACAGGATTC Sequencing
NALP7ex4-1 fwd
(see SEQ ID NO: 12 above)

NALP7ex4-1 rev
(see SEQ ID NO: 13 above)

2-PCR
NALPex4-2 fwd
                                        (SEQ ID NO: 14)
GACGACGTCACTCTGAGAAACCAAC NALPex4-2 rev
Product size: 757 bp
                                        (SEQ ID NO: 15)
TGCAGAGGAAACGCAGGAACAGC Sequencing
NALPex4-2 fwd
(see SEQ ID NO: 14 above)

NALPex4-2 rev
(see SEQ ID NO: 15 above)

3-PCR
NALP7ex4-3 fwd
                                        (SEQ ID NO: 16)
TTTGCTGAAGAGGAAGATGTTACCC
```

-continued

NALP7ex4-3 rev
Product size: 722 bp
                                      (SEQ ID NO: 17)
CGAGGCCGAATAAGAAGTGTCCTAC Sequencing
NALPex4-3 fwd
(see SEQ ID NO: 16 above)

NALP7ex4-3 rev
(see SEQ ID NO: 17 above)

4-PCR
NALP7ex4-4 fwd
                                      (SEQ ID NO: 18)
GTGGGCGCAGATGTCCGTGTTC NALP7ex4-4 rev
Product size: 803 bp
                                      (SEQ ID NO: 19)
CCTAATTGCCAAGTCGTGTCTCC Sequencing
NALP7ex4-4 fwd
(see SEQ ID NO: 18 above)

NALP7ex4-4 rev
(see SEQ ID NO: 19 above)

Exon 5:
PCR
NALP7ex-5 fwd
                                      (SEQ ID NO: 20)
GGTCTCAGTTTCTAGCCCAAGTT NALP7ex-5 rev
                                      (SEQ ID NO: 21)
ACACGGTGAAAACCTGTCTGTGC Sequencing
NALP7ex-5 fwd
(see SEQ ID NO: 20 above)

NALP7ex5rev2_Seq
Product size: 839 bp
                                      (SEQ ID NO: 38)
CAAGAAGCTTAGTCATCGTT Exon 6:
PCR
NALP7ex6-fwd
                                      (SEQ ID NO: 22)
CCACTGCACCCGGCCAAGAACTT NALP7ex6-rev
Product size: 597 bp
                                      (SEQ ID NO: 23)
GCTGGGGGCCACTGCTCTCAATC Sequencing
NALP7ex6-fwd
(see SEQ ID NO: 22 above)

NALP7ex6-rev
(see SEQ ID NO: 23 above)

Exon 7:
PCR
NALP7ex7-fwd
                                      (SEQ ID NO: 24)
GATCACGCCTTTGCATTCCAGACTG NALP7ex7-rev
Product size: 471 bp
                                      (SEQ ID NO: 25)
AACTCAGATGATCCGCCCACCTCTC -continued Sequencing
NALP7ex7Seq
                                      (SEQ ID NO: 39)
AGCTGATAGGGTATACTCTG NALP7ex7-rev
(see SEQ ID NO: 25 above)

Exon 8:
PCR
NALP7ex8 fwd
                                      (SEQ ID NO: 26)
AAAACAACACCTGTGTCCTGTGATG NALP7ex8 rev
Product size: 849 bp
                                      (SEQ ID NO: 27)
TTAACATGTTTCTACCTGTATCTGC NALP7ex8f2
                                      (SEQ ID NO: 41)
TGGCCATGATGACTCCCACAGG NALP7ex8r2
Product size: 418 bp
                                      (SEQ ID NO: 42)
CCAGGTTTTTAAAAGTTACATTTG Sequencing
NALP7ex8f2
(see SEQ ID NO: 26 above)

NALP7ex8r2
(see SEQ ID NO: 27 above)

Exon 9:
PCR
NALP7ex9-a
                                      (SEQ ID NO: 28)
CTTCACAGGGCGTTAGCCAGAGG NALP7ex9b
Product size: 456 bp
                                      (SEQ ID NO: 29)
CCAGCCCGGGAAAGATGACAAGA Sequencing
NALP7ex9-a
(see SEQ ID NO: 28 above)

NALP7ex9b
(see SEQ ID NO: 29 above)

Exon 10:
PCR
NALP7ex10afwd
                                      (SEQ ID NO: 30)
AAGGTGCTGGGGCTACAGGTGTCT NALP7ex10arev
Product size: 787 bp
                                      (SEQ ID NO: 31)
GCCAACATGGTGAAACCCCTCTC Sequencing
NALP7ex10afwd
(see SEQ ID NO: 30 above)

NALP7ex10aseq_r
                                      (SEQ ID NO: 40)
AAACCCATACCTGAGTAT Exon 11:
PCR
NALP7ex11 fwd
                                      (SEQ ID NO: 32)
CTGTCCCCCAGAAAATCCCAAAAAC

```
                                    -continued
NALP7ex11 rev
Product size: 588 bp
                                                        (SEQ ID NO: 33)
CAACCGAATCATCCCTGAACTTC Sequencing
NALP7ex11 fwd
  (see SEQ ID NO: 32 above)

NALP7ex11 rev
  (see SEQ ID NO: 33 above)
```

To assess the IVS3+1G>A mutation using the restriction enzyme BstN1, the following primers were used to amplify a 204 bp fragment that was digested with the enzyme:

```
                                                        (SEQ ID NO: 10)
NALPex3-fwd         CCACCATGCCTGGCTGACACTTTAT (SEQ ID NO: 34)
NALPex3b2           CAAACACCAAACTCATGACCATA
Product size: 204 bp
```

Example 8

Cytokine Release in Peripheral Mononuclear Cells from Patients with Mutations in NALP7

Figure 9:
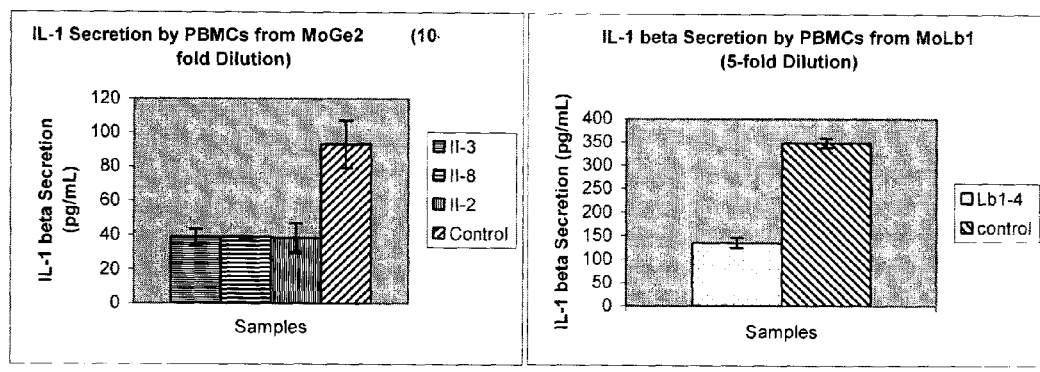
FIG. 9: IL-1β secretion by PBMCs with NALP7 mutations. Blood was collected from one patient from family MoLb1 (Lb1-4 in the right panel) and three patients from MoGe2 (Il-2, Il-3, Il-8, left panel). PBMCs were isolated from blood using the Ficoll gradient technique, 500,000 cells/well were stimulated with 100 ng/mL of LPS, supernatant was collected 20 hours later and IL-1β levels at the indicated dilutions were measured using ELISA.
Figure 10:
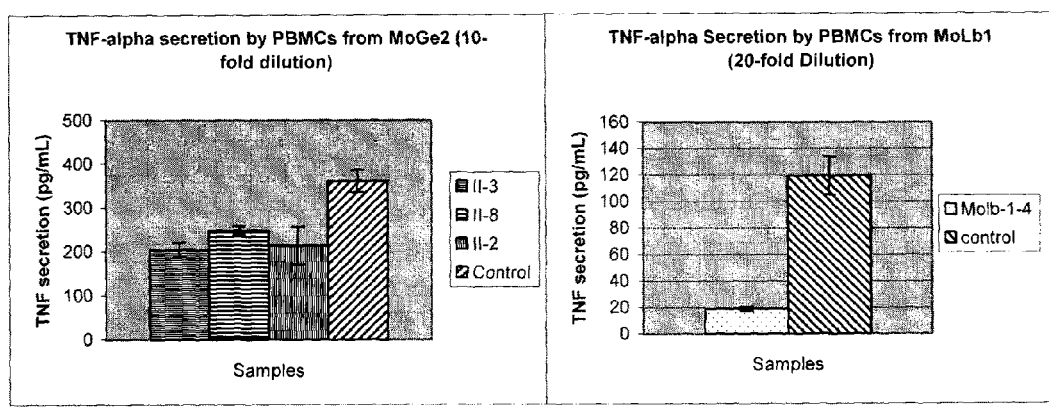
FIG. 10: TNFα secretion by PBMCs with NALP7 mutations. TNFα levels were measured as described in Example 8 below.

The ability of peripheral blood mononuclear cells (PBMCs) harbouring homozygous NALP7 mutations to secrete interleukin-1β (IL-1β) and TNF alpha (TNFα) in response to stimulation with bacterial lipopolysaccharide (LPS) was assessed. PBMCs were isolated from patients with NALP7 mutations (MoLb1 with IVS3+1G>A and MoGe2 with R693W) and control subjects using Ficoll gradient, stimulated with 100 ng/mL of LPS for twenty hours and the supernatants were collected for cytokine quantification using ELISA. Applicant found that the concentration of IL-1β and TNFα in the supernatant of patient' PBMCs was significantly lower than that of controls (FIGS. 9 and 10).

Although the present invention has been described hereinabove by way of specific embodiments thereof, it can be modified, without departing from the spirit and nature of the subject invention as defined in the appended claims. Throughout this application, various references are referred to describe more fully the state of the art to which this invention pertains. The disclosures of these references are hereby incorporated by reference into the present disclosure.

REFERENCES

Helwani, M. N. et al., *Hum Genet* 105, 112-5 (1999).
Hodges, M. D., Rees, H. C., Seckl, M. J., Newlands, E. S. & Fisher, R. A., *J Med Genet* 40, e95 (2003).
Kinoshita, T., Wang, Y., Hasegawa, M., Imamura, R. & Suda, T., *J Biol Chem* 280, 21720-5 (2005).
Kircheisen R, Ried T, *Hum Reprod* 9:1783 (1994).
Mazhar, S. & Janjua, S., *J Pakistan Inst Med Sci* 6, 383-6 (1995).
Moglabey, Y. B. et al., *Hum Mol Genet* 8, 667-71 (1999).
Okada, K. et al., *Cancer Sci* 95, 949-54 (2004).
Sensi, A. et al., *Eur J Hum Genet* 8, 641-4 (2000).
Seoud M, Khalil A, Frangieh A, Zahed L, Azar G, Nuwayri-Salti N., *Obstet Gynecol* 86:692, (1995).
Silver, R. M., Lohner, W. S., Daynes, R. A., Mitchell, M. D. & Branch, D. W., *Biol Reprod* 50, 1108-12 (1994).

---

What is claimed is:

1. A method for diagnosing a predisposition for molar pregnancy in a human female subject, the method comprising detecting an alteration in the sequence of a NALP7 gene or the sequence of its mRNA or encoded polypeptide in a tissue sample from said subject relative to the sequence of a wild-type NALP7 gene or the sequence of its mRNA or encoded polypeptide, wherein said alteration is:

a) a substitution of G with A at the splice donor site at the boundary of exon 3 and intron 3 (IVS3+1G>A);
  b) a substitution of G with A at the splice donor site at the boundary of exon 7 and intron 7 (IVS7+1G>A);
  c) a substitution of C with T corresponding to the first position of the codon for Arg 693 of the NALP7 polypeptide, resulting in a Arg to Trp substitution;
  d) a substitution of G with A corresponding to the second position of the codon for Cys 84 of the NALP7 polypeptide, resulting in a Cys to Tyr substitution;
  e) a substitution of G with A corresponding to the second position of the codon for Cys 399 of the NALP7 polypeptide, resulting in a Cys to Tyr substitution;

f) a substitution of G with C corresponding to the third position of the codon for Lys 379 of the NALP7 polypeptide, resulting in a Lys to Asn substitution;
g) a substitution of G with T corresponding to the first position of the codon for Glu 99 of the NALP7 polypeptide, resulting in a substitution for a stop codon; and/or
h) a substitution of A with T corresponding to the second position of the codon for Asp 657 of the NALP7 polypeptide, resulting in a Asp to Val substitution wherein if the NALP7 polypeptide is used for detecting said alteration, said alteration is detected by sequencing of the NALP7 polypeptide, and wherein said alteration indicates that the subject has a predisposition for molar pregnancy.

2. The method of claim 1, wherein said substitution of G with A at the splice donor site at the boundary of exon 3 and intron 3 (IVS3+1G>A) is associated with a loss of a cleavage site for the restriction endonuclease BstN1in the NALP7 gene.

3. The method of claim 1, further comprising amplification of a nucleic acid sequence suspected of comprising the alteration in the sample prior to the detection of the alteration.

4. The method of claim 1, wherein detection of the alteration in the sequence of the NALP7 gene or the sequence of its mRNA is performed using a method selected from:
   a) sequencing of the NALP7 nucleic acid sequence;
   b) hybridization of a nucleic acid probe capable of specifically hybridizing to a NALP7 nucleic acid sequence comprising the alteration and not to a corresponding wild-type NALP7 nucleic acid sequence;
   c) restriction fragment length polymorphism analysis (RFLP);
   d) amplified fragment length polymorphism PCR (AFLP-PCR); and/or
   e) amplification of a nucleic acid fragment comprising a NALP7 nucleic acid sequence using a primer specific for the alteration, wherein the primer produces an amplified product if the alteration is present and does not produce the same amplified product when a corresponding wild-type NALP7 nucleic acid sequence is used as a template for amplification.

5. The method of claim 4, wherein said primer comprises a nucleotide sequence selected from SEQ ID NOs: 6-42.

6. The method of claim 1, further comprising determining cytokine release of an immune cell of said subject, wherein a decrease in cytokine release relative to a control level of cytokine release is further indicative that the subject suffers from or has a predisposition for the reproductive condition.

7. The method of claim 6, wherein the control level is selected from an established standard and a level of cytokine release of an immune cell comprising a wild-type NALP7 nucleic acid.

8. The method of claim 6, wherein the immune cell is a lymphocyte or monocyte.

9. The method of claim 6, wherein the immune cell is a peripheral blood mononuclear cell (PBMC).

10. The method of claim 6, wherein the cytokine is selected from interleukin-1β (IL-1 β) and TNF alpha (TNFα).

* * * * *